US010077466B2

(12) United States Patent
Webster et al.

(10) Patent No.: US 10,077,466 B2
(45) Date of Patent: Sep. 18, 2018

(54) STABLE NANOREPORTERS

(71) Applicant: NanoString Technologies, Inc., Seattle, WA (US)

(72) Inventors: Philippa Jane Webster, Seattle, WA (US); Timothy Dahl, Juneau, AK (US)

(73) Assignee: NanoString Technologies, Inc., Seattle, WA (US)

( * ) Notice: Subject to any disclaimer, the term of this patent is extended or adjusted under 35 U.S.C. 154(b) by 0 days.

(21) Appl. No.: 15/082,398

(22) Filed: Mar. 28, 2016

(65) Prior Publication Data

US 2016/0273026 A1 Sep. 22, 2016

Related U.S. Application Data

(63) Continuation of application No. 13/957,029, filed on Aug. 1, 2013, now Pat. No. 9,376,712, which is a continuation of application No. 12/541,131, filed on Aug. 13, 2009, now Pat. No. 8,519,115.

(60) Provisional application No. 61/088,988, filed on Aug. 14, 2008.

(51) Int. Cl.
*C12Q 1/6811* (2018.01)

(52) U.S. Cl.
CPC .................................. *C12Q 1/6811* (2013.01)

(58) Field of Classification Search
None
See application file for complete search history.

(56) References Cited

U.S. PATENT DOCUMENTS

| | | | |
|---|---|---|---|
| 5,137,819 | A | 8/1992 | Kilburn et al. |
| 5,202,247 | A | 4/1993 | Kilburn et al. |
| 5,293,050 | A | 3/1994 | Chapple-Sokol et al. |
| 5,320,814 | A | 6/1994 | Walt et al. |
| 5,354,707 | A | 10/1994 | Chapple-Sokol et al. |
| 5,496,934 | A | 3/1996 | Shoseyov et al. |
| 5,543,838 | A | 8/1996 | Hosier et al. |

(Continued)

FOREIGN PATENT DOCUMENTS

| | | |
|---|---|---|
| WO | WO-9707245 | 2/1997 |
| WO | WO-9714028 | 4/1997 |

(Continued)

OTHER PUBLICATIONS

Collins et al. Nucleic Acids Research. 1997. 25(15):2979-2984.*

(Continued)

*Primary Examiner* — Joseph G Dauner
(74) *Attorney, Agent, or Firm* — Cooley LLP; Ivor R. Elrifi; Matthew Pavao

(57) ABSTRACT

The present invention relates to compositions and methods for detection and quantification of individual target molecules in biomolecular samples. In particular, the invention relates to improved, stable nanoreporter probes that are capable of binding to and identifying target molecules based on the probes' uniquely detectable signal. Methods for identifying target-specific sequences for inclusion in the probes are also provided, as are methods of making and using such probes. Polynucleotide sequences of certain nanoreporter components are also provided. The probes can be used in diagnostic, prognostic, quality control and screening applications.

26 Claims, 12 Drawing Sheets

Specification includes a Sequence Listing.

(56) References Cited

U.S. PATENT DOCUMENTS

| | | | | | |
|---|---|---|---|---|---|
| 5,804,384 | A * | 9/1998 | Muller | C12Q 1/6837 435/287.2 |
| 6,207,392 | B1 | 3/2001 | Weiss et al. | |
| 6,429,027 | B1 | 8/2002 | Chee et al. | |
| 6,942,968 | B1 | 9/2005 | Dickinson et al. | |
| 7,473,767 | B2 | 1/2009 | Dimitrov | |
| 8,519,115 | B2 | 8/2013 | Webster et al. | |
| 9,046,477 | B2 | 6/2015 | Emedcoles et al. | |
| 9,228,948 | B2 | 1/2016 | Emedcoles et al. | |
| 9,297,762 | B2 | 3/2016 | Emedcoles et al. | |
| 9,304,084 | B2 | 4/2016 | Emedcoles et al. | |
| 2001/0002315 | A1 | 5/2001 | Schultz et al. | |
| 2001/0007775 | A1 | 7/2001 | Seul et al. | |
| 2001/0023078 | A1 | 9/2001 | Bawendi et al. | |
| 2001/0029049 | A1 | 10/2001 | Walt et al. | |
| 2001/0034034 | A1 | 10/2001 | Bruchez et al. | |
| 2001/0053334 | A1 | 12/2001 | Chen et al. | |
| 2002/0028457 | A1 | 3/2002 | Empedocles et al. | |
| 2002/0034737 | A1 | 3/2002 | Drmanac | |
| 2002/0034827 | A1 | 3/2002 | Singh et al. | |
| 2002/0039728 | A1 | 4/2002 | Kain et al. | |
| 2002/0051971 | A1 | 5/2002 | Stuelpnagel et al. | |
| 2002/0068018 | A1 | 6/2002 | Pepper et al. | |
| 2002/0177141 | A1 | 11/2002 | Chee et al. | |
| 2002/0187515 | A1 | 12/2002 | Chee et al. | |
| 2003/0008323 | A1 | 1/2003 | Ravkin et al. | |
| 2003/0028981 | A1 | 2/2003 | Chandler et al. | |
| 2003/0186426 | A1 | 10/2003 | Brewer et al. | |
| 2005/0064435 | A1 | 3/2005 | Su et al. | |
| 2005/0170346 | A1* | 8/2005 | Westh | C12Q 1/6816 435/6.18 |
| 2005/0233318 | A1 | 10/2005 | Chee et al. | |
| 2007/0166708 | A1 | 7/2007 | Dimitrov et al. | |
| 2010/0015607 | A1 | 1/2010 | Geiss et al. | |
| 2010/0112710 | A1 | 5/2010 | Geiss et al. | |
| 2010/0261026 | A1 | 10/2010 | Ferree et al. | |
| 2010/0262374 | A1 | 10/2010 | Hwang et al. | |
| 2011/0229888 | A1* | 9/2011 | Hengen | C12Q 1/6816 435/6.11 |

FOREIGN PATENT DOCUMENTS

| | | | | | |
|---|---|---|---|---|---|
| WO | WO-9918434 | | 4/1999 | |
| WO | WO-200073777 | | 12/2000 | |
| WO | WO-200100875 | | 1/2001 | |
| WO | WO-07076128 | A2 | 7/2007 | |
| WO | WO-07076129 | A2 | 7/2007 | |
| WO | WO-07076132 | A2 | 7/2007 | |
| WO | WO 2007076128 | A2 * | 7/2007 | B82Y 5/00 |
| WO | WO-07139766 | A2 | 12/2007 | |
| WO | WO-08124847 | A2 | 10/2008 | |
| WO | WO 2010/019826 | A1 | 2/2010 | |
| WO | WO-10053790 | A1 | 5/2010 | |

OTHER PUBLICATIONS

"The Polymerase Chain Reaction." *Current Protocols in Molecular Biology*. Ausubel et al., eds. John Wiley & Sons Inc. Chapter 15. (2009).

Altschul et al. "Gapped BLAST and PSI-BLAST: A New Generation of Protein Database Search Programs." *Nucl. Acids Res.* 25.17(1997):3389-3402.

Britten et al. "Analysis of Repeating DNA Sequences by Reassociation." *Meth Enzymol.* 29(1974):363-406.

Fortina et al. "Digital mRNA Profiling." *Nature Biotech.* 26.3(2008):293-294.

Geiss et al. "Direct Multiplexed Measurement of Gene Expression with Color-Coded Probe Pairs." *Nature Biotech.* 26.3(2008):317-325.

Guan et al. "Vectors that Facilitate the Expression and Purification of Foreign Peptides in *Escherichia coli* by Fusion to Maltose-Binding Protein." *Gene.* 67(1988):21-30.

Hyrup et al. "Peptide Nucleic Acids (PNA): Synthesis, Properties and Potential Applications." *Bioorg. Med. Chem.* 4.1(1996):5-23.

Malkov et al. "Multiplexed Measurements of Gene Signatures in Different Analytes Using the Nanostring nCounter™ Assay System." *BMC Res. Notes.* 2(2009):80.

Mathews et al. "Expanded Sequence Dependence of Thermodynamic Parameters Improves Prediction of RNA Secondary Structure." *J. Mol. Biol.* 288(1999):911-940.

Perry-O'Keefe et al. "Peptide Nucleic Acid Pre-Gel Hybridization: An Alternative to Southern Hybridization." *PNAS.* 93(1996):14670-14675.

Smith. "Purification of Glutathione S-Transferase Fusion Proteins." *Meth. Mol. Cell Biol.* 4(1993):220-229.

Tomme et al. "An Internal Cellulose-Binding Domain Mediates Adsorption of an Engineered Bifunctional Xylanase/Cellulase." *Protein Eng.* 7.1(1994):117-123.

Wetmur. "Hybridization and Renaturation Kinetics of Nucleic Acids." *Annu. Rev. Biophys. Bioeng.* 5(1976):337-361.

Zuker. "Mfold Web Server for Nucleic Acid Folding and Hybridization Prediction." *Nucl. Acids Res.* 31.13(2003):3406-3415.

Alfano et al., "Optical Sensing, Imaging, and Manipulation for Biological and biomedical applications" SPIE—The International Society for Optical Engineering, Jul. 2000, vol. 4082, Taiwan.

Ferguson et al., "High-Density Fiber-Optic DNA Random Microsphere Array" *Analytical Chemistry* 72 (22), 5618-5624 (2000).

Steemers et al., "Screening unlabeled DNA targets with randomly ordered fiber-optic gene arrays." *Nature Biotechnology.* 18, 91-94 (2000).

Werner et al., "Current status of DNA sequencing by single molecule detection" Proc. SPIE 3602, Advances in Fluorescence Sensing Technology IV, 355, (1999).

* cited by examiner

Fig. 2A
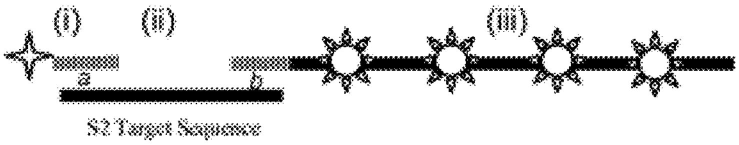
Fig. 2E
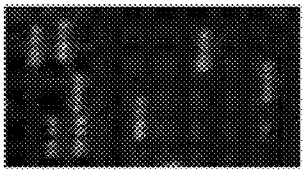
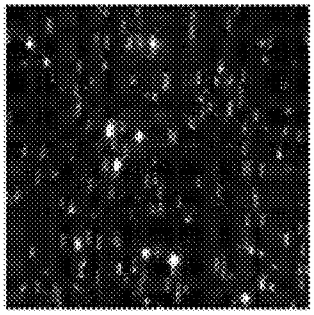
Fig. 2B
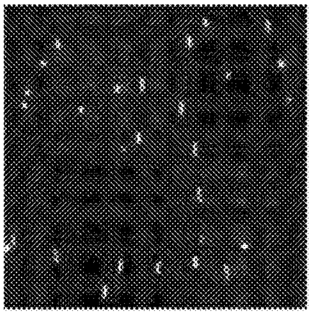
Fig. 2C
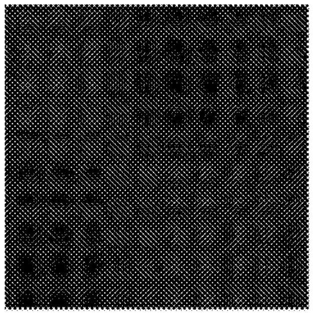
Fig. 2D 40 reporters from 2 'representative' samples:

89-96% correlation between the two systems, with greater than 100 fold increase in signal with DV1

AAGCTTGGCCACACAGCTTGAGTATTCTATAGTGTCACCTAAATAGCTTGGCGTAATCATGGTCATAGCTGT
TTCCTGTGTGAAATTGTTATCCGCTCACAATTCCACACAACATACGAGCCGGAAGCATAAAGTGTAAAGCCT
GGGGTGCCTAATGAGTGAGCTAACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCACAAAAATC
GACGCTCAAGTCAGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTTTCTACGGGGT
CTGACGCTCAGTGGAACGAAAACTCACGTTAAGGGATTTTGGTCATGAGATTATCAAAAAGGATCTTCACCT
AGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCC
CCGTCGTGTAGATAACTACGATACGGGAGGGCTTACCATCTGGCCCCAGTGCTGCAATGATACCGCGAGACC
CACGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATT
CTCTTACTGTCATGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTCTCGCGCGTTTCGGTGATGACG
GTGAAAACCTCTGACACATGCAGCTCCCGGAGACGGTCACAGCTTGTCTGTAAGCGGATGCCGGGAGCAGAC
AAGCCCGTCAGGGCGCGTCAGCGGGTGTTGGCGGGTGTCGGGGCTGGCTTAACTATGCGGCATCAGAGCAGA
TTGTACTGAGAGTGCACCATATGCGGTGTGAAATACCGCACAGATGCGTAAGGAGAAAATACCGCATCAGGA
AATTGTAAGCGTTAATATTTTGTTAAAATTCGCGTTAAATTTTTGTTAAATCAGCTCATTTTTTAACCAATA
GGCCGAAATCGGCAAAATCCCTTATAAATCAAAAGAATAGACCGAGATAGGGTTGAGTGTTGTTCCAGTTTG
GAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCGCGTAACCACCACACCCGCCGCGCT
TAATGCGCCGCTACAGGGCGCGTCCATTCGCCATTCAGGCTGCGCAACTGTTGGGAAGGGCGATCGGTGCGG
GCCTCTTCGCTATTACGCCAGCTGGCGAAAGGGGGATGTGCTGCAAGGCGATTAAGTTGGGTAACGCCAGGG
TTTTCCCAGTCACGACGTTGTAAAACGACGGCCAGTGAATTGTAATACGACTCACTATAGGGCGAATTAGTG
GATGAGAAGACCTGCAGAAAGAATTC (SEQ ID NO:27)

Fig. 9

8 space
TCTAGAGAGAAAGGCTACGAAGATCCGGACATCAAAAGATCAAAACATGCGGAGATCGAC
ACATCCAAAAATGAACAGATAACAGGATCAGAGGGTCAAGAAGTGAAACCATCGAGGAGT
CGCAGACTACGAAGATGGACAAGTGAGCAACAGCTGCGATGGAGAACTAAAGGAGTCGGG
AGGTACGGCAGTGAAGAAATGTGCACATGAAAAGCTGCCCGGGTGCGCAACTGGAGGACT
AGAAGAATGGCACAGTGACCCGGTGAGAGCCTGAGGAGGTGCGAGAATAGGGCGATAGGG
AGGTAACCCGATGGCGGACTAAAGAGATACGGACATGGACGGATAGGAGAGTCGCAAGAT
GGAAGGATCACAAAGTGAGCCGGTCCAAGCATACGCGGGTAAACGGATCAGAACGTAAAG
CGGTGGAAAAATACCCGAGTAGGAAGATAGCAAAATACCCAGGTCGAGCGATAGCCCACT
CGGCGAGTCCAAAACTGAAAAAATGGAGAGATGAGACACTAGCGGCATCGGACAGTAGAG
CAGTGAACGCATCAGAGAGTAGAAAAGTGAAGAACTGCGACGGTGAAACCATAACAGAGT
CAGAGGGTACACCCATACGACCCTACCGCAATACAAGGCTAAGACGGTCAGAGGATGGAC
GGCTCGCGAACTCACGCCGTGCCAAAGTGAAGAAGTACCAAAATAGGAGCGTAACGGCGT
AGAGAGGTAGACGAGTGAGACGGTGGGCAGCTCCCAAGGTCCGAGCATGGACAGGTGGCA
AAATCCAGCGGTCAGAAACTACGAGACTGGCCGGATGAAGAAATAAGGCGCTAGAGAGAT
ACGGGAGTGACAAGATGGACCACTAGCGAAGTCGGAGGGTGAAGACGTGAACAACTAGAC
CAGTACGGCACTAGCAGAATAGACCGATGAAAACCTGAAAAGATAACAGAGTGAAGGCAT
CGGAGGGTCGAGAAGTAAGAACGTGGAGCCATACACGAATAAAGCAGTACAAGGGTGGAC
AAATGAGGAAATCGGGAGGTCCCACGGTGAAAACGTAGGGAGGTGAACCAGTGGGAGAGT
CAACCAATACGAAGATGCGAGGATCC (SEQ ID NO:28)

Fig. 10A 10 space
CCATGGGAAAATGAGAGCCGCTCGACAAGGATAAAGAAAAGTCGCCCAACATCCGCCACG
CTAAGCGGCCCTAGGAGCCGGTAAACAAGCATGAAGAAACATGCGAGGCAATGACACAAA
CTCCAGGCGGGTGGAAAAGACTCGACGGAGATGCCACGCAATAGCGAAACCTGGAAGAGA
GTGGAAGCAAATAGGAAACAGTAGAGCAAAATGCCGCAGGATAGAAAACAGTGGCGCGCA
ATAAGCAGGAATAAAGCACAATAAAAAGAAGTAAACCGCACTAAAACAGCATCCAGACCG
CTGAAAAGAAATGGCGGCGAATGAAAAAAAGTCACAACCGGTGCAACAACCTGAAAAAGG
GTAGAGAGCCCTCCCGGGCAATAAAAGACGGTAAGAGGAAATCCCGAAAAGTGCAAAAAG
GTCAAAACGGGTGCAACAAAATGCCAAGGCGTGCAAGAAACTGAGGACGGATAAAAGACA
ATGCGGACGGGTACGACACGATAAGGAAAGATAAGGCGAAGTAAAAGCCGGTGCGGCAAA
ATACAACAGGCTGCCCAGAAGTACCGAGCGCTAGGCGGGAATGAGCGAGGGTAAAAGAGA
ATACACAACCCTGCAAGAAAGTCCGGGAAGCTAGGACCGGATACAGAGGAATAAGGAAGG
GTACACAGCAATACGAGCAGATGAACGAGCATACCAGAGAGATATCAGGCCTAAAAAACG
GTAACAAGAACTAGGAGGAGGTGCGAAGGCCTGGACCAAAATGGGACGAAGTAGGAGGGA
ATACACAACGATGGGACGAGATAGAGCCGGGTAGGCCAAAGTAGCACGGGATACCACAGA
ATACAGCGACGTACCGGAAAGTAGGAGAGACTGGAAACCCGTAAGGCAAGATAAGCGAGG
GCTAGCAGAACTAAAACAGACTGAACACGGATCAAGGCGAGTAGGCACGAGTACACGCCG
ATACGGACAAGTAGGCCGCAGTACGGAGAAGTAAACAGGGATGAGAGACAGTGAACAAGG
CTGAGACGAAATCACAGCAAATACAACAAAGTAGCGGCAAATAAACGGGAGTGGAACGCG
ATAGCAGGAAGTGACGGACAGCATGC (SEQ ID NO:29)

Fig. 10B 12 space
GAATTCGAGTACCACCTGATGAGCAGCAAGGTAACGGCGAAGATGAAAAGAAAAATGGAG
CGGCACGTACAAAAAAGGATGGCACCAGACATAGAAGAGGAGCTCAGCAAACGGCTGGAC
AGCGAAGTCCCAGGAAGCCTACCAAGGACAGATATCAAAGAAATAAGAAACAAACTGAGA
AAGCGCGTCGGAAGCGACGTACAAGCGGCAATGGCAGAGAGAGTAAAACAAACAGTGAAA
CCAACAATAAACGCCCAGGTAGGGCGAAAGGTAAACAAAAGGATCGAAAGACGAGTAAGG
CGGGAGATGGAAACAACGGTGCGAAAACCAGTGAAAAAGGGAGTCCAAAGCACCATGAAG
ACCACAATACGACACACCCTGGGAGGACACGTGGAGGAGCCGGTACGAAGCAGGGTACAA
GACAACATGCAAACAGAGGTAAAGGAACCGATAAAGAACGACATGGAAGGAAACGTAGGA
ACCCGAGTAGAGGAACGGATAGCGAACGACGTGCAACGCCACCTAGAACGAGAAGTCGCA
AGGGAAATAAACGGAGAGGTCCCACGGCCGATGAGCAGAAAAGTGGAAAAGGACCTGAAG
AGAAAAATGAGGACCACAATAAAGGACGGAATAAAAAACACACTCCCAGAGGAAATACAA
CGAGAAATAGGGAACAGGATGCAAAGAAGCATCAGAAAGGCAGTGCCAAAGGGAATCGGA
CGCAAGCTAAGACAGGCCCTAGACCGCGAAGTAAACGAACAACTCGGAGGGCGAATCAGG
CCCACCATGCAGAGCAAAATAAGAGACCAGATGCGCGGCAACCTGAGACCGAACCTAAAG
GAAAGGATAGAGGGAGAGGTCCAAGAAACGATGGCGGGCACCATGAGAAAGGAAGTCAAA
GTGCACCTAGCAACACAGATACCACGAGACATCGAAGCGAAGATACGGAAAAAGCTGGAG
AGGGCAATGAACAGAAAGCTACGGAAAGAAGTCAAGGACACAATGAGGGAGCAAGTCGAG
AGCGAGGTGGCCCGCCAAATAGGAGCAACAATGCGAGGCCAAGTGGGCACAACGATGAAA
GACCAACTAACACAGCCACTTCTAGAGTGCACGGATCCCTCGAGGGTACCAACCATGGAA
GCTAGCAAGCATGCAAACTGCAGAAGCTT (SEQ ID NO:30)

Fig. 11A

14 space
CTCGAGGAAAGACAGAGGGTAGCAGGCCACAGATCAAGGCGGCGAAATGGCCCGGAGCAC
GTAAGCACCACACGGTCACCAAGAGAGAATCAGAAGAGGCAAGTAAAAAAAGCGCGTAC
GGCACCCAAGGTGGACGCACAACAGTCACGGGAAAGAAGTCGAAGGCGGGCGCTCAGAAG
AGCGAAGTACACAACCAGACGGTACCGGAACACGATGCGCCAACAAGAATCAGCGGAAAG
ACATACCGGCGGACGGGTCGAAACACGAAAATGAAACCGCAGAAGTAAAGAGAAAAGGAT
CGCAGGAAGAGGATCAAGACAGAAAAATCGACAAAGCAAAGTGGACCGAAGAAGATCGAA
AAGAAGCACTCAGGACAGCTGAATCGCACAGACACGGTGACAAGACGAAAATGGACGACA
ACCGATAAGCGAAAAAAGATACCGGCGAGCGAGTCGAGAACACGAAGTCAAGGCGCAAGA
ATAGAGCAAACGAAGTAAACAGGACAGAATAGGAAGGGCAAAGTGGGAGAGAAAGGCTCG
GAACCGACGACTGCACCGAACAACGTGGGAGCCCACGGCTACAAAACGCCAGATCGAAGC
CCAGGAGTCGAAGAACAAAAGTAACGGCGCAGAAATAGAGAGAGGAGGCTAAAGCGGAAC
CAGTGAAGGAAAAGAAATAACGGGCCCAAGGTGAAGAAAAAGAAGTGGCAGGAACGGAGT
ACAGCCCAGCAACTGGGCAAAAGCGGCTGACGAGAACAAGATAGAGAACGAGGAATGACG
AGACACAGATAGAAGACAAAGACTGCGGACAGGCAAGTAAGAGAAGGAAAATAAAGCGAG
AGAAGTAGGCCGCCCGAAATGCAAAAGAAAAAGTGACACAGAGAAAATGACCGGCGGGAG
GTAACACGCCCAGGATGACGGAGCACCAATAGAAAAAAACACGTAGGAGAGGGAACATGC
GGACAAGACAATCCCAACCCGAAGATAAACACCGAGAGGTAGACAGCGCAGACTGGAGGA
ACAGCCGTGGAAAGGGAAAGGTACGCAAACGGACCTAAAAAAAACAAAGTCAGGGAAAAA
GGCTAACGGAACAAAGCTGGCCATGG (SEQ ID NO:31)

Fig. 11B

16 space
GAATTCTCTAGAGTGCACGGATCCCTCGAGGGTACCAACCATGGAAGCTAGCAAGCATGC
GAGGAAAGCAAGGAAAATGAAGAACGAAGCGGGTCGAACAGGGAAGACATAAAAAACAGG
CACCATGACACCAACGCGGAATGACACAACACAAAGGTAGCGAGGCACGCACGTAAGAGG
CACAAGAAATGAAAGAAAAAGAGAATACGCAGAGAGGGCAGTAAGGCAGGGAAACGATGA
GCAGACGACGGGATGCTAGCAGCGAAAGCTGAGAAGAAGAGACCCTCAAAAAGCAAAAGA
ATAAGAAAGCCAAAGCATAAAAGAAAAGCGCAATCAAGGAAACGGGCGCTAGAAGACCGA
GACAGTGAGACGAGCACACGCTAAAAAAGAGAGACAATCCAGAAAGAAGACAGTGGACAA
GAGACCGGGTAGCACCAGAGGACAATGAAGGCGGGACGGCATAAACGCCCAAACGGGTAA
GACGGGCCAACGATAAAGGAAGACGAAGGTCAACGCAGAAGGGAATCCAGAAACACAGAC
ATAAAGAAAAAAAGAAATGGCAGCCGGAGAAGCTGAGACGGGACCGCAGTGCGAGAGAAG
AGACGTGCGGAAAAGAGAAGGTCGCGCAAGACGGGCGTGGACCGGACAAAGGATGGGAAA
ACGACCGGATGGAGAGCGCCCAGAGTCAGAAACGGAAGAGATGAAACCCAGAAAGACTCG
CCACAAGAAGGAGTCGGGAAACACAAGAATAAAGCAGCTGGGGAATAGCGGACGAACGGA
ATAGAGGCCCAAAGAACTGGGAGAGGACAGCCGTACAGGAGGAACGGGATAGCGAAGAAC
CAACGTGCGAAAAGACCGGCATAAAACAGAAAGGCAATAGCAGACAGCAAAAATAGAGAG
ACAACGACGTAGAAAGAGGGAAACGTCGCAAAAAACCGGGCTAGAGGAGGACCAACATAG
CGAGACACCAAGATGAAGCAACGGAGAAGTCACACAAAGAGACAGTCGAAAAGCAAAGAA
ATAGCCCAGCAAGCGAATACCCAACAAGAAGAGTCAACAGGAGAAAGAGTCCAAGGAGAA
GCAAGTACACAAGACAAAAGGTAGCAGACACAAGCAATGCACGGGCAGGGAAATGCGAAA
CAGAGAGGATAAGAAGATCTAAAATGCATGGTCTGTGTGATGTTGGTCTGTGTGATGTTG
GTCTGTGTGATGTTGGTCTGTGTGATGTTCTGCAGAAGCTT (SEQ ID NO:32)

Fig. 12A

24 space
GGATCCGACGGGAACAAAGAGAAAGCACAAGTAAAAGGCAACGACGCGCACGAGGTCAGA
ACGCAAACAGGAAGAAGAATGCAACAAAGGAGCGCCGAACGGATACGCGGGCCAACACGA
AGAGGAATGAAAGGGAAACGAAACAAAAAAGTGAAGAGGCCAAAAGAGCACAGCATGGAG
GAAGCCACGGCCGAAAAACTACACCGGGAAGGACCAAACGCGATGGCAGACAGAGCGCAG
ACAGGGATAGAGCCACCCAGGAAGCACGCAGTCAGGGAGAAAAGGGCACAGACACTACGA
AAAAGGGCGACAAGAGGGCTGGGAGAGGGAACGGGCAGAAACATAAAACCCAAGAGCCGA
CCAGAAGTAAAAGGCGATATCAACACAGACGTAAAGCAAGCAGAACAAGAGCACATAAGC
AAGAAGGAGAGGAGACACCTACCAGAGAGAAAAACCCGAACCGTGCGGAAAGGCGGGCGA
GAAGGGATAAAAGAGCACGAACCCAAGAGGATGAAAGGACAAGAGAGAACGAAAGTCCAA
CACAGAAAGGCCAAAGGAATAAAAGCAACAGCCAAAAAAAAGTAAGAAAGCAAGACAAA
GCGAGAATGAAAAGCGAAGGCACAAAAGAAATAGACAGAGGGAACAGCGGAAAGATCCCA
CGGGCGACAGCAACCGGACTCCACGGGAACACGAGGAGAAACGTGAAAACCGAGCGGCAA
CCCAGACTCAGCGGAACAGAAGACAAAAAAATACGGGCAGGGCGAGGAAAGAAAATAGGG
CCAACAAAAAGGAAGCAGATGAAAAACACAAAAACCCACCACATCACGCGGGCCGAGAGC
AGCAACGTGGCAGCACGAGGAGGAGGAGCCCTAGAACGCAAAGGCGAAAAGACGCTGCGA
GGTACCGGGCCAAAGAAAATAAAGGAACGCAAACAAAGGAGCATCAAAGGGAAGAAACAA
AAGAAAATAAAAAAGGAGAAGAAAGGGAAGATAAAAGGAAACGGAAAAAAGAAACTCGCG
ACAAAGACGGCAGCAAAGGTAGAGGAAAAGGAAGAGGACACACTGAAAGAGCACCAGGAG
AAAGACCTAGCAGAAGCACGCTCGAG (SEQ ID NO:33)

Fig. 12B

STABLE NANOREPORTERS

CROSS-REFERENCE TO RELATED APPLICATIONS

This application is a continuation of U.S. patent application Ser. No. 13/957,029, filed Aug. 1, 2013. U.S. patent application Ser. No. 13/957,029 is a continuation of U.S. patent application Ser. No. 12/541,131, filed Aug. 13, 2009, which issued as U.S. Pat. No. 8,519,115 on Aug. 27, 2013. U.S. patent application Ser. No. 12/541,131 claims priority to and the benefit of U.S. Provisional Application No. 61/088,988, filed Aug. 14, 2008. Each of the above-mentioned applications is incorporated herein by reference in its entirety.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Mar. 24, 2016, is named NATE-006C02US_ST25.txt and is 53 KB in size.

BACKGROUND OF THE INVENTION

Although all cells in the human body contain the same genetic material, the same genes are not active in all of those cells. Alterations in gene expression patterns can have profound effects on biological functions. These variations in gene expression can be at the core of altered physiologic and pathologic processes. Therefore, identifying and quantifying the expression of genes in cells can aid the discovery of new therapeutic and diagnostic targets.

To date there are several techniques available that allow the detection of the expression level of multiple genes in a complex sample at one time. Most of these technologies employ, DNA microarrays, devices that consist of thousands of immobilized DNA sequences present on a miniaturized surface that have made this process more efficient. Unfortunately, despite the miniaturization of array formats, this method still requires significant amounts of the biological sample. However, in several cases, such as biopsies of diseased tissues or samples of a discrete cell type, the biological sample is in limited supply. In addition, the kinetics of hybridization on the surface of a microarray is less efficient than hybridization in small amounts of aqueous solution. Moreover, while methods exist to estimate the amount of nucleic acid present in a sample based on microarray hybridization result, microarray technology thus far does not allow for detection of target molecules on an individual level, nor are there microarray-based methods for directly quantifying the amount of target molecule in a given sample.

Thus, there exists a need for accurate and sensitive detection, identification and quantification of target molecules in complex mixtures.

SUMMARY OF THE INVENTION

This invention relates generally to the field of detection, identification, and quantification of target molecules in a sample. The present invention relates in part to improved, stable nanoreporters, and populations of these nanoreporters, based in part on certain design features in the polynucleotide sequences of the nanoreporter backbones and complementary polynucleotide sequences attached thereto.

In some embodiments, the invention provides a population of uniquely labeled nanoreporter probes, where each nanoreporter probe comprises: i) a unique target-specific region; and ii) a region comprising a unique, designed nanoreporter wherein the nanoreporter comprises a single-stranded nucleic acid backbone, the backbone comprising a plurality of label attachment regions covalently attached together in a unique linear combination, where the label attachment regions are selected from a population of designed polynucleotide sequences, where each polynucleotide sequence is hybridized to a complementary polynucleotide sequence having attached thereto one or more detectable molecules; where each complementary polynucleotide sequence has designated a specific detectable molecule; and where each nanoreporter has a detectable signal that distinguishes it from other nanoreporters in said population. In some embodiments, each label attachment region of each backbone is different from the other label attachment regions in that same backbone. In some embodiments, each of the nanoreporter probes further comprises a constant region, wherein the constant region comprises a plurality of repeat nucleotide sequences. The population of nanoreporter probes can comprise two or more nanoreporter probes.

In some embodiments, the invention provides methods for determining the presence of at least one target molecule in a sample, comprising: (1) forming at least one molecular complex comprising: (a) at least one target molecule, and (b) at least one probe comprising a unique target-specific region and a region comprising a unique, designed nanoreporter, wherein said nanoreporter comprises a single-stranded nucleic acid backbone, the backbone comprising a plurality of label attachment regions covalently attached together in a unique linear combination, wherein each label attachment region is hybridized to a complementary polynucleotide sequence having attached thereto one or more detectable molecules, wherein each complementary polynucleotide sequence has designated a specific detectable molecule; and individually counting the presence of one or more molecular complex or at least part of the at least one molecular complex to determine the presence of said at least one target molecule in the sample. In some embodiments, the percentage of valid molecular counts of the molecular complex is higher that about 12.5%. In some embodiments, the numbers of counts is at least two fold higher than the counts obtain when using a nanoreporter probe comprising M13 DNA. A nanoreporter comprising M13 DNA can comprises a single-stranded backbone comprising a plurality of M13 DNA regions covalently attached together wherein each region is hybridized to a complementary polynucleotide sequence having attached thereto one or more detectable molecules.

In some embodiments of the methods and composition of the invention, the numbers of counts above background of each of the molecular complex after normalization of the sample is at least two fold higher when compared to a nanoreporter probe comprising M13 DNA. In some embodiments, the Tm of the complementary polynucleotide sequences when hybridized to its label attachment regions is about 80° C. or higher. In some embodiments, the melting temperature (Tm) of the complementary polynucleotide sequences when hybridized to its label attachment regions is higher than the Tm of polynucleotide sequences complementary to M13 DNA when hybridized to the nanoreporter probe comprising M13 DNA.

In some embodiments, the methods of the invention further comprise determining the presence of a plurality of target molecules by a method comprising forming a plurality molecular complexes, each complex comprising (a) at least one target molecule and (b) at least one probe comprising a unique target-specific region and a region comprising a unique, designed nanoreporter, wherein each nanoreporter comprises a single-stranded nucleic acid backbone, the backbone comprising a plurality of label attachment regions covalently attached together in a unique linear combination, wherein each label attachment region is hybridized to a complementary polynucleotide sequence having attached thereto one or more detectable molecules, and wherein each probe comprises a different nanoreporter region. In some embodiments, the presence of at least 5, 10, 20, 30, 50, 100, 200, 300, or 500 different target molecules is determined. In some embodiments, the target molecule is a nucleic acid. In some embodiments, the nucleic acid comprises at least one heritable mutation, at least one somatic mutation, at least one single nucleotide polymorphism (SNP), at least one point mutation, at least one deletion mutation, at least one insertion mutation, at least one chromosomal translocation, or combinations thereof. In some embodiments, the target molecule is a diagnostic indicator.

In some embodiments, the invention provides, a uniquely labeled nanoreporter probe comprising: i) a unique target-specific region; and ii) a region comprising a plurality of designed label attachment regions covalently attached together in a linear combination, wherein each label attachment region comprises about 800 to 1300 nucleotide bases and has a G/C content of about 50%, wherein each selected label attachment region is different from the other selected label attachment regions, and wherein each label attachment region is hybridized to a complementary polynucleotide sequence having attached thereto one or more detectable molecules, wherein the complementary polynucleotide sequence has a G/C ratio of at least 1/1. In some embodiments, the complementary polynucleotide sequence has a G/C ratio of about 3/2. In some embodiments, the nanoreporter probe further comprises a constant region, where the constant region comprises a plurality of repeat nucleotide sequences.

In some embodiments of the methods and compositions of the invention, the label attachment region comprises about 800 to 1300 nucleotide bases and has a G/C content of about 50% and the complementary polynucleotide sequence has a G/C ratio of about 1/1. In some embodiments, the complementary polynucleotide sequence has a G/C ratio of about 3/2. Examples of templates that can be used to generate the label attachments regions described herein include, but are not limited to, sequences selected from the group consisting of SEQ ID NOS: 1, 2, 3, 4, 5, 6, 7, 8, 9, 10, 11, 12, 13, 14, 15, 16, 17, 18, 19, 20, 21, 22, 23, and 24.

In some embodiments of the methods and compositions of the invention, the label attachment regions comprise a similar adenine content. In some embodiments, the adenine bases are spaced at least an average of every 8 to 16 nucleotide bases. In some embodiments, the label attachment regions comprise a regularly repeated pattern of adenine bases. In some embodiments, the adenine bases are spaced about every 8 to 16 nucleotide bases. In some embodiments, the label attachment regions comprise a thymine content of about 35-45%.

In some embodiments of the methods and compositions of the invention, the complementary polynucleotide sequence comprises a RNA polynucleotide sequence. The RNA polynucleotide sequence can comprises at least one amino-allyl modified uracil base. In some embodiments, the detectable molecule in the complementary polynucleotide sequence is attached to the amino-allyl modified uracil base. In some embodiments, the RNA polynucleotide sequence comprises a plurality of amino-allyl modified uracil bases that are spaced at about an average of every 8 to 16 bases in said RNA polynucleotide sequence. In some embodiments, the detectable molecule is attached to each of the allyl modified uracil bases.

In some embodiments of the compositions and methods of the invention, the detectable molecules are fluorescent dyes.

In some embodiments, the invention provides methods for preparing at least one uniquely labeled nanoreporter comprising: i) combining a plurality of label attachment region each comprising about 800 to 1300 nucleotide bases and a G/C content of about 50%, wherein each selected label attachment region is different from the other selected label attachment regions, ii) covalently attaching the plurality of label attachment regions to each other in linear combination; and iii) hybridizing a complementary polynucleotide sequence to said label attachment region, wherein said complementary polynucleotide sequence is having attached thereto one or more detectable molecules. In some embodiments, the methods further comprise preparing a labeled nanoreporter probe by attaching the labeled nanoreporter to a target specific region. In some embodiments, the complementary polynucleotide sequence has a G/C ratio of at least 1/1.

In some embodiments, the invention provides kits for preparing at least one uniquely labeled nanoreporter comprising: a) at least three label attachment regions each comprising about 800 to 1300 nucleotide bases, a G/C content of about 50%; and b) at least three complementary polynucleotide sequences having attached thereto a detectable molecule, wherein the complementary polynucleotide sequences has a G/C ratio of at least 1/1. In some embodiments, the kits further comprise at least three target specific probes.

In some embodiments, the invention provides kits comprising a population of nanoreporters as described herein and instructions for its use.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A to FIG. 2E: FIG. 2A is a schematic illustration of the experiment shown in FIG. 2B and FIG. 2C. In this case, the diamond represents biotin that was used to attach the complex by one end to the surface prior to stretching. FIG. 2B and FIG. 2C show images from experiments in which S2-A capture probe, S2-B labeled nanoreporter and S2 target DNA (FIG. 2B) or S2 target RNA (FIG. 2C) were hybridized. FIG. 2E shows a close-up of nanoreporter complexes from FIG. 2B, each containing S2-A capture probe, S2-B labeled nanoreporter and S2 target DNA. FIG. 2D shows an image of a negative control experiment, in which S2-A capture probe, S2-B labeled nanoreporter and no S2 target RNA were hybridized.

In FIG. 3, the labeled nanoreporter is immobilized through the binding of A1 to an immobilized affinity partner. The other end of the nanoreporter is in solution (FIG. 3A), but can be immobilized by hybridization to a complementary oligonucleotide which contains another affinity tag (A2) used to immobilize the nanoreporter (FIG. 3B). A1 and A2 can be the same, for example biotin, for immobilization on an avidin- or streptavidin-coated surface. Upon immobilization of A1, the nanoreporter can be stretched, or "elongated" as depicted in FIG. 3, for example by electrostretching, for separation of the label attachment regions in a manner that permits detection of the nanoreporter code. Optionally, while the nanoreporter is in an elongated state, A2 is introduced and binds the end of the nanoreporter that is complementary to A2 down to the surface.

FIG. 4A illustrates immobilization of one terminus of a DNA molecule in a microfluidic device; FIG. 4B illustrates extension of the DNA in an electric field; and FIG. 4C illustrates selective immobilization of a second terminus of the extended DNA molecule by affinity tags introduced into the device following elongation.

FIG. 9 shows the polynucleotide sequence of a plasmid vector that may be utilized to clone, propagate, and generate the single stranded nanoreporter backbones of the present invention.

FIG. 10A and FIG. 10B show the polynucleotide sequences of two templates that were utilized in the dye optimization experiments to generate single-stranded nanoreporter backbones (see Example 6). In these template sequences, the regularly-repeated base is thymine, which upon transcription produces a complementary single-stranded nanoreporter backbone having adenine as the regularly-repeated base. FIG. 10A shows the polynucleotide sequence of a template having regularly-repeated base at about every 8 nucleotides. FIG. 10B shows the polynucleotide sequence of a template having a regularly-repeated base at about every 10 nucleotides.

FIG. 11A and FIG. 11B show the polynucleotide sequences of two templates that were utilized in the dye optimization experiments to generate single-stranded nanoreporter backbones (see Example 6). FIG. 11A shows the polynucleotide sequence of a template having regularly-repeated base at about every 12 nucleotides. FIG. 11B shows the polynucleotide sequence of a template having a regularly-repeated base at about every 14 nucleotides.

FIG. 12A and FIG. 12B show the polynucleotide sequences of two templates that were utilized in the dye optimization experiments to generate single-stranded nanoreporter backbones (see Example 6). FIG. 12A shows the polynucleotide sequence of a template having regularly-repeated base at about every 16 nucleotides. FIG. 12B shows the polynucleotide sequence of a template having a regularly-repeated base at about every 24 nucleotides.

DETAILED DESCRIPTION OF THE INVENTION

Figure 1:
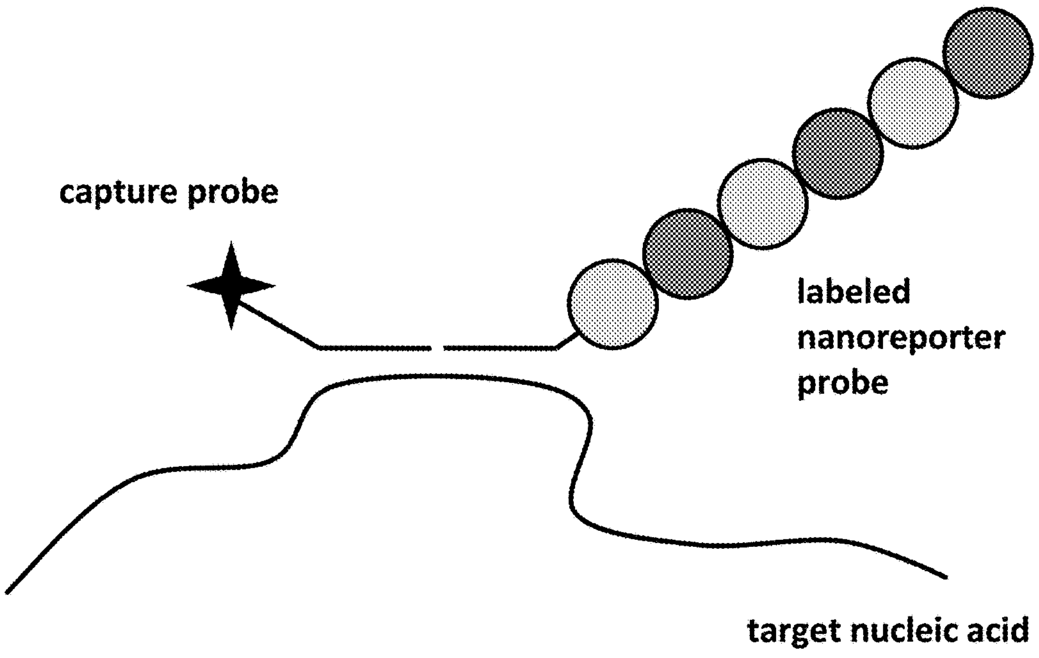
FIG. 1 is a schematic illustration of a dual nanoreporter with a 6-position nanoreporter code, using a capture probe and a single 6-position nanoreporter component. The arrow is illustrative of an affinity tag, which is optionally included and which can be used to purify the nanoreporter or immobilize the nanoreporter (or nanoreporter-target molecule complex) for the purpose of imaging.

The present invention provides compositions and methods for detection and quantification of individual target molecules in biomolecular samples. In particular, the invention provides stable nanoreporters that are capable of binding individual target molecules, and provide improved detection of target molecules. Through nanoreporters' label codes, the binding of the nanoreporter probes to target molecules results in the identification of the target molecules. Methods of making and using such nanoreporters are also provided. The nanoreporters can be used in a wide variety of applications such as diagnostic, prognostic, quality control and screening applications.

Certain aspects of the present invention relate to the selection of a library or population of designed (e.g., synthetic sequences) nanoreporters. More specifically, certain optimized sequence characteristics provide improved molecular stability of a nanoreporter, as well as improved detection when the nanoreporter is combined with a target-specific sequence. For instance, the methods and compositions of the invention provide nanoreporters comprising unique synthetic backbones that do not produce a secondary structure and produce consistent brightness.

In some embodiments, the present invention provides a population of designed (e.g. synthetic) nanoreporter wherein said nanoreporter comprises a plurality of different detectable molecules, and wherein the plurality of different detectable molecules in each nanoreporter has a detectable signal that distinguishes it from other nanoreporters in said population. Thus, in some embodiments the present invention provides a population of designed nanoreporters with improved molecular stability, wherein each nanoreporter in the population has a detectable signal that distinguishes it from other nanoreporters in said population.

In some embodiments, the invention provides nanoreporters comprising unique designed backbones (e.g. synthetic) hybridized to a unique complementary polynucleotide sequence having attached thereto a detectable label. Each nanoreporter will generate a unique signal that will not change during the course of a detection assay. That is the unique and distinguishable signal or signal code associated with the nanoreporter will remain the same during the course of a detection assay. In some embodiments, the complementary polynucleotide sequence having attached thereto the detectable label can be an in-vitro transcribed, dye-coupled RNA segments having consistent brightness. Consistent brightness as described herein refers to the strength, size and/or intensity of the signal produced by the dye-coupled RNA segments. That is, in some embodiments, the strength, size and/or intensity of the signal of the dye will be similar among dye-coupled RNA segments that have the same dye attached thereto. For example, dye-coupled RNA segments that have a color green dye attached thereto will have similar a signal or a signal with same intensity and/or brightness. This is useful, among other things, because it allows an image analysis software/algorithm or user to define what a spot of a particular color should look like in term of brightness and size. In addition, several of the dyes might bleed to the channels of the other dyes, if the strength of a signal is consistent, then the bleed through signal will also be consistent, thus, allowing for the bleed through to be ignored. Furthermore, noises in the images that do not fall within the spot parameters can be disregarded. As a result, for example, one can narrowly define the parameters associated with the nanoreporters' signals allowing the software/algorithm or user to disregard a higher percentage of the noise. These provide for more robust and reliable readings.

In some embodiments, the nanoreporters comprise a backbone with an arrangement of nucleotide-based label attachment regions, wherein each label attachment region has have a specific sequence designated for a specific label. In this system, the unique sequence of the backbone dictates the color code of the nanoreporter. Each backbone will anneal only to the polynucleotide sequence complementary to its sequence, each of which has a specific, designated label (e.g. color). Thus, each backbone will generate only the designated code, e.g., even if the polynucleotide sequence detach from the backbone during the detection process. If the polynucleotide sequence in the nanoreporter detach during synthesis or during a hybridization procedure, they can only be replaced with polynucleotide sequence of the same color, eliminating the potential for shared or swapped labels. The complementary polynucleotide sequence having attached thereto the detectable label can be an in-vitro transcribed, dye-coupled RNA segments. In some embodiments, in constructing a given nanoreporter backbone from a library of individually unique polynucleotide-based label attachment region templates each label attachment region is assigned a detectable label (e.g. a detectable molecule), and each label attachment region within a given backbone is selected to be different from the other label attachment regions in that same backbone.

In some embodiments, the sequences are designed to have an even distribution of one base, allowing for an even distribution of coupled labels (e.g. fluors) when this base is introduced as a modified nucleotide into an in vitro polymerized RNA or DNA. In some embodiments, the sequences are designed without significant direct or inverted repeats to make the nanoreporters as unstructured and unique as possible. In some embodiments, the sequences are designed without any direct or inverted repeat of 9 nucleotides or greater across a sequence that 1100 base pairs in length. In some embodiments, the sequences are designed without any direct or inverted repeat of 7 nucleotides or greater across any 100 base pair region. In some embodiments, the label attachment regions and/or the complementary polynucleotide sequence comprise a particular G/C content and ratio.

Examples of polynucleotide templates that may be utilized to generate these designed label attachment regions are set forth in the polynucleotide sequences of SEQ ID NOS: 1, 2, 3, 4, 5, 6, 7, 8, 9, 10, 11, 12, 13, 14, 15, 16, 17, 18, 19, 20, 21, 22, 23, and 24.

Accordingly, certain aspects of the present invention provide a population of unique nanoreporters or nanoreporter probes, each comprised of a unique polynucleotide-based backbone, wherein each nanoreporter in the population is not only distinct from the other nanoreporters in the population but also has improved molecular stability and a detectable signal that distinguishes it from other nanoreporters in said population. In some embodiments each nanoreporter probe comprises a plurality of individual, designed label attachment regions. In some embodiments, each of the label attachment regions is different from the other label attachment regions in that same nanoreporter. Thus, in certain aspects the invention provides a more stable population of unique nanoreporters having improved detection properties. An exemplary nanoreporter having such characteristics is described herein, referred to as the DV1 nanoreporter.

Nanoreporters

A fully assembled and labeled nanoreporter probe comprises two main portions, a target-specific sequence that is capable of binding to a target molecule, and a labeled nanoreporter which provides a "code" of signals (the "nanoreporter code") associated with the target-specific sequence. Upon binding of the nanoreporter probe to the target molecule, the nanoreporter code identifies the target molecule to which the nanoreporter is bound.

Nanoreporters are modular structures. In some embodiments, the nanoreporter comprises a plurality of different detectable molecules. In some embodiments, a labeled nanoreporter, is a molecular entity containing certain basic elements: (i) a plurality of unique label attachment regions attached in a particular, unique linear combination, and (ii) complementary polynucleotide sequences attached to the label attachment regions of the backbone. In some embodiments, the labeled nanoreporter comprises 2, 3, 4, 5, 6, 7, 8, 9, 10 or more unique label attachment regions attached in a particular, unique linear combination, and complementary polynucleotide sequences attached to the label attachment regions of the backbone. In some embodiments, the labeled nanoreporter comprises 3 or more unique label attachment regions attached in a particular, unique linear combination, and complementary polynucleotide sequences attached to the label attachment regions of the backbone. In some embodiments, the labeled nanoreporter comprises 6 or more unique label attachment regions attached in a particular, unique linear combination, and complementary polynucleotide sequences attached to the label attachment regions of the backbone. A nanoreporter probe further comprises a target-specific sequence, also attached to the backbone.

The term label attachment region includes a region of defined polynucleotide sequence within a given backbone that may serve as an individual attachment point for a detectable molecule. In some embodiments, the label attachment regions comprise designed sequences. Specific examples of defined polynucleotide template sequences that may be utilized to generate single stranded label attachment regions include the template sequences set forth in SEQ ID NOS: 1, 2, 3, 4, 5, 6, 7, 8, 9, 10, 11, 12, 13, 14, 15, 16, 17, 18, 19, 20, 21, 22, 23, and 24, in addition to suitable variants thereof (e.g., sequences having 60%, 70%, 80%, 90%, 95%, 98%, or more, including all integers in between, sequence identity). Transcription of the template sequences of SEQ ID NOS: 1-24 generates single stranded label attachment regions having a polynucleotide sequence that is complementary to the sequences of SEQ ID NOS:1-24.

In some embodiments, the label nanoreporter also comprises a backbone containing a constant region. The term constant region includes tandemly-repeated sequences of about 10 to about 25 nucleotides that are covalently attached to a nanoreporter. The constant region can be attached at either the 5' region or the 3' region of a nanoreporter, and may be utilized for capture and immobilization of a nanoreporter for imaging or detection, such as by attaching to a solid substrate a sequence that is complementary to the constant region. In certain aspects, the constant region contains 2, 3, 4, 5, 6, 7, 8, 9, 10, or more tandemly-repeated sequences, wherein the repeat sequences each comprise about 8, 9, 10, 11, 12, 13, 14, 15, 16, 17, 18, 19, 20, 21, 22, 23, 24, 25, 26, 27, 28, 29, 30, or more nucleotides, including about 12-18, 13-17, or about 14-16 nucleotides.

The nanoreporters described herein comprise synthetic, designed sequences. In some embodiments, the nanoreporters described herein provide improved consistency in the label brightness. Consistent brightness as described herein refers to the strength, size and/or the intensity of the signal produced by the labeled segments. That is, in some embodiments, the strength, size and/or intensity of the signal of the labeled segments will be similar among the segments that have the same label attached thereto. As described above, this improved consistency leads to more robust data. In some embodiments, a nucleotide is spaced at least an average of 8, 9, 10, 12, 15, 16, 20, 30, or 50 bases apart. In some embodiments, a nucleotide is spaced at least an average of 8 to 16 bases apart. In some embodiments, a nucleotide is spaced at least an average of 8 bases apart. In some embodiments, the sequences contain a fairly regularly-spaced pattern of a nucleotide (e.g. adenine) residue in the backbone. This allows for a regularly spaced complementary nucleotide in the complementary polynucleotide sequence having attached thereto a detectable molecule. For example, in some embodiments, when the nanoreporter sequences contain a fairly regularly-spaced pattern of adenine residues in the backbone, whose complement is a regularly-spaced pattern of uridine (U) residues in complementary RNA segments, the in vitro transcription of the segments can be done using an aminoallyl-modified uridine base, which allows the covalent amine coupling of dye molecules at regular intervals along the segment. In some embodiments, the sequences contain about the same number or percentage of a nucleotide (e.g. adenine) that is spaced at least an average of 8, 9, 10, 12, 15, 16, 20, 30, or 50 bases apart in the sequences. This allows for similar number or percentages in the complementary polynucleotide sequence having attached thereto a detectable molecule. Thus, in some embodiments, the sequences contain a nucleotides that is not regularly-spaced but that is spaced at least an average of 8, 9, 10, 12, 15, 16, 20, 30, or 50 bases apart, the number of nucleotides in the sequences can vary depending of the desired brightness for the nanoreporter. In some embodiments, 20%, 30%, 50%, 60%, 70%, 80%, 90% or 100% of the complementary nucleotide is coupled to a detectable molecule. For instance, in some embodiments, when the nanoreporter sequences contain a similar percentage of adenine residues in the backbone and the in vitro transcription of the complementary segments is done using an aminoallyl-modified uridine base, 20%, 30%, 50%, 60%, 70%, 80%, 90% or 100% of the aminoallyl-modified uridine base can be coupled to a detectable molecule. Alternatively, the ratio of aminoallyl-modified uridine bases and uridine bases can be changed during the in vitro transcription process to achieve the desired brightness. For example, in vitro transcription process can take place in the presence of a mixture with a ratio of 1/1 of uridine to aminoallyl-modified uridine bases, when some or all the aminoallyl-modified uridine bases can be coupled to a detectable molecule. Thus, a person of ordinary skill in the art will understand that there are several methods in which consistent brightness among the nanoreporters can be achieved.

In some embodiments, the nanoreporters described herein have a fairly consistent melting temperature (Tm). In some embodiments, the Tm of the complementary polynucleotide sequences when hybridized to its label attachment regions in the nanoreporters described herein are higher than the Tm of a polynucleotide sequences complementary to a M13 DNA template when hybridized to a nanoreporter probe comprising the M13 DNA. Without intending to be limited to any theory, the Tm of the nanoreporters described herein provides for stronger bonds between the nanoreporter backbone and the complementary polynucleotide sequence having attached thereto a detectable molecule, therefore, preventing dissociation during synthesis and hybridization procedures. In addition, the consistent Tm among a population of nanoreporters allows for the synthesis and hybridization procedures to be tightly optimized, as the optimal conditions are the same for all spots and positions. In some embodiments, the sequences of the nanoreporters have a 50% guanine/cytosine (G/C), with no more than three G's in a row. Thus, in some embodiments, the invention provides a population of nanoreporters in which the Tm among the nanoreporters in the population is fairly consistent. In some embodiments, the invention provides a population of nanoreporters in which the Tm of the complementary polynucleotide sequences when hybridized to its label attachment regions is about 80° C., 85° C., 90° C., 100° C. or higher. In some embodiments, the invention provides a population of nanoreporters in which the Tm of the complementary polynucleotide sequences when hybridized to its label attachment regions is about 80° C. or higher.

In some embodiments, the nanoreporters described herein have minimal or no secondary structures, such as any stable intra-molecular base-paring interaction (e.g. hairpins). Without intending to be limited to any theory, the minimal secondary structure in the nanoreporters provides for better hybridization between the nanoreporter backbone and the polynucleotide sequence having attached thereto a detectable molecule. In addition, the minimal secondary structure in the nanoreporters provides for better detection of the detectable molecules in the nanoreporters. In some embodiments, the nanoreporters described herein have no significant intra-molecular pairing under annealing conditions of 75° C., 1×SSPE. Secondary structures can be predicted by programs known in the art such as MFOLD. In some embodiments, the nanoreporters described herein contain less than 1% of inverted repeats in each strand, wherein the inverted repeats are 9 bases or greater. In some embodiments, the nanoreporters described herein contain no inverted repeats in each strand. In some embodiments, the nanoreporters do not contain any inverted repeat of 9 nucleotides or greater across a sequence that is 1100 base pairs in length. In some embodiments, the nanoreporters do not contain any inverted repeat of 7 nucleotides or greater across any 100 base pair region. In some embodiments, the nanoreporters described herein contain less than 1% of inverted repeats in each strand, wherein the inverted repeats are 9 nucleotides or greater across a sequence that 1100 base pairs in length. In some embodiments, the nanoreporters described herein contain less than 1% of inverted repeats in each strand, wherein the inverted repeats are 7 nucleotides or greater across any 100 base pair region. In some embodiments, the nanoreporters described herein contain a skewed strand specific content such that one strand is CT-rich and the other is GA rich.

The invention provides unique nanoreporters. In some embodiments, the nanoreporters described herein contain less than 1% of direct repeats. In some embodiments, the nanoreporters described herein contain no direct repeats. In some embodiments, the nanoreporters do not contain any direct repeat of 9 nucleotides or greater across a sequence that 1100 base pairs in length. In some embodiments, the labeled nanoreporters do not contain any direct repeat of 7 nucleotides or greater across any 100 base pair region. In some embodiments, the nanoreporters described herein contain less than 1% of direct repeats in each strand, wherein the direct repeats are 9 nucleotides or greater across a sequence that 1100 base pairs in length. In some embodiments, the nanoreporters described herein contain less than 1% of direct repeats in each strand, wherein the direct repeats are 7 nucleotides or greater across any 100 base pair region. In some embodiments, the nanoreporters described herein contain less than 85, 80, 70, 60, 50, 40, 30, 20, 10, or 5% homology to any other sequence used in the backbones or to any sequence described in the REFSEQ public database. In some embodiments, the nanoreporters described herein contain less than 85, % homology to any other sequence used in the backbones or to any sequence described in the REFSEQ public database. In some embodiments, the nanoreporters described herein contain less than 20, 16, 15, 10, 9, 7, 5, 3, 2 contiguous bases of homology to any other sequence used in the backbones or to any sequence described in the REFSEQ public database. In some embodiments, the nanoreporters described herein have no more than 15 contiguous bases of homology and no more than 85% identity across the entire length of the nanoreporter to any other sequence used in the backbones or to any sequence described in the REFSEQ public database.

In some embodiments, the sequence characteristics of the nanoreporter probes described herein provide improved detection of a target molecule. For instance, the binding of the nanoreporter probes to target molecules which results in the identification of the target molecules can be performed by individually detecting the presence of the nanoreporter. This can be performed by individually counting the presence of one or more of the nanoreporter molecules in a sample. In some embodiments where such counting methods are used, the nanoreporter probes described herein allow for an increased in the number of counts. In some embodiments, the number of molecular counts above background of said molecular complex after normalization of the sample is higher than 300, 400, 450, 500, 600, 700, 800, 900 or 1000 molecular counts. In some embodiments, the number of molecular counts above background of said molecular complex after normalization of the sample is higher than 400 molecular counts. In some embodiments, the percentage of valid molecular counts of the nanoreporter probes described herein is higher that about 10, 11, 12, 12.5, 14, 15, 20, 25, 30, 35, 40, 50, 60, 70, 80 or 90%. In some embodiments, the percentage of valid molecular counts of the nanoreporter probes described herein is higher that about 10%. In some embodiments, the percentage of valid molecular counts of the nanoreporter probes described herein is higher that about 12.5%. In some embodiments, the number of molecular counts above background of the nanoreporter described herein after normalization of said sample is at least 2, 3, 5, 6, 10, 20, 30, 40, 50, 60, 70, 80, 90 or 100 fold higher than a comparable nanoreporter probe comprising M13 DNA. A comparable nanoreporter comprising M13 DNA is a nanoreporter comprising the same target specific region attached to a M13 DNA backbone. Examples of comparable nanoreporter probes comprising M13 DNA are described in the Examples section. In some embodiments, the number of molecular counts above background of the nanoreporter described herein after normalization of said sample is at least 2 fold higher than a comparable nanoreporter comprising M13 DNA. In some embodiments, the number of molecular counts above background of the nanoreporter described herein after normalization of said sample is at least 6 fold higher than a comparable nanoreporter comprising M13 DNA. In some embodiments, the number of molecular counts above background of the nanoreporter described herein after normalization of said sample is at least 20 fold higher than a comparable nanoreporter comprising M13 DNA. In some embodiments, the number of molecular counts above background of the nanoreporter described herein after normalization of said sample is at least 100 fold higher than a comparable nanoreporter comprising M13 DNA.

The elements of a nanoreporter can be found in a single molecular entity (a "singular" nanoreporter), or two distinct molecular entities (a "dual" nanoreporter). Each molecular entity may be composed of one molecule or more than one molecule attached to one another by covalent or non-covalent means. In some embodiments, each component of a dual nanoreporter has a target-specific sequence that binds to a different site on the same target molecule. This allows for smaller nanoreporter components with more efficient kinetics of binding of the nanoreporter to the target molecule and better signal:noise ratios resulting from the greater binding specificity. When using a dual nanoreporter system one of the nanoreporter probes may be unlabeled. In some embodiments, the unlabeled nanoreporter probe may comprise a capture region. In some embodiments, the unlabeled nanoreporter probe may comprise a target-specific region and a backbone that may be single stranded. In some embodiments, the unlabeled nanoreporter probe may comprise a target-specific region and a backbone that may be double stranded.

The complementary polynucleotide sequences attached to a nanoreporter backbone serve to attach detectable molecules, or label monomers, to the nanoreporter backbone. The complementary polynucleotide sequences may be directly labeled, for example, by covalent incorporation of one or more detectable molecules into the complementary polynucleotide sequence. Alternatively, the complementary polynucleotide sequences may be indirectly labeled, such as by incorporation of biotin or other molecule capable of a specific ligand interaction into the complementary polynucleotide sequence. In such instances, the ligand (e.g., streptavidin in the case of biotin incorporation into the complementary polynucleotide sequence) may be covalently attached to the detectable molecule. Where the detectable molecules attached to a label attachment region are not directly incorporated into the complementary polynucleotide sequence, this sequence serves as a bridge between the detectable molecule and the label attachment region, and may be referred to as a bridging molecule, e.g., a bridging nucleic acid.

The nucleic-acid based nanoreporter and nanoreporter-target complexes of the present invention comprise nucleic acids, which may be affinity-purified or immobilized using a nucleic acid, such as an oligonucleotide, that is complementary to the constant region or the nanoreporter or target nucleic acid. As noted above, in some embodiments the nanoreporters comprise at least one constant region, which may serve as an affinity tag for purification and/or for immobilization (for example to a solid surface). The constant region typically comprises two or more tandemly-repeated regions of repeat nucleotides, such as a series of 15-base repeats. In such exemplary embodiments, the nanoreporter, whether complexed to a target molecule or otherwise, can be purified or immobilized by an affinity reagent coated with a 15-base oligonucleotide which is the reverse complement of the repeat unit.

Nanoreporters, or nanoreporter-target molecule complexes, can be purified in two or more affinity selection steps. For example, in a dual nanoreporter, one probe can comprise a first affinity tag and the other probe can comprise a second (different) affinity tag. The probes are mixed with target molecules, and complexes comprising the two probes of the dual nanoreporter are separated from unbound materials (e.g., the target or the individual probes of the nanoreporter) by affinity purification against one or both individual affinity tags. In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from probes comprising the first affinity tag. At this point only full complexes would be bound. The complexes are finally released from the affinity reagent for the second affinity tag and then preferably stretched and imaged. The affinity reagent can be any solid surface coated with a binding partner for the affinity tag, such as a column, bead (e.g., latex or magnetic bead) or slide coated with the binding partner. Immobilizing and stretching nanoreporters using affinity reagents is fully described in U.S. Provisional Application No. 60/753,816 by Sean M. Ferree and Dwayne L. Dunaway, entitled "Compositions Comprising Oriented, Immobilized Macromolecules and Methods for Their Preparation," filed on Dec. 23, 2005, which is incorporated by reference herein in its entirety.

The sequence of signals provided by the label monomers associated with the various label attachment regions of the backbone of a given nanoreporter allows for the unique identification of the nanoreporter. For example, when using fluorescent labels, a nanoreporter having a unique identity or unique spectral signature is associated with a target-specific sequence that recognizes a specific target molecule or a portion thereof. When a nanoreporter is exposed to a mixture containing the target molecule under conditions that permit binding of the target-specific sequence(s) of the nanoreporter to the target molecule, the target-specific sequence(s) preferentially bind(s) to the target molecule. Detection of the nanoreporter signal, such as the spectral code of a fluorescently labeled nanoreporter, associated with the nanoreporter allows detection of the presence of the target molecule in the mixture (qualitative analysis). Counting all the label monomers associated with a given spectral code or signature allows the counting of all the molecules in the mixture associated with the target-specific sequence coupled to the nanoreporter (quantitative analysis). Nanoreporters are thus useful for the diagnosis or prognosis of different biological states (e.g., disease vs. healthy) by quantitative analysis of known biological markers. Moreover, the exquisite sensitivity of single molecule detection and quantification provided by the nanoreporters of the invention allows for the identification of new diagnostic and prognostic markers, including those whose fluctuations among the different biological states is too slight detect a correlation with a particular biological state using traditional molecular methods. The sensitivity of nanoreporter-based molecular detection permits detailed pharmacokinetic analysis of therapeutic and diagnostic agents in small biological samples.

Many nanoreporters, referred to as singular nanoreporters, are composed of one molecular entity. However, to increase the specificity of a nanoreporter and/or to improve the kinetics of its binding to a target molecule, a nanoreporter can be a dual nanoreporter composed of two molecular entities, each containing a different target-specific sequence that binds to a different region of the same target molecule. In a dual nanoreporter, at least one of the two molecular entities is labeled. The other molecular entity need not necessarily be labeled. Such unlabeled components of dual nanoreporters may be used as capture probes (see FIG. 1 and FIG. 2) and optionally have affinity tags attached, such as biotin, which are useful to immobilize and/or stretch the complex containing the dual nanoreporter and the target molecule to allow visualization and/or imaging of the complex. For instance, in some embodiments, a dual nanoreporter with a 6-position nanoreporter code, using one 6-position coded nanoreporter and a capture probe. In some embodiments a dual nanoreporter with a 7-position nanoreporter code can be used, using one 8-position nanoreporter component and one single-position nanoreporter component. In some embodiments, a dual nanoreporter with an 6-position nanoreporter code, using one capture probe with an affinity tag and one 6-position nanoreporter component. In some embodiment an affinity tag is optionally included and can be used to purify the nanoreporter or immobilize the nanoreporter (or nanoreporter-target molecule complex) for the purpose of imaging.

Because of their modular structures, nanoreporters may be assembled and labeled in a variety of different ways. For example, a nanoreporter backbone can be attached to a target-specific sequence (for example by hybridization and, optionally, ligation), and the structure comprising the backbone and target-specific sequence attached to one or more complementary polynucleotide sequences having attached thereto, either directly or indirectly, a detectable molecule. Alternatively, the nanoreporter backbone can first be attached to one or more complementary polynucleotide sequences, and the backbone structure then attached to a target specific sequence. Thus, unless stated otherwise, a discussion or listing of steps in nanoreporter assembly does not imply that a specific route of assembly must be followed.

Nanoreporters' syntheses can be performed by any suitable methods known in the art. Double-stranded plasmids carrying nanoreporter sequences (e.g. DV1 sequences) can be grown in some bacterial strains under conditions of low temperature (no greater than 34° C.). Nanoreporter linear single-stranded backbones can be made from double-stranded plasmid DNA using a four-step protocol that includes linearization with a restriction enzyme, dephosphorylation with a thermolabile phosphatase, digestion with a second restriction enzyme to separate the cloning vector from the backbone sequence, and a strand-specific lambda exonuclease digestion which leaves only one strand of the backbone fragment intact. FIG. 9 shows an example of a vector that by used for nanoreporters' syntheses.

Nanoreporter assembly and use is exemplified herein largely by way of description of a variety of nucleic acid-based nanoreporters. Illustrative embodiments of partially and fully assembled nanoreporters are listed below.

At its simplest, the invention provides a nucleic acid backbone having a plurality (e.g. 3) of label attachment regions that are capable of being labeled and resolved, each of which is made of a rationally-designed nucleotide sequence. These sequences encompass one or more, or all the characteristics described herein that make the nanoreporter more stable. Examples of polynucleotide templates that may be utilized to generate these designed label attachment regions are set forth in the polynucleotide sequences of SEQ ID NOS:1, 2, 3, 4, 5, 6, 7, 8, 9, 10, 11, 12, 13, 14, 15, 16, 17, 18, 19, 20, 21, 22, 23, and 24. The label attachment regions of each individual backbone are arranged in a unique linear order or combination, making each individual backbone unique as compared to the other backbones in a population. Since the individual nanoreporters in a population are each made of a unique backbone, each nanoreporter is similarly unique as compared to the other nanoreporters in a population. In some embodiments, each label attachment region is unique when compared to the other label nanoreporter region in the backbone.

In some embodiments, the nucleotide sequences of the individual label attachment regions within each nanoreporter are different from the nucleotide sequences of the other label attachment regions within that nanoreporter, preventing rearrangements, such recombination, sharing or swapping of the label polynucleotide sequences, and thereby improving the molecular stability. The number of label attachment regions to be formed on a backbone is based on the length and nature of the backbone, the means of labeling the nanoreporter, as well as the type of label monomers providing a signal to be attached to the label attachment regions of the backbone. In some embodiments, the complementary nucleotide sequence of each label attachment region is assigned a specific detectable molecule.

The invention also provides labeled nanoreporters wherein one or more label attachment regions are attached to a corresponding detectable molecule, each detectable molecule providing a signal. For example, in some embodiments, a labeled nanoreporter according to the invention is obtained when at least three detectable molecules are attached to three corresponding label attachment regions of the backbone such that these labeled label attachment regions, or spots, are distinguishable based on their unique linear arrangement. A "spot," in the context of nanoreporter detection, is the aggregate signal detected from the label monomers attached to a single label attachment site on a nanoreporter, and which, depending on the size of the label attachment region and the nature (e.g., primary emission wavelength) of the label monomer, may appear as a single point source of light when visualized under a microscope. Spots from a nanoreporter may be overlapping or non-overlapping. The nanoreporter code that identifies that target molecule can comprise any permutation of the length of a spot, its position relative to other spots, and/or the nature (e.g., primary emission wavelength(s)) of its signal. Generally, for each probe or probe pair of the invention, adjacent label attachment regions are non-overlapping, and/or the spots from adjacent label attachment regions are spatially and/or spectrally distinguishable, at least under the detection conditions (e.g., when the nanoreporter is immobilized, stretched and observed under a microscope, as described in U.S. Application Ser. No. 61/029,220, incorporated herein by reference).

Occasionally, reference is made to a spot size as a certain number of bases or nucleotides. As would be readily understood by one of skill in the art, this refers to the number of bases or nucleotides in the corresponding label attachment region.

The order and nature (e.g., primary emission wavelength(s), optionally also length) of spots from a nanoreporter serve as a nanoreporter code that identifies the target molecule capable of being bound by the nanoreporter through the nanoreporter's target specific sequence(s). When the nanoreporter is bound to a target molecule, the nanoreporter code also identifies the target molecule. Optionally, the length of a spot can be a component of the nanoreporter code.

Detectable molecules providing a signal associated with different label attachment regions of the backbone can provide signals that are indistinguishable under the detections conditions ("like" signals), or can provide signals that are distinguishable, at least under the detection conditions (e.g., when the nanoreporter is immobilized, stretched and observed under a microscope).

The invention also provides a nanoreporter wherein two or more detectable molecules are attached to a label attachment region. The signal provided by the detectable molecules associated with said label attachment region produces an aggregate signal that is detected. The aggregate signal produced may be made up of like signals or made up of at least two distinguishable signals (e.g., spectrally distinguishable signals).

In one embodiment, the invention provides a nanoreporter wherein at least three detectable molecules providing like signals are attached to three corresponding label attachment regions of the backbone and said three detectable molecules are spatially distinguishable. In another embodiment, the invention provides a nanoreporter wherein at least three detectable molecules providing three distinguishable signals are attached to three neighboring label attachment regions, for example three adjacent label attachment regions, whereby said at least three label monomers are spectrally distinguishable.

The invention also provides a nanoreporter wherein the spots providing like or unlike signals are separated by a spacer region, whereby interposing the spacer region allows the generation of dark spots, which expand the possible combination of uniquely detectable signals. The term "dark spot" refers to a lack of signal from a label attachment site on a nanoreporter. Dark spots can be incorporated into the nanoreporter code to add more coding permutations and generate greater nanoreporter diversity in a nanoreporter population. In one embodiment, the spacer regions have a length determined by the resolution of an instrument employed in detecting the nanoreporter.

The invention provides a nanoreporter with one or more "double spots." Each double spot contains two or more (e.g., three, four or five) adjacent spots that provide like signals without being separated by a spacer region. Double spots can be identified by their sizes.

A detectable molecule providing a signal according to the invention may be attached covalently or non-covalently (e.g., via hybridization) to a complementary polynucleotide sequence that is attached to the label attachment region. The label monomers may also be attached indirectly to the complementary polynucleotide sequence, such as by being covalently attached to a ligand molecule (e.g., streptavidin) that is attached through its interaction with a molecule incorporated into the complementary polynucleotide sequence (e.g., biotin incorporated into the complementary polynucleotide sequence), which is in turn attached via hybridization to the backbone.

Certain aspects of the invention also provide a nanoreporter associated with a uniquely detectable signal, such as a spectral code, determined by the sequence of signals provided by the label monomers attached (e.g., indirectly) to label attachment regions on the backbone of the nanoreporter, whereby detection of the signal allows identification of the nanoreporter.

In one embodiment, the invention provides a nanoreporter further comprising an affinity tag attached to the nanoreporter backbone, such that attachment of the affinity tag to a support allows backbone stretching and resolution of signals provided by label monomers corresponding to different label attachment regions on the backbone. Nanoreporter stretching may involve any stretching means known in the art including but not limited to, means involving physical, hydrodynamic or electrical means. The affinity tag may comprise a constant region.

A nanoreporter according to the invention can further include a target-specific sequence coupled to the backbone. The target-specific sequence is selected to allow the nanoreporter to recognize, bind or attach to a target molecule. The nanoreporters of the invention are suitable for identification of target molecules of all types. For example, appropriate target-specific sequences can be coupled to the backbone of the nanoreporter to allow detection of a target molecule. Preferably the target molecule is DNA (including cDNA), RNA (including mRNA and cRNA), a peptide, a polypeptide, or a protein.

One embodiment of the invention provides increased flexibility in target molecule detection with label monomers according to the invention. In this embodiment, a dual nanoreporter comprising two different molecular entities, each with a separate target-specific region, at least one of which is labeled, bind to the same target molecule. Thus, the target-specific sequences of the two components of the dual nanoreporter bind to different portions of a selected target molecule, whereby detection of the spectral code associated with the dual nanoreporter provides detection of the selected target molecule in a biomolecular sample contacted with said dual nanoreporter.

The invention also provides a method of detecting the presence of a specific target molecule in a biomolecular sample comprising: (i) contacting said sample with a nanoreporter as described herein (e.g., a singular or dual nanoreporter) under conditions that allow binding of the target-specific sequences in the dual nanoreporter to the target molecule and (ii) detecting the spectral code associated with the dual nanoreporter. Depending on the nanoreporter architecture, the dual nanoreporter may be labeled before or after binding to the target molecule.

The uniqueness of each nanoreporter probe in a population of probe allows for the mutiplexed analysis of a plurality of target molecules. For example, in some embodiments, each nanoreporter probe contains six label attachment regions, where each label attachment region of each backbone is different from the other label attachment regions in that same backbone. If the label attachment regions are going to be labeled with one of four colors and there are 24 possible unique sequences for the label attachment regions and each label attachment region is assigned a specific color, each label attachment region in each backbone will consist of one of four sequences. There will be 4096 possible nanoreporters in this example. The number of possible nanoreporters can be increased, for example, by increasing the number of colors, increasing the number of unique sequences for the label attachment regions and/or increasing the number of label attachment regions per backbone. Likewise the number of possible nanoreporters can be decreased by decreasing the number of colors, decreasing the number of unique sequences for the label attachment regions and/or decreasing the number of label attachment regions per backbone.

In certain embodiments, the methods of detection are performed in multiplex assays, whereby a plurality of target molecules are detected in the same assay (a single reaction mixture). In a preferred embodiment, the assay is a hybridization assay in which the plurality of target molecules are detected simultaneously. In certain embodiments, the plurality of target molecules detected in the same assay is, at least 2, at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 different target molecules, or up to 5000 different target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, from 500 to 5000 different target molecules, and so on and so forth.

In certain embodiments, the invention is directed to detecting different splice forms of the same RNA. The different splice forms can be detected using a plurality of nanoreporter probes, each with a different target-specific sequence complementary to a different exon of the same gene.

In addition to the qualitative analytical capabilities provided by the nanoreporters of the invention and the analytical techniques based thereon, the nanoreporters of the invention are uniquely suitable for conducting quantitative analyses. By providing a one to one binding between the nanoreporters (whether singular or dual nanoreporters) of the invention and their target molecules in a biomolecular sample, all or a representative portion of the target molecules present in the sample can be identified and counted. This individual counting of the various molecular species provides an accurate and direct method for determining the absolute or relative concentration of the target molecule in the biomolecular sample. Moreover, the ability to address each molecule in a mixture individually leverages benefits of miniaturization including high sensitivity, minimal sample quantity requirements, high reaction rates which are afforded by solution phase kinetics in a small volume, and ultimately very low reagent costs.

As will be appreciated from the description and examples provided below, the present invention provides numerous advantages. For example, the complex modularity in forming nanoreporters according to the invention allows for systematic creation of libraries of unique nanoreporters having a very high degree of diversity (e.g., millions of uniquely recognizable nanoreporters). This modularity allows flexibility in customizing nanoreporter populations to specific applications which in turn provides significant manufacturing efficiencies. Another advantage that will be appreciated through the following description stems from the flexibility in assembling the nanoreporters of the invention. That is, due to their modular structure, the nanoreporters of the invention can be assembled prior to shipment to a point of use or assembled at the point of use.

Dual Nanoreporters

FIG. 1 and FIG. 2 illustrate certain embodiments of the invention involving dual nanoreporters. In some embodiments, each of the two components of the nanoreporter is labeled, such that the nanoreporter's spectral code is formed only when the two components of the nanoreporter come together upon binding of the dual nanoreporter to its target molecule. However, in a dual nanoreporter, it is not necessary that both components are labeled. For example, as depicted in FIG. 1 and FIG. 2, one component of a dual nanoreporter is labeled with the nanoreporter code, and the other component attached to an affinity tag (arrow) that is useful to immobilize the nanoreporter for stretching and visualization.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (e.g. to at least one) of the grammatical object of the article. By way of example, "an element" means one element or more than one element.

The terms "complementary" with respect to polynucleotides refer to polynucleotides related by the base-pairing rules. For example, the sequence "A-G-T," is complementary to the sequence "T-C-A." Complementarity may be partial, in which only some of the nucleic acids' bases are matched according to the base pairing rules. Or, there may be complete or total complementarity between the nucleic acids. The degree of complementarity between nucleic acid strands has significant effects on the efficiency and strength of hybridization between nucleic acid strands.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The recitations "sequence identity" or, for example, comprising a "sequence 50% identical to," as used herein, refer to the extent that sequences are identical on a nucleotide-by-nucleotide basis over a window of comparison. Thus, a "percentage of sequence identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (e.g., the window size), and multiplying the result by 100 to yield the percentage of sequence identity.

Terms used to describe sequence relationships between two or more polynucleotides include "homology", "comparison window", "sequence identity", "percentage of sequence identity" and "substantial identity". Because two polynucleotides may each comprise (1) sequence (e.g., only a portion of the complete polynucleotide sequence) that is similar between the two polynucleotides, and (2) sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997*, Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

Backbone Structure

The nanoreporter backbone of the present invention is a nucleic acid molecule, containing a plurality of label attachments regions (e.g. at least three label attachment regions) arranged in a linear combination to which label monomers can be directly or indirectly attached. In one embodiment, the nanoreporter backbone is a nucleic acid backbone in which the label attachment regions are single-stranded regions to which other nucleic acids, such as complementary oligonucleotide, complementary RNA sequences, or complementary DNA sequences, can attach by hybridization. In specific embodiments, the nanoreporter backbone is a single-stranded nucleic acid molecule.

In some embodiments, the backbone of the present invention is DNA. DNA based structures offer numerous advantages in the context of the present invention due at least in part to the vast universe of existing techniques and methodologies that allow manipulation of DNA constructs. As indicated above, the backbone may be single stranded.

Each backbone is comprised of a unique arrangement of label attachment regions. The label attachment regions of a nanoreporter backbone will vary in size depending on the method of labeling. In various embodiments, a label attachment region can have a length anywhere from 10 nm to 10,000 nm, but is more preferably from 50 nm to 5,000 nm, and is more preferably from 100 nm to 1,000 nm. In various embodiments, the label attachment region is from about 100 nm to about 500 nm, from about 150 nm to about 450 nm, from about 200 nm to about 400 nm, or from 250 to about 350 nm. In a preferred embodiment, the label attachment region corresponds closely to the size of a diffraction-limited spot, e.g., the smallest spot that can be detected with standard optics, which is about 300 nm.

In some embodiments, the label attachment regions of the present invention are made of polynucleotide sequences. For the nucleic acid backbones of the present invention, 1 nm corresponds to about 3 nucleotides; thus, an about 300 nm-label attachment region corresponds to a nucleotide sequence of about 900 bases. In certain embodiments, the label attachment region is from about 300 nucleotides to about 1.5 kb, from about 450 nucleotides to about 1.35 kb, from about 0.6 kb to about 1.2 kb, or from 0.75 kb to about 1.05 kb. In certain aspects, the label attachment region is about 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 or more nucleotides, including all integers in between. In certain preferred embodiments, the label attachment region is a nucleotide sequence of about 1100 nucleotides in length.

A backbone can have 1, 2, 3, 4, 5, 6, 7, 8, 9, 10, 11, 12, 13, 14, 15, 16, 17, 18, 19, 20, 21, 22, 23, 24-100 label attachment regions or more, including all integers in between. In certain embodiments, a backbone has 6 label attachment regions. In some embodiment the individual backbones have a set of distinct label attachment regions, each of which has a polynucleotide sequence that is different from the sequences of the other label attachment regions in that same backbone.

In some embodiments, a backbone has 6 unique label attachments regions. In some embodiments, each backbone comprises a plurality of different detectable molecules wherein said plurality of different detectable molecules in each backbone has a detectable signal that distinguishes it from other backbones in the population.

According to the present invention, each backbone in a population of backbones is distinguishable from the others by having a unique linear combination, order, or arrangement of label attachment regions. In addition, as one aspect of the present invention, the polynucleotide sequence of each label attachment region in a given backbone is different from the polynucleotide sequence of the other label attachment regions in that same backbone. In a linear arrangement of multiple label attachment regions on the same backbone, repeating more than one of the same label attachment regions can cause the plasmids from which the backbones are generated to be unstable during replication in *E. coli* and therefore difficult to propagate. In addition, the introduction of reverse-complement RNA segments to such a backbone may cause the formation of "knotted" reporters in which an RNA segment bridges and pulls together two identical label attachment regions, disrupting the linear sequence of the reporter and interfering with the accuracy and readability of the reporter code, among other problems. In embodiments in which plasmid instability and potentially poor reporter readability are a problem, these problems are avoided by constructing each individual backbone to have a set of distinct label attachment regions, each of which has a polynucleotide sequence that is different from the sequences of the other label attachment regions in that same backbone.

In addition, as a further aspect of the present invention, these label attachment regions are selected from a population of unique, rationally-designed (e.g., synthetic sequences) nucleotide sequences, each of which has a unique polynucleotide sequence represented by certain characteristics (e.g., G/C content, G/C ratio, adenine repeats), as detailed herein, and each of which is designated a given detectable molecule. These rationally-designed sequences not only improve stability by preventing secondary structure formation (e.g. keeping linear sequence of the reporter to maintain accuracy and readability of the reporter code), but optimize the concentration and spacing of the detectable molecules attached to each label attachment region, thereby improving the readability of a given labeled backbone among a population of uniquely labeled backbones.

Label Attachment Regions

The present invention provides nanoreporter backbones that are synthetic nucleic acid molecules (DNA, RNA, or DNA/RNA hybrids), rationally-designed to have features that optimize labeling and detection of the nanoreporter, and that prevent secondary structure formation. In some embodiments of the invention, a nanoreporter backbone is a designed polynucleotide sequence comprising one or more sequences from 50 to 50,000 bases long.

In some embodiments, the nanoreporter backbone is designed to minimize predictable secondary structures. In some embodiments the nanoreporter backbone are devoid of any secondary structure. Putatative secondary structures (e.g. hairpins, folding, or internal base pairing) can be predicted by methods known in the art such as MFOLD. Without intending to be limited to any theory, predictable secondary structure in the nanoreporter structure can be minimized by avoiding inverted repeats and by skewing the backbone-specific content such that the backbone is CT or GA-rich. In some embodiments, the nanoreporter backbone does not have any significant intra-molecular paring under annealing conditions of 75° C., 1×SSPE. In some embodiments, the nanoreporter backbone has less than about 20, 15, 10, 5, 4, 3, 2, or 1% of inverted repeats, wherein the inverted repeats are 9 nucleotides or greater. In some embodiments, the backbone has less than about 1% of inverted repeats, wherein the inverted repeats are 9 nucleotides or greater. In some embodiments, the nanoreporters do not contain any inverted repeat of 9 nucleotides or greater across a sequence that 1100 base pairs in length. In some embodiments, the nanoreporters do not contain any inverted repeat of 7 nucleotides or greater across any 100 base pair region. In some embodiments, the nanoreporter backbone is designed to skew the strand-specific content of the backbone such that the backbone is CT or GA-rich. A CT or GA region is a region compose by any combination of the nucleotides C and T, or G and A. For instance, the smallest CT region is a region of two nucleotides wherein the two nucleotides are C and T. The regions can be 2, 3, 4, 5, 6, 7, 8, or more nucleotides in length. In some embodiments about 30, 35, 40, 45, 50, 55, 60, 65 or 70% of the nanoreporter backbone is compose of CT or GA regions. In some embodiments about 50 to 65% of the nanoreporter backbone is composed of CT or GA regions. In some embodiments about 60% of the nanoreporter backbone is composed of CT or GA regions. In some embodiments, the nanoreporter backbone is designed to skew the strand-specific content of the backbone such that the backbone is CT-rich. In some embodiments about 60% of the nanoreporter backbone is composed of CT regions.

In some embodiments, the nanoreporter backbone is designed to maximize the uniqueness of all of the sequence in a nanoreporter population by avoiding direct repeats and by screening out all sequence that had any significant homology to any other sequence used in other backbones in a population of nanoreporters or to any sequence described in the REFSEQ public database. In some embodiments, the nanoreporter backbone has less than about 20, 15, 10, 5, 4, 3, 2, or 1% of direct repeats. In some embodiments, the nanoreporter backbone has less than about 1% of direct repeats, wherein the direct repeats are 9 nucleotides or more in a sequence of 1100 base pair of length or 7 nucleotides or more across any 100 base pair region. In some embodiments, the nanoreporters described herein contain less than 85, 80, 70, 60, 50, 40, 30, 20, 10, or 5% homology to any other sequence used in other backbones in a population of nanoreporters or to any sequence described in the REFSEQ public database. In some embodiments, the nanoreporters described herein contain less than 60% homology to any other sequence used in other backbones in a population of nanoreporters or to any sequence described in the REFSEQ public database. In some embodiments, the nanoreporters described herein contain less than 50% homology to any other sequence used in other backbones in a population of nanoreporters or to any sequence described in the REFSEQ public database. In some embodiments, the nanoreporter's backbone is designed to contain less than 85% homology to any other sequence used in the backbones or to any sequence described in the REFSEQ public database. In some embodiments, the nanoreporters backbone is designed to contain less than 20, 16, 15, 10, 9, 7, 5, 3, 2 contiguous bases of homology to any other sequence used in the backbones or to any sequence described in the REFSEQ public database. In some embodiments, the nanoreporters backbone is designed to have no more than 15 contiguous bases of homology and no more than 85% identity across the entire length of the nanoreporter to any other sequence used in the backbones or to any sequence described in the REFSEQ public database.

The nucleic acid label attachment regions of the invention preferably do not have direct or inverted repeats that are greater than 12 bases in length. In other embodiments, the nucleic acid label attachment regions do not have direct or inverted repeats that are greater than about 7, 8, 9, 10, 11, 12, 13, 14, 15, 16 or more nucleotides bases in length. In some embodiments, the nucleic acid label attachment regions do not contain any inverted repeat of 9 nucleotides or greater across a sequence that 1100 base pairs in length. In some embodiments, the nucleic acid label attachment regions do not contain any inverted repeat of 7 nucleotides or greater across any 100 base pair region.

Sequences may also be screened to avoid common six-base-cutter restriction enzyme recognition sites. Selected sequences may be additionally subjected to predicted secondary structure analysis, and those with the least secondary structure may be chosen for further evaluation. Any program known in the art can be used to predict secondary structure, such as the MFOLD program (Zuker, 2003, *Nucleic Acids Res.* 31 (13):3406-15; Mathews et al., 1999, *J. Mol. Biol.* 288:911-940).

The nanoreporter backbone, which in some embodiments is a single-stranded nucleic acid molecule, is designed to have one or more label attachment regions, comprising a regular pattern of a particular base (the "regularly-repeated base"). In such regions, the regularly-repeated base typically occurs with a minimal periodicity of about every nth residue, where n is any number, and preferably from 4 to 25. Preferably, not more than 25% of the regularly-repeated base in a label attachment region appears at other than said regular intervals. For example, if in a label attachment region of 100 nucleotides there are 12 thymine bases, and thymine is the regularly-repeated base, in this aspect of the invention not more than 25% of these, i.e., 3 thymine bases, appear outside the regular pattern of thymines. Similarly, if in a label attachment region of 100 nucleotides there are 12 adenine bases, and adenine is the regularly-repeated base, in this aspect of the invention not more than 25% of these, i.e., 3 adenine bases, appear outside the regular pattern of adenines. In specific embodiments, not more than 20%, not more than 15%, not more than 10%, not more than 9%, not more than 8%, not more than 7%, not more than 6%, not more than 5%, not more than 4%, not more than 3%, not more than 2% or not more than 1% of said base appears at other than said regular intervals in said region. In some embodiments, the bases are not regularly-spaced but the bases are at least an average of 8, 9, 10, 12, 15, 16, 18, 20, 30, or 50 nucleotides apart. In some embodiments, the bases are not regularly-spaced but the bases are at least an average of 8 nucleotides apart.

In certain embodiments, the regularly-repeated base in a given label attachment region is spaced at least about every 4, 5, 6, 7, 8, 9, 10, 11, 12, 13, 14, 15, 16, 17, 18, 19, 20, 21, 22, 23, 24, 25, or more nucleotide bases. In certain aspects, the regularly repeated base is spaced at about every 5 to 15 nucleotide bases, about every 6 to 12 nucleotide bases, about every 7 to 10 nucleotide bases, or about every 8 to 10 nucleotide bases. In certain aspects, the regularly repeated base is spaced at about every 8 nucleotide bases. In certain specific embodiments, an adenine base is repeated at about every 8 nucleotide bases. In certain specific embodiments, an adenine base is repeated at about every 15 to 20 nucleotide bases. In certain specific embodiments, an adenine base is repeated at about every 16 nucleotide bases.

The regularly repeated base may be present in a the polynucleotide sequence of a given label attachment region at about 5%, 6%, 7%, 8%, 9%, 10%, 11%, 12%, 13%, 14%, 15%, 16%, 17%, 18%, 19%, 20% nucleotide content. The presence of a regularly repeated base at an average of about every 8 to 16 nucleotides in a label attachment region represents about 12.5% nucleotide content. In certain embodiments, the nucleotide content of the regularly repeated base may be about 12.5%. In certain aspects, the label attachment region comprises a selected number or selected percentage of regularly-repeated bases per region, which are distributed randomly except that they must be at least a certain minimum distance apart, such at least about 8, 9, 10, 11, 12, 13, 14, 15, 16, 17, 18, 19, 20, 21, 22, 23, 24, or more bases apart.

The regularly repeated base can be any nucleotide base of adenine, thymine, guanine, cytosine, or uracil. In certain embodiments, the regularly repeated base in the single-stranded label attachment region is adenine.

In certain aspects, the polynucleotide sequence of the label attachment regions is also designed to have a certain guanine/cytosine (G/C) content. For example, certain label attachment regions are designed to have an overall G/C content of about 45%, 46%, 47%, 48%, 49%, 50%, 51%, 52%, 54%, 55%, 56%, 57%, 58%, 59%, 60%, more preferably about 50%, as this provides a fairly consistent $T_M$ among the numerous, unique polynucleotide sequences of the label attachment regions. In certain aspects, the polynucleotide sequences have no more than three guanines in a row, to minimize synthesis issues. The overall GC-content is also preferably consistent over relatively short stretches to make local Tm's similar. Without intending to be limited to any theory, when the nanoreporter is a double stranded nucleic acid the Tm of the nanoreporters described herein provides for stronger bonds between the nanoreporter backbone and the complementary polynucleotide sequence having attached thereto a detectable molecule, therefore, preventing dissociation during synthesis and hybridization procedures. In addition, the consistent Tm among the population of nanoreporters allows for the synthesis and hybridization procedures to be tightly optimized, as the optimal conditions are the same for all spots and positions. In some embodiments, the sequences of the nanoreporters have about 50% guanine/cytosine (G/C), with no more than three Gs in a row.

In certain aspects, the polynucleotide sequence of the label attachment regions is also designed to have a certain G/C ratio in a given strand. For example, certain embodiments the polynucleotide sequence of the label attachment regions are designed such that the complementary polynucleotide sequences have a G/C ratio of about 1/1, 2/1, 3/2, about 5/3, or about 7/5. In certain aspects, the G/C ratio is at least 1/1. In certain aspects, the G/C ratio is about 1/1, 2/1, 3/2, 5/3, or about 7/5 in a given strand. In certain aspects, the G/C ratio is at least 1/1 in the complementary polynucleotide sequence. In certain aspects, the G/C ratio is about 3/2 in the complementary polynucleotide sequence.

In certain specific embodiments, in which adenine is the regularly repeated base, spaced at least about every 8 nucleotides (about 12.5% adenine content), and the G/C content is about 50%, the thymine content may be about 37-38%, or about 37.5%. In certain specific embodiments, in which adenine is the regularly repeated base, and the G/C content is about 50% In some embodiments, the thymine content may be about 35-45%. In an exemplary label attachment region in which the regularly-repeated nucleotide is adenine and a GC content of about 50%, excess adenines may be utilized to make up the loss in abundance of T's. To generate the selected sequence, random sequences with fixed patterns of. As ranging from every 4th base to every 25th base may be created and screened to minimize the presence of inverted and direct repeats.

In some embodiments, the present invention provides nanoreporter or nanoreporter label unit populations, for example nanoreporter or nanoreporter label unit libraries, that contain at least 3, at least 5, at least 10, at least 15, at least 20, at least 25, at least 30, at least 35, at least 40, at least 45, at least 50, at least 60, at least 70, at least 80, at least 90, at least 100, at least 200, at least 300, at least 400, at least 500, at least 750, or at least 1,000 unique nanoreporters, unique nanoreporter label units, or unique labeled nanoreporters. As used herein, "unique" when used in reference to a nanoreporter or nanoreporter label units within a population is intended to mean a nanoreporter that has a code that distinguishes it from other nanoreporters in the same population, e.g., each nanoreporter has a detectable signal that distinguishes it from other nanoreporters in said population. Typically, a nanoreporter is rendered "unique" by the particular linear combination of label attachment regions each having attached thereto a selected label monomer.

In specific embodiments, the present invention provides nanoreporter populations with at least 1,000, 5,000, at least 10,000, at least 20,000 or at least 50,000 unique nanoreporters or nanoreporter label units.

The nanoreporters in a population of nanoreporters can be singular nanoreporters, dual nanoreporters, or a combination thereof. The nanoreporters can be labeled or unlabeled. The population of nanoreporters described herein can comprise two or more nanoreporters.

In some embodiments, the invention provides for a population of nanoreporter backbones in which a base (e.g. adenine) is regularly spaced, the nanoreporters do not have any significant formation of secondary structures and the Tm among the nanoreporters in the population is fairly consistent. In some embodiments, the invention provides a population of nanoreporters in which the Tm of the complementary polynucleotide sequences when hybridized to its label attachment regions is about 80° C. or higher.

In some embodiments, the invention provides for a population of nanoreporter backbones wherein each nanoreporter backbone comprises a region comprising a plurality of label attachment regions covalently attached together in a linear combination, wherein each label attachment region comprises about 800 to 1300 nucleotide bases and has a G/C content of about 50%, wherein each selected label attachment region is different from the other selected label attachment regions, and wherein each label attachment region is hybridized to a complementary polynucleotide sequence having attached thereto one or more detectable molecules, wherein the complementary polynucleotide sequence has a G/C ratio of at least 1/1. In some embodiments, the complementary polynucleotide sequence has a G/C ratio of about 3/2. In some embodiments, the nanoreporter backbone is designed to skew the strand-specific content of the backbone such that the backbone is CT-rich. In some embodiments about 60% of the nanoreporter backbone is composed of CT regions.

In some embodiments, the invention provides for a population of nanoreporter backbones wherein each nanoreporter backbone comprises a single-stranded nucleic acid backbone, said backbone comprising a plurality of label attachment regions covalently attached together in a unique linear combination, wherein said nanoreporter backbone comprises a base (e.g. adenine) regularly spaced, the nanoreporters backbones do not have any significant formation of secondary structures and contain less than 85% homology to any other sequence used in other backbones in the population or to any sequence described in the REFSEQ public database.

In some embodiments, the invention provides for a population of nanoreporter backbones wherein each nanoreporter backbone comprises a single-stranded nucleic acid backbone, said backbone comprising a plurality of label attachment regions covalently attached together in a unique linear combination, wherein said nanoreporter backbone has a G/C content of about 50%, the nanoreporters backbones do not have any significant formation of secondary structures and contain less than 85% homology to any other sequence used in other backbones in the population or to any sequence described in the REFSEQ public database.

In some embodiments, the invention provides for a population of nanoreporter backbones wherein each nanoreporter backbone comprises a single-stranded nucleic acid backbone, said backbone comprising a plurality of label attachment regions covalently attached together in a unique linear combination, wherein said nanoreporter backbone has a G/C content of about 50%, the nanoreporters backbones do not have any significant formation of secondary structures and contain less than 1% direct repeat sequences.

In some embodiments, the invention provides for a population of nanoreporter backbones wherein each nanoreporter backbone comprises a single-stranded nucleic acid backbone, said backbone comprising a plurality of label attachment regions covalently attached together in a unique linear combination, wherein the label attachment regions are selected from a population of unique, designed polynucleotide sequences, wherein each polynucleotide sequence is hybridized to a unique complementary polynucleotide sequence having attached thereto one or more detectable molecules, wherein each nanoreporter has a detectable signal that distinguishes it from other nanoreporters in said population, and wherein each nanoreporter is more stable than a comparable nanoreporter comprising M13 DNA.

In some embodiments, the invention provides for a population of nanoreporter backbones wherein each nanoreporter backbone comprises a single-stranded nucleic acid backbone, said backbone comprising a plurality of label attachment regions covalently attached together in a unique linear combination, wherein the label attachment regions are selected from a population of unique, designed polynucleotide sequences, wherein each polynucleotide sequence is hybridized to a unique complementary polynucleotide sequence having attached thereto one or more detectable molecules, wherein each nanoreporter has a detectable signal that distinguishes it from other nanoreporters in said population, wherein the Tm of the complementary polynucleotide sequences when hybridized to its label attachment regions in the nanoreporters described herein are higher than the Tm of a polynucleotide sequences complementary to a M13 DNA template when hybridized to a nanoreporter probe comprising the M13 DNA.

In some embodiments, the invention provides for a population of nanoreporter backbones wherein the sequence characteristics of the nanoreporter probes described herein provide improved detection of a target molecule. For instance, when the binding of the nanoreporter probes to target molecules is performed by individually counting the presence of one or more molecules of the nanoreporter in a sample, the nanoreporter probes described herein allow for an increased in the number of counts. In some embodiments, the number of molecular counts above background of said molecular complex after normalization of the sample is higher than 300, 400, 450, 500, 600, 700, 800, 900 or 1000 molecular counts. In some embodiments, the nanoreporter probes described herein allow for an increased in the number of counts. In some embodiments, the number of molecular counts above background of said molecular complex after normalization of the sample is higher than 400 molecular counts. In some embodiments, the percentage of valid molecular counts of the nanoreporter probes described herein is higher that about 10, 11, 12, 12.5, 14, 15, 20, 25, 30, 35, 40, 50, 60, 70, 80 or 90%. In some embodiments, the percentage of valid molecular counts of the nanoreporter probes described herein is higher that about 12.5%. In some embodiments, the number of molecular counts above background of the nanoreporter probes described herein after normalization of said sample is at least 2, 5, 6, 10, 15, 20, 30, 40, 50, 60, 70, 80, or 90 fold higher than a comparable nanoreporter comprising M13 DNA. In some embodiments, the number of molecular counts above background of the nanoreporter probes described herein after normalization of said sample is at least 6 fold higher than a comparable nanoreporter comprising M13 DNA. In some embodiments, the number of molecular counts above background of the nanoreporter probes described herein after normalization of said sample is at least 2 fold higher than a comparable nanoreporter comprising M13 DNA.

A comparable M13 nanoreporter probe is a nanoreporter comprising the same target specific region as the nanoreporters probes described herein attached to a single-stranded backbone comprising a plurality of M13 DNA regions covalently attached together wherein each region is hybridized to a complementary polynucleotide sequence having attached thereto one or more detectable molecules.

The size of a nanoreporter probe population and the nature of the target-specific sequences of the nanoreporters within it will depend on the intended use of the nanoreporter. Nanoreporter probe populations can be made in which the target-specific sequences correspond to markers of a given cell type, including a diseased cell type. In a specific embodiment, the cell or tissue is a mammalian cell or tissue, and more preferably is a human cell or tissue.

In some embodiments, an appropriate sequence is divided into label attachment regions ranging from 50 bases to 2 kilobases long (could be longer). Label attachment regions can also range from about 200 bases to about 1800 bases, about 400 bases to about 1600 bases, about 600 bases to about 1500 bases, about 800 bases to about 1300 bases, about 900 bases to about 1200 bases, about 1000 bases to about 1150 bases, about 1050 bases to about 1150 bases, including combinations of these exemplary ranges and all integers in between (e.g., 850, 950, etc). In certain embodiments the label attachment regions are about 1100 bases.

In some embodiments, each label attachment region is a unique sequence, but contains a consistent and minimal number and spacing of adenines, or other selected base, in relation to the other label attachment regions in a given reporter sequence. These label attachment regions can interspersed with other regions whose sequence does not matter. The label attachment regions in a nanoreporter backbone can be of different lengths and/or have different regularly-repeated bases.

Specific examples of polynucleotide sequences that may be utilized as templates to synthesize single stranded label attachment regions include the polynucleotide sequences set forth in SEQ ID NOS:1, 2, 3, 4, 5, 6, 7, 8, 9, 10, 11, 12, 13, 14, 15, 16, 17, 18, 19, 20, 21, 22, 23, and 24. For these sequences, the recited regularly repeated base is thymine, which produces adenine as the regularly repeated based upon synthesis of the single stranded label attachment regions, typically in the form of a nanoreporter backbone. Also contemplated are variants of these polynucleotide sequences, including polynucleotides sequences having at least 60%, 70%, 80%, 90%, 95%, 98%, or more sequence identity to the polynucleotide sequences set forth in SEQ ID NOS:1-24, wherein such variants retain the desired or suitable characteristics of a label attachment region, as described in greater detail herein (e.g., regularly-repeated base, G/C content, G/C ratio in a given strand, Tm, lack of inverted repeats). As it will be appreciated by one of ordinary skill in the art, other sequences can be designed to possess the desired or suitable characteristics of a label attachment region described herein.

An optimized start sequence for transcription by RNA polymerase T7, T3, or SP6 (beginning at position +1 of the transcript) can be added to the 5' end of each label attachment region. Restriction sites are optionally added at the boundaries of each label attachment region to allow specific addition or deletion of individual label attachment regions to the sequence using conventional cloning techniques.

The number of label attachment regions in a nanoreporter backbone preferably ranges from 1 to 50. In yet other embodiments, the number of synthetic label attachment regions in a nanoreporter backbone ranges from 1, 2, 3, 4, 5, 6, 7, 8, 9, or 10 rationally-designed label attachment regions to 15, 20, 30, 40, or 50 label attachment regions, or any range in between. In certain embodiments, the number of label attachment regions in a backbone is six.

In some embodiments, the regularly-repeated base in the label attachment region in a nanoreporter backbone, or its complementary regularly-repeated base in an annealed complementary polynucleotide sequence (or segment) can be used to attach label monomers, preferably light emitting label monomers, to the nanoreporter in a regular, evenly spaced pattern for better distribution of the nanoreporter signal. Preferably, where a label attachment region is labeled, at least 20%, at least 30%, at least 40%, at least 50%, at least 60%, at least 70%, at least 80%, at least 90%, at least 95% or at least 98% of occurrences of the regularly-repeated base is attached to at least one light-emitting label monomer, either by covalent attachment of a label monomer to a base, or by hybridization to a nucleic acid in which the complements of the regularly-repeated base are so-labeled.

This percentage of occurrences can be measured by any means known in the art. In one method, the amount of nucleic acid produced in a labeling reaction is purified (for example, RNA can be purified using a Qiagen™ RNeasy Kit®) and subjected to UV spectrophotometry. The absorbance ("A") at the appropriate wavelengths is measured for each of the nucleic acid (260 nm) and the label monomer whose occurrence is to be measured (e.g., 495 nm for Alexa Fluor® 488; 590 nm for Alexa Fluor® 594; 650 for Alexa Fluor® 647; and 550 nm for Cy3). The absorbance of the nucleic acid is corrected by adjusting the value of the absorbance at 260 nm ("A260") to remove the "noise" contribution from the label monomer by subtracting the absorbance at the peak wavelength for the label monomer ($A_{LM}$) minus the correction factor for that label monomer. Where the nucleic acid is RNA, the number of label monomers per one thousand nucleotides is calculated according to the formula:

$$\frac{\text{no. of labelmonomers}}{\text{1000 nucleotides}} = \frac{A260}{A_{LM}} \times \frac{9010}{EC_{LM}} \times 1000$$

where $EC_{LM}$ is the extinction coefficient for the label monomer. From this formula, the percentage of occurrences of the regularly-repeated base that are attached to a light-emitting label monomer can be calculated.

In some embodiments, the preferred regularly-repeating base in a label attachment region is adenine, so that the region can be labeled by hybridization to one or more complementary polynucleotide sequences (e.g., RNA segments) in which the regularly-repeated base is uracil. In some embodiments, adenine is not regularly-repeated but is spaced at least an average of 8 bases apart. This permits the use of amino-allyl-modified UTPs, which are readily commercially available, as label monomer attachment sites, in an otherwise random sequence. Preferably, in addition to the regular periodicity of the label attachment regions, the regions (and the nucleic acid comprising them) contain minimal secondary structure and fairly consistent Tm.

The nucleic acids of the present invention can be chemically synthesized using naturally occurring nucleotides or variously modified nucleotides designed to increase the biological stability of the molecules or to increase the physical stability of the duplex formed between the label attachment region and the annealed complementary polynucleotide sequences or segments, e.g., phosphorothioate derivatives and acridine substituted nucleotides can be used. Examples of modified nucleotides which can be used to generate the synthetic nucleic acid include 5-fluorouracil, 5-bromouracil, 5-chlorouracil, 5-iodouracil, hypoxanthine, xanthine, 4-acetylcytosine, 5-(carboxyhydroxyl methyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Alternatively, the synthetic nucleic acid can be produced biologically using a vector into which a nucleic acid has been subcloned. As one example, a linear single-stranded DNA backbone can be made from a double stranded plasmid DNA using a four step protocol that includes (i) linearization of the dsDNA with a restriction enzyme, (ii) dephosphorylation with a thermolabile phosphatase, (iii) digestion with a second restriction enzyme to separate the cloning vector from the backbone sequence, and (iv) digestion with a strand-specific lambda exonuclease digestion, leaving only one strand of the backbone fragment intact.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 40:5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, *Bioorganic & Medicinal Chemistry* 4(1): 5-23; Perry-O'Keefe et al., 1996, *Proc. Natl. Acad. Sci. USA* 93: 14670-675.

In an exemplary embodiment, the selected novel sequence can be constructed synthetically as double-stranded DNA by a commercial gene synthesis company and cloned in an oriented fashion into a "phagemid", a plasmid vector containing an M13 or fl phage intergenic (IG) region which contains the cis-acting sequences necessary for DNA replication and phage encapsidation, such as pUC119. The appropriate orientation of the cloned insert relative to the phage origin of replication allows for the generation of a single-stranded DNA backbone which is the reverse complement of the RNA molecules generated by in vitro transcription for each label attachment region.

In order to generate the single-stranded DNA backbone of the novel reporter, the phagemid is transformed into an *E. coli* strain containing an F' episome. Subsequent infection of the transformed bacteria with a helper phage such as the M13 mutant K07 results in the secretion of the phagemid carrying the novel reporter sequence as a single-stranded, packaged phage from which the circular, single-stranded DNA is prepared using a standard protocol. This DNA is linearized and the vector portion is excised by annealing short, complementary oligonucleotides to either end of the novel reporter sequence to generate double-stranded restriction sites, followed by treatment with the appropriate restriction enzymes. FIG. 9 shows an example of plasmid vector that may be used to clone, propagate, and generate the nanoreporters described herein.

Complementary Polynucleotide Sequences

In some embodiments, detectable molecules, or label monomers, that provide or emit signals which constitute all or part of the nanoreporter code are attached to label attachment region(s) of the nanoreporter backbone through a structure referred to herein as a complementary polynucleotide sequence. The detectable molecules can be directly (e.g., covalently or noncovalently) attached to a complementary polynucleotide sequence, or indirectly attached to such a sequence (e.g., through an intermediate component, such as a ligand).

In some embodiments, complementary polynucleotide sequences can be from 25 nucleotides to several kilobases (e.g., 5 kb) in length, and are preferably 50 nucleotides to 2 kb in length. In specific embodiments, complementary polynucleotide sequences are about 25 to 250, 50 to 200, 50 to 150, or 50 to 100 nucleotides in length. In other embodiments, complementary polynucleotide sequences are about 500 to 2,000, 500 to 1,500, 500 to 1,000, 750 to 1,250, or 750 to 1,000 nucleotides in length. In certain aspects, complementary polynucleotide sequences are about 800, 850, 900, 950, 1100, 1150, or 1100 nucleotides in length, including all integers in between. Complementary polynucleotide sequences can be complementary RNA polynucleotide or complementary DNA polynucleotide. In preferred embodiment, complementary polynucleotide sequences are complementary RNA polynucleotides.

A detectable molecule or label monomer can be covalently attached to a complementary polynucleotide sequence before or after the sequence is attached to the label attachment region of a nanoreporter backbone. For example, in attaching a detectable molecule to a complementary polynucleotide sequence, the label can be covalently attached by incorporation of a nucleotide containing a detectable molecule into the nucleic acid during its synthesis, but before it is hybridized the label attachment region of the backbone. Alternatively, during the synthesis of a complementary polynucleotide sequence, a nucleotide containing a detectable molecule acceptor group can be included, and the detectable molecule added to the complementary polynucleotide sequence after its synthesis, either before or after it is hybridized to the label attachment region of the backbone. Alternatively, the label monomer can be indirectly attached to the complementary polynucleotide sequence, for example, by incorporating a nucleotide containing a ligand-binding molecule (e.g., biotin) into the complementary polynucleotide sequence during synthesis, and by adding a ligand (e.g., streptavidin) that is covalently attached to the detectable molecule.

In some embodiments, a complementary polynucleotide sequence can range anywhere from 20 nucleotides to more than 5 kb in length, depending on the method of assembly of the nanoreporter. For example, where a complementary polynucleotide sequence has covalently incorporated into it one or more label monomers that provide signals that are part of the nanoreporter code in the context of the labeled nanoreporter, the complementary polynucleotide sequence is preferably about 100 to about 10,000 bases, more preferably 200 to about 2000 bases, and yet more preferably 700 to about 1200 nucleotides in length, or about 1100 base pairs in length, and is generally referred to herein as a segment, a dark segment being the complementary polynucleotide sequence prior to the incorporation of the label monomer (but, in a preferred embodiment, containing label monomer acceptor sites, such as amino allyl nucleotides), and a colored segment being one containing the desired label monomer or label monomers. The $T_m$ of a segment when hybridized to its label attachment region preferably is >80° C., more preferably >90° C., in 825 mM $Na^+$ (5×SSC).

As with the label attachment regions, a complementary polynucleotide sequence may comprise a pattern of regularly-repeated bases or it may comprise a similar percentage of bases, such as a guanine, adenine, thymine, cytosine, or uracil repeat base. When the repeat base in the single-stranded label attachment region is adenine, the repeat base in the complementary polynucleotide sequence may be thymine if the complementary polynucleotide sequence is a complementary DNA polynucleotide, or uracil if the complementary polynucleotide sequence is a complementary RNA polynucleotide.

The regularly-repeated base in a given complementary polynucleotide sequence may be spaced about every 4, 5, 6, 7, 8, 9, 10, 11, 12, 13, 14, 15, 16, 17, 18, 19, 20, 21, 22, 23, 24, 25, or more nucleotide bases. In certain aspects, the regularly repeated base is spaced at about every 5 to 15 nucleotide bases, about every 6 to 12 nucleotide bases, about every 7 to 10 nucleotide bases, or about every 8 to 10 nucleotide bases. In certain aspects, the regularly repeated base is spaced about every 8 nucleotide bases. In certain aspects, the regularly repeated base is spaced about every 15 to 20 nucleotide bases. In certain aspects, the regularly repeated base is spaced about every 16 nucleotide bases.

In certain aspects, the regularly repeated base is amino-allyl modified. This modification allows ready attachment (e.g., direct or indirect, as above) of a detectable molecule or label monomer to the regularly repeated base. The amino-allyl modified base may be a guanine, adenine, thymine, cytosine, or uracil base. In certain embodiments, the regularly repeated base is an amino-allyl modified uracil base.

In certain aspects, the detectable molecule or label monomer is attached to the regularly repeated base, such as via the amino-allyl modification of that base. In certain aspects, the detectable molecule is attached to all or almost all of the regularly repeated bases in a given polynucleotide complementary polynucleotide sequence. In certain embodiments, the detectable molecule is attached to about 10%, 20%, 30%, 40%, 50%, 60%, 70%, 80%, 90%, or 100% of the regularly repeated bases in a given complementary polynucleotide sequence.

In certain aspect, the detectable molecule or label monomer is attached to a base that is not regularly repeated but that is at least 8 bases apart such as via the amino-allyl modification of that base. The brightness of the complementary polynucleotide sequence can vary according the number of bases in the sequence or the number of labeled bases in the sequence.

As one specific example, when adenine is regularly repeated in the single stranded label attachment region and is present at about every 8 nucleotide bases, an amino-ally modified uracil may also be present in the complementary RNA polynucleotide at about every 8 nucleotide bases. Also, the amino-ally modified uracils may incorporate randomly into the complementary polynucleotide sequences, such as by adjusting the ratio of uracil bases to modified uracil basis in the synthesis reaction. In these instances, the detectable molecule, such as a fluorescent dye, may be incorporated into all or almost all of the amino-allyl modified uracils (e.g., at about every 8 bases) or it may be incorporated into the amino-allyl modified uracil bases at random.

By modifying the number of regularly repeated bases (e.g., every 5, 6, 7, 8, 9, 10, or more bases), and incorporating the detectable molecule into every regularly repeated base, every other regularly repeated base, every third regularly repeated base, or at random, etc., or combinations thereof, the detectable molecule can be incorporated into about every 5, 6, 7, 8, 9, 10, 11, 12, 13, 14, 15, 16, 17, 18, 19, 20, or more nucleotide bases, depending on the desired level of detectable signal.

In certain embodiments, the complementary polynucleotide sequences is an RNA polynucleotide comprising a sequence that is complementary to the single stranded label attachment regions generated by the polynucleotide template sequences set forth in SEQ ID NOS:1-24. A complementary RNA polynucleotide may be complementary to the full-length sequence of any of label attachment regions generated from the template sequences of SEQ ID NOS:1-24, or it may be complementary to a region within that polynucleotide sequence, such as a region comprising of 100, 200, 300, 400, 500, 600, 700, 800, 900, 1000, or more nucleotide bases, including all integers in between.

In the embodiments where the complementary polynucleotide sequence is an RNA polynucleotide, the complementary RNA nucleotides (e.g., segments) for each label attachment region may be made using methods known in the art, such as standard in vitro transcription (IVT) protocols. To synthesize the complementary RNA nucleotides, polymerase chain reaction ("PCR") primers may be designed to generate a double-stranded template beginning with an RNA polymerase promoter (T7, T3, or SP6) directly upstream (5') of the transcription start site and ending following the 3' restriction enzyme site. In certain aspects, the templates for these IVT reactions may include the synthetic DNA products of the templates described in SEQ ID NOS:1-24, or variant sequences thereof, which have been cloned downstream of T7, T3 or SP6 RNA polymerase promoters. Using such templates, in vitro transcription of RNA molecules may be performed in the presence of amino-allyl modified regularly-repeated base in the RNA (e.g., UTP) and unmodified other bases (e.g., ATP, CTP and GTP). This leads to an RNA product in which every regularly-repeated base (e.g., U) is modified to allow covalent coupling of a label monomer at that position in the RNA molecule.

The resulting amino-allyl modified transcripts (aa segments) may then be coupled to various fluorophores (e.g., Alexa 488 (blue), Alexa 546 (green), Alexa 594 (yellow), and Alexa 647 (red)—other dyes can also be used). The Alexa fluorophores may be purchased as succinimidyl- or TFP-esters (Invitrogen™) and may be coupled to the transcripts via the formation of amide bonds using standard protocols. The level of dye-incorporation in a segment correlates with the number of possible attachment sites (amino allyl (aa) moieties). To make the brightest possible colored segments, 100% aaUTP is used. To change the brightness, a mixture of aaUTP and unmodified UTP in any ratio can be used in the IVT reactions to modify the number of aa sites present on an aa segment. The desired brightness varies with the optics of the detection system.

Detectable Molecules or Label Monomers

The nanoreporters of the present invention can be labeled with any of a variety of label monomers, such as a radioisotope, fluorochrome, dye, enzyme, nanoparticle, chemiluminescent marker, biotin, or other monomer known in the art that can be detected directly (e.g., by light emission) or indirectly (e.g., by binding of a fluorescently-labeled antibody). Generally, one or more of the label attachment regions in the nanoreporter is labeled with one or more label monomers, and the signals provided by the label monomers attached to the label attachment regions of a nanoreporter constitute a detectable code that identifies the target to which the target-specific region of the nanoreporter binds. In certain embodiments, the lack of a given signal from the label attachment region (e.g., a dark spot) can also constitute part of the nanoreporter code.

In certain embodiments, such as when a nanoreporter backbone is constructed from a library (e.g. the exemplary label attachment regions templates of SEQ ID NOS:1-24), each unique label attachment region may be assigned a given detectable molecule. Merely by way of specific illustration, in a library of the 24 unique label attachment regions, e.g. products for templates SEQ ID NOS:1-24, the products of templates SEQ ID NOS:1, 5, 9, 13, 17, and 21 may be assigned a first detectable molecule, such as a blue fluorophore, the products of templates SEQ ID NOS:2, 6, 10, 14, 18, and 22 may be assigned a second detectable molecule, such as a green fluorophore, the products of templates SEQ ID NOS:3, 7, 11, 19, and 23 may be assigned a third detectable molecule, such as a yellow fluorophore, and the products of templates SEQ ID NOS: 4, 8, 12, 20, and 24 may be assigned a fourth detectable molecule, such as a red fluorophore. A person skilled in the art will appreciate that this example is merely illustrative, and that numerous combinations or alternatives may be utilized to accomplish the goal of creating a population of uniquely detectable nanoreporters, including the use of libraries of different sizes and having sequences other than those set forth in SEQ ID NOS:1-24.

Another example of label monomers that can be utilized by the invention are fluorophores. Several fluorophores can be used as label monomers for labeling nucleotides including, for example, fluorescein, tetramethylrhodamine, and Texas Red®. Several different fluorophores are known, and more continue to be produced, that span the entire spectrum. Also, different formulations of the same fluorophore have been produced for different applications. For example, fluorescein can be used in its isothiocynanate form (FITC), as mixed isomer or single isomer forms of carboxyfluorescein succinimidyl ester (FAM™), or as isomeric dichlorotriazine forms of fluorescein (DTAF). These monomers are chemically distinct, but all emit light with a peak between 515-520 nm, thereby generating a similar signal. In addition to the chemical modifications of fluorescein, completely different fluorophores have been synthesized that have the same or very similar emission peaks as fluorescein. For example, the Oregon Green® dye has virtually superimposable excitation and emission spectra compared to fluorescein. Other fluorophores such as Rhodol Green™ and Rhodamine Green™ are only slightly shifted in their emission peaks and so also serve functionally as substitutes for fluorescein. In addition, different formulations or related dyes have been developed around other fluorophores that emit light in other parts of the spectrum.

Non-radioactive and non-fluorescent label monomers are also available. For example, biotin can be attached directly to nucleotides and detected by specific and high-affinity binding to avidin or streptavidin which has been chemically coupled to an enzyme catalyzing a colorimetric reaction (such as phosphatase, luciferase, or peroxidase). Digoxigenin-labeled nucleotides can similarly be used for non-isotopic detection of nucleic acids. Biotinylated and digoxigenin-labeled nucleotides are commercially available.

Very small particles, termed nanoparticles, also can be used as label monomers to label nucleic acids. These particles range from 1-1000 nm in size and include diverse chemical structures such as gold and silver particles and quantum dots.

When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light which when superimposed will give a specific, unique color. The particles are being manufactured by companies such as Genicon Sciences. Derivatized silver or gold particles can be attached to a broad array of molecules including, proteins, antibodies, small molecules, receptor ligands, and nucleic acids. For example, the surface of the particle can be chemically derivatized to allow attachment to a nucleotide.

Another type of nanoparticles that can be used as a label monomer are quantum dots. Quantum dots are fluorescing crystals 1-5 nm in diameter that are excitable by a large range of wavelengths of light. These crystals emit light, such as monochromatic light, with a wavelength dependent on their chemical composition and size. Quantum dots such as CdSe, ZnSe, InP, or InAs possess unique optical properties.

Many dozens of classes of particles can be created according to the number of size classes of the quantum dot crystals. The size classes of the crystals are created either 1) by tight control of crystal formation parameters to create each desired size class of particle, or 2) by creation of batches of crystals under loosely controlled crystal formation parameters, followed by sorting according to desired size and/or emission wavelengths. Use of quantum dots for labeling particles, in the context of the present invention, is new, but is old in the art of semiconductors. Two examples of earlier references in which quantum dots are embedded within intrinsic silicon epitaxial layers of semiconductor light emitting/detecting devices are U.S. Pat. Nos. 5,293,050 and 5,354,707 to Chapple Sokol, et al.

In specific embodiments, one or more of the label attachments regions in the nanoreporter is labeled with one or more light-emitting dyes, each label attachment region containing, directly or indirectly, one or more detectable molecules or label monomers. The light emitted by the dyes can be visible light or invisible light, such as ultraviolet or infrared light. In exemplary embodiments, the dye is a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA™); 6-carboxy-X-rhodamine (ROX™); 6-carboxy-4',5'-dichloro-2',7'-dimethoxyfluorescein (JOE); Alexa Fluor™; Cy2; Texas Red® and Rhodamine Red; 6-carboxy-2',4,7,7'-tetrachlorofluorescein (TET™); 6-carboxy-2',4,4',5',7,7'-hexachlorofluorescein (HEX™); 5-carboxy-2',4',5',7'-tetrachlorofluorescein (ZOE); NAN; NED; Cy3®; Cy3.5®; Cy5®; Cy5.5®; Cy7®; and Cy7.5®; Alexa Fluor® 350; Alexa Fluor® 488; Alexa Fluor® 532; Alexa Fluor® 546; Alexa Fluor® 568; Alexa Fluor® 594; or Alexa Fluor® 647.

The label monomers can be incorporated into a nanoreporter at different stages of its assembly, or into a component (e.g., a complementary RNA nucleotides of the nanoreporter prior to its assembly into the nanoreporter).

A label monomer can be directly attached to a nucleotide using methods well known in the art. Nucleotides can also be chemically modified or derivatized in order to attach a label monomer. For example, a fluorescent monomer such as a fluorescein molecule can be attached to dUTP (deoxyuridine-triphosphate) using a four-atom aminoalkynyl group. Each label monomer is attached to a nucleotide making a label monomer: nucleotide complex.

This label monomer/nucleotide complex can be incorporated into nucleic acids (for example, a DNA patch or a detection oligonucleotide) in a variety of ways. For example, a label monomer/nucleotide complex can be incorporated at only one location within a nucleic acid or at two or more locations within a nucleic acid.

Amine-reactive and thiol-reactive fluorophores are available and used for labeling nucleotides and biomolecules. Generally, nucleotides are fluorescently labeled during chemical synthesis, for example, incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum.

A nucleotide can be attached to a label monomer first and then be incorporated into a nucleic acid. Alternatively, an existing nucleic acid can be labeled by attaching a label monomer to a nucleotide within the nucleic acid. For example aminoallyl-("AA-") modified UTP nucleotides can be incorporated into the RNA product during transcription. In various embodiments, 20% or more of UTP nucleotides in a transcription reaction to generate complementary RNA nucleotides are AA modified. In various embodiments, about 10% or about 20% to 100%, 20% to 80%, 30% to 80%, 40% to 60% or 50% to 75% of UTPs in a transcription reaction are AA-modified, in a preferred embodiment, about 40% or about 50% of UTPs in a transcription reaction are AA-modified.

In addition, for example, different types of label monomer: nucleotide complexes can be incorporated into a single acid nucleic acid, where one component of the nanoreporter code comprises more than one type of signal.

Fluorescent dyes that can be bound directly to nucleotides can also be utilized as label monomers. For example, FAM, JOE, TAMRA, and ROX are amine reactive fluorescent dyes that have been attached to nucleotides and are used in automated DNA sequencing. These fluorescently labeled nucleotides, for example, ROX-ddATP, ROX-ddCTP, ROX-ddGTP and ROX-ddUTP, are commercially available.

Other types of label monomers that may be used to label a nanoreporter are quantum dots. Due to their very small size the quantum dots can be coupled into oligonucleotides directly without affecting the solubility or use of the oligonucleotide. In a preferred embodiment, only one oligonucleotide molecule is coupled to each nanoparticle. To synthesize an oligonucleotide-nanoparticle complex in a 1:1 ratio by conventional batch chemistry, both the oligonucleotide and the nanoparticle require a single reactive group of different kinds that can be reacted with each other. For example, if an oligonucleotide has an amino group and a nanoparticle has an aldehyde group, these groups can react to form a Schiff base. An oligonucleotide can be derivatized to attach a single amino or other functional group using chemistry well known in the art. However, when a nanoparticle is derivatized, it is covered with a chemical reagent which results in coating the entire surface of the nanoparticle with several functional groups.

Affinity Tags

A variety of affinity tags known in the art may be used to purify and/or immobilize nanoreporters.

Where an affinity tag is used to immobilize a nanoreporter for the purpose of detection or imaging, it may be referred to herein as an "anchor." (See FIG. 3). In some embodiments, a biotin anchor is attached to the nanoreporter, allowing immobilization of the nanoreporter on a streptavidin coated slide.

Figure 3A:
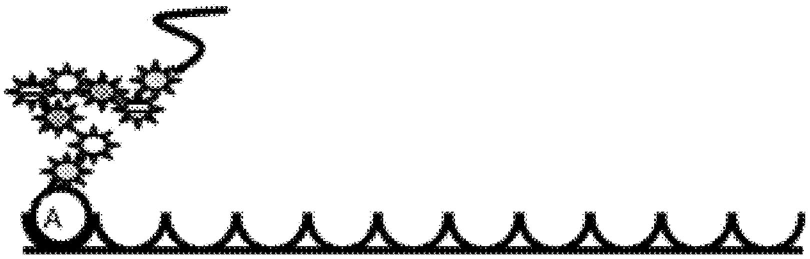
FIG. 3A and FIG. 3B: Show a labeled (nucleic acid-based) nanoreporter with an affinity tag, A1, at one end.
Figure 3B:
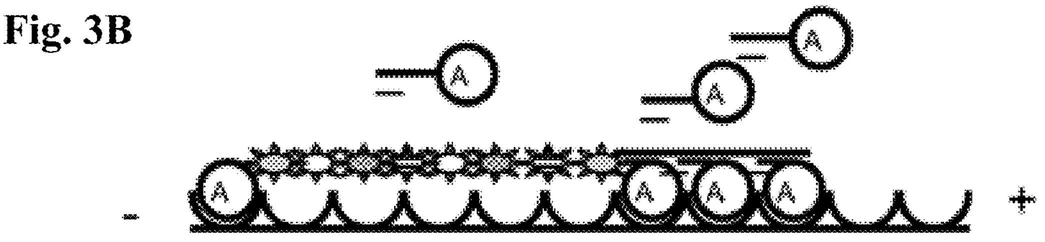

In some embodiments, a labeled nanoreporter will contain an affinity tag at each end, A1 and A2. The labeled nanoreporter can be immobilized to a surface through the binding of A1 to an immobilized affinity partner. In the absence of an affinity binding partner for A2, the A2 end of the nanoreporter remains in solution, but in the presence of an affinity binding partner (A2'), the A2 end of the nanoreporter is also immobilized. In some embodiments, a labeled nanoreporter will contain a single affinity tag, A1. Another affinity tag, A2, can be attached to the nanoreporter by direct binding of the nanoreporter to a molecule containing A2 (e.g., if the nanoreporter is or comprises a nucleic acid, it can hybridize directly with another nucleic acid to which A2 is attached). Alternatively, either affinity tag can be attached to the labeled nanoreporter via a bridging molecule, such as the bridging nucleic acid. FIG. 3 illustrate yet another embodiment in which a labeled (nucleic acid-based) nanoreporter contains an affinity tag, A1, at one end. In FIG. 3, the labeled nanoreporter is immobilized through the binding of A1 to an immobilized affinity partner. The other end of the nanoreporter is in solution (FIG. 3A), but can be immobilized by hybridization to a complementary oligonucleotide which contains another affinity tag (A2) used to immobilize the nanoreporter (FIG. 3B). Upon immobilization of A1, the nanoreporter can be stretched, or "elongated" as depicted in FIG. 3, for example by electrostretching, for separation of the label attachment regions in a manner that permits detection of the nanoreporter code. Optionally, while the nanoreporter is in an elongated state, A2 is introduced and binds the end of the nanoreporter that is complementary to A2 down to the surface.

An affinity tag can be used for attachment to beads or other matrixes for a variety of useful applications including but not limited to purification.

Non-limiting examples of suitable affinity tags are provided below. It should be understood that most affinity tags could serve dual purposes: both as anchors for immobilization of the nanoreporters and tags for purification of the nanoreporters (whether fully or only partially assembled) or their components.

In certain embodiments, the affinity tag is a protein monomer. Examples of protein monomers include, but are not limited to, the immunoglobulin constant regions (see Petty, 1996, Metal-chelate affinity chromatography, in Current Protocols in Molecular Biology, Vol. 2, Ed. Ausubel et al., Greene Publish. Assoc. & Wiley Interscience), glutathione 5-transferase (GST; Smith, 1993, Methods Mol. Cell Bio. 4:220-229), the *E. coli* maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc.

Other affinity tags are recognized by specific binding partners and thus facilitate isolation and immobilization by affinity binding to the binding partner, which can be immobilized onto a solid support. For example, the affinity tag can be an epitope, and the binding partner an antibody. Examples of such epitopes include, but are not limited to, the FLAG epitope, the myc epitope at amino acids 408-439, the influenza virus hemagglutinin (HA) epitope, or digoxigenin ("DIG"). In other embodiments, the affinity tag is a protein or amino acid sequence that is recognized by another protein or amino acid, for example the avidin/streptavidin and biotin.

In certain aspects of the invention, the affinity tag is a nucleotide sequence. A large variety of sequences of about 8 to about 30 bases, more preferably of about 10 to about 20 bases, can be used for purification and immobilization of nanoreporters, and the sequence can be tandemly repeated (e.g., from 1 to 10 tandem repeats). Such a sequence is preferably not widely represented (that is, present in fewer than 5% of the genes, more preferably, present in fewer than 3% of the genes, and, most preferably, present in fewer than 1% of the genes) in the sample being assayed (for example, where the nanoreporter is used for detection of human cellular RNA, the sequence is preferably not widely represented in the human genome); have little or no secondary structure or self-complementarity either internally or with copies of itself when multimerized (that is, all secondary structures of the multimerized tag preferably have a Tm less than 25° C. at 1 M NaCl); have no significant identity or complementarity with backbone or segment sequences (that is, the Tm of complementary sequences is preferably less than 25° C. at 0.2 M NaCl); and have a Tm of about 35-65° C., more preferably about 40-50° C., in 50 mM $Na^+$.

In certain embodiments, different sequences are used as purification and immobilization tags. In this case, for example, the purification tag can be as described above, but the immobilization tag can be in the range of 10 to 100 bases, with a Tm up to 95° C. in 50 mM $Na^+$. An alternative embodiment would be to have the purification tag nested within the immobilization tag (e.g., the affinity tag would comprise a 25-base sequence of which 15 bases are used as a purification tag and the entire 25 bases are used as the immobilization tag).

In certain instances, the affinity tag can be used for labeling a nanoreporter in addition to purifying or immobilizing the nanoreporter.

As will be appreciated by those skilled in the art, many methods can be used to obtain the coding region of the affinity tags, including but not limited to, DNA cloning, DNA amplification, and synthetic methods. Some of the affinity tags and reagents for their detection and isolation are available commercially.

Constant Region

The nanoreporters of the present invention may comprise at least one constant region. A constant region may comprise a polynucleotide sequence. In certain aspects, the polynucleotide sequence of a constant region comprises a plurality of individual repeat nucleotide sequences, such as 2, 3, 4, 5, 6, 7, 8, 9, 10, or more copies of a repeat sequence. In certain aspects, the constant region comprises four copies of a repeat sequence.

In certain embodiments, an individual repeat sequence comprises about 4, 5, 6, 7, 8, 9, 10, 11, 12, 13, 14, 15, 16, 17, 18, 19, 20, 21, 22, 23, 24, 25, 26, 27, 28, 29, 30, or more nucleotide bases. In certain embodiments, an individual repeat sequences comprise about 15 nucleotide bases.

One example of a 15-base repeat sequence is 5'-GGTCTGTGTGATGTT-3' (SEQ ID NO:25). In certain embodiments, the constant region contains four copies of a 15 base repeat, such as the repeat sequence of SEQ ID NO:25.

In certain aspects, the constant region may be ligated to a nanoreporter backbone after isolation and preparation of the backbone polynucleotide sequence, as described herein. In some embodiments, the constant region represents a permanent part of the polynucleotide backbone, as if it were fused to the "coding" sequence of the backbone (i.e., the constant region is cloned into the backbone). In certain embodiments, the constant region is adjacent to a restriction enzyme site for ready incorporation of the selected label attachment regions.

Target-Specific Regions

The term "target-specific sequence" refers to a molecular entity that is capable of binding a target molecule. In the context of a nanoreporter, the target-specific sequence is attached to the nanoreporter backbone.

The target specific sequence is generally an amino acid sequence (i.e., a polypeptide or peptide sequence) or a nucleic acid sequence.

In specific embodiments, where the target-specific sequence is an amino acid sequence, the target-specific sequence may comprise an antibody fragment, such as an antibody Fab' fragment, a single chain Fv antibody.

The target-specific sequence is preferably a nucleic acid sequence, and is most preferably within an oligonucleotide that is either covalently attached (e.g., by ligation) or non-covalently attached (e.g., by hybridization) to the nanoreporter backbone. A target-specific nucleic acid sequence is preferably at least 15 nucleotides in length, and more preferably is at least 20 nucleotides in length. In specific embodiments, the target-specific sequence is about 10 to 500, 20 to 400, 30 to 300, 40 to 200, or 50 to 100 nucleotides in length. In other embodiments, the target-specific sequence is about 30 to 70, 40 to 80, 50 to 90, or 60 to 100, 30 to 120, 40 to 140, or 50 to 150 nucleotides in length.

A target-specific nucleotide sequence preferably has a Tm of about 65-90° C. for each probe in 825 mM $Na^+$ (5×SSC), most preferably about 78-83° C.

In certain preferred embodiments, the target specific sequence of each probe of a dual nanoreporter is about 35 to 100 nucleotides (for a total target sequence of about 70 to 200 nucleotides, covered by 2 probes), most preferably about 40 to 50 nucleotides for each probe (for a total of about 80 to 100 nucleotides).

Target Molecules

The term "target molecule" is the molecule detected or measured by binding of a labeled nanoreporter whose target-specific sequence(s) recognize (i.e., are specific binding partners) thereto. Preferably, a target molecule can be, but is not limited to, any of the following: nucleic acid, peptide, a polypeptide/protein (e.g., a bacterial or viral protein or an antibody), a lipid, a carbohydrate, a glycoprotein, a glycolipid, a small molecule, an organic monomer, or a drug. Nucleic acids that can be analyzed by the methods herein include: double-stranded DNA, single-stranded DNA, single-stranded DNA hairpins, DNA/RNA hybrids, RNA (e.g. mRNA or miRNA) and RNA hairpins. Generally, a target molecule is a naturally occurring molecule or a cDNA of a naturally occurring molecule or the complement of said cDNA.

A target molecule can be part of a biomolecular sample that contains other components or can be the sole or major component of the sample. A target molecule can be a component of a whole cell or tissue, a cell or tissue extract, a fractionated lysate thereof or a substantially purified molecule. The target molecule can be attached in solution or solid-phase, including, for example, to a solid surface such as a chip, microarray or bead. Also the target molecule can have either a known or unknown structure or sequence.

In certain specific embodiments, that target molecule is not a chromosome. In other specific embodiments, the target molecule is no greater than 1,000 kb (or 1 mb) in size, no greater than 500 kb in size, no greater than 250 kb in size, no greater than 175 kb in size, no greater than 100 kb in size, no greater than 50 kb in size, no greater than 20 kb in size, or no greater than 10 kb in size. In yet other specific embodiments, the target molecule is isolated from its cellular milieu.

Biomolecular Samples

The nanoreporter systems of the invention can be used to detect target molecule in any biomolecular sample. As will be appreciated by those in the art, the sample may comprise any number of things, including, but not limited to: biological samples, such as cells (including both primary cells and cultured cell lines), cell lysates, or extracts (including but not limited to RNA extracts; purified mRNA), tissues and tissue extracts (including but not limited to RNA extracts; purified mRNA); bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment, etc.

The biomolecular samples can be indirectly derived from biological specimens. For example, where the target molecule of interest is a cellular transcript, e.g., a messenger RNA, the biomolecular sample of the invention can be a sample containing cDNA produced by a reverse transcription of messenger RNA. In another example, the biomolecular sample of the invention is generated by subjecting a biological specimen to fractionation, e.g., size fractionation or membrane fractionation.

The biomolecular samples of the invention may be either native, e.g., not subject to manipulation or treatment, or treated, which can include any number of treatments, including exposure to candidate agents including drugs, genetic engineering (e.g., the addition or deletion of a gene), etc.

Biomolecular samples may also include environmental samples, such as those containing bacteria or other organisms, such as diatoms, dinoflagellates, algae, among others, such as in certain marine or earth-based samples.

Methods

In certain aspects the invention provides methods for detection and/or quantification of one or more target molecules. In particular, the invention provides stable nanoreporters that are capable of binding individual target molecules, and provide improved detection of target molecules. Through nanoreporters' label codes, the binding of the nanoreporter probes to target molecules results in the identification of the target molecules. The detection and/or quantification can be performed using a single nanoreporter probe system or a dual nanoreporter probe system as described herein.

In some embodiments, the invention provides methods of detecting the presence of a specific target molecule in a biomolecular sample comprising contacting the sample with a nanoreporter probe as described herein under conditions that allow binding of the target-specific sequences in the probes to a target molecule in the sample, and detecting the signal associated with the uniquely labeled nanoreporter probe. In some embodiments, the biomolecular sample is a biological sample. In some embodiments, the biological sample is selected from a cell, a cell lysate, a tissue sample, a tissue extract, or a bodily fluid. In some embodiments, the biomolecular sample is an environmental sample.

In some embodiments, the invention provides methods of detecting the presence of a plurality of specific target molecules in a biomolecular sample comprising contacting the sample with a plurality of nanoreporter probes as described herein under conditions that allow binding of the target-specific sequences in the probes to a target molecule in the sample, and detecting the signal associated with the uniquely labeled nanoreporter probes.

In some embodiments, the invention provides methods for determining the presence of at least one target molecule in a sample, comprising forming at least one molecular complex comprising (a) at least one target molecule and (b) at least one nanoreporter probe comprising a unique target-specific region and a region comprising a unique, designed nanoreporter wherein said nanoreporter comprises a plurality of different detectable molecules, and individually detecting said at least one molecular complex or at least part of said at least one molecular complex to determine the presence of at least one target molecule in the sample by a method comprising individually counting the presence of one or more nanoreporter molecules. In some embodiments the methods of the invention provides for determining the presence of a plurality of target molecules by a method comprising forming a plurality molecular complexes, each complex comprising (a) at least one target molecule and (b) at least one nanoreporter probe comprising a unique target-specific region and a region comprising a unique, designed nanoreporter, wherein each nanoreporter comprises a plurality of different detectable molecules; and wherein each nanoreporter probe comprises a different nanoreporter region. In some embodiments, the number of molecular counts above background of said molecular complex after normalization of the sample is higher than 300, 400, 450, 500, 600, 700, 800, 900 or 1000 molecular counts. In some embodiments, the number of molecular counts above background of the molecular complex after normalization of the sample is higher than 400 molecular counts. In some embodiments, the percentage of valid molecular counts of the nanoreporter probes is higher that about 10, 11, 12, 12.5, 14, 15, 20, 25, 30, 35, 40, 50, 60, 70, 80 or 90%. In some embodiments, the percentage of valid molecular counts of the nanoreporter probes is higher that about 12.5%. In some embodiments, the number of molecular counts above background of the nanoreporter described herein after normalization of said sample is at least 6 fold higher than a comparable nanoreporter comprising M13 DNA. In some embodiments, the number of molecular counts above background of the nanoreporter described herein after normalization of said sample is at least 2 fold higher than a comparable nanoreporter comprising M13 DNA.

In some embodiments, the invention provides methods for determining the presence of at least one target molecule in a sample, comprising (1) forming at least one molecular complex comprising (a) at least one target molecule and (b) at least one probe comprising a unique target-specific region and a region comprising a unique, designed nanoreporter, wherein said nanoreporter comprises a single-stranded nucleic acid backbone, said backbone comprising a plurality of label attachment regions covalently attached together in a unique linear combination, wherein each label attachment region is hybridized to a unique complementary polynucleotide sequence having attached thereto one or more detectable molecules, and (2) individually detecting the at least one molecular complex or at least part of said at least one molecular complex to determine the presence of at least one target molecule in the sample. In some embodiments, the percentage of valid molecular counts of the nanoreporter probes is higher that about 10, 11, 12, 12.5, 14, 15, 20, 25, 30, 35, 40, 50, 60, 70, 80 or 90%. In some embodiments, the percentage of valid molecular counts of the nanoreporter probes is higher that about 12.5%.

In some embodiments, the number of molecular counts above background of the nanoreporter described herein after normalization of said sample is at least 2 fold higher than a nanoreporter comprising M13 DNA. In some embodiments, the Tm of the complementary polynucleotide sequences when hybridized to its label attachment regions are higher than the Tm of a polynucleotide sequences complementary to a M13 DNA template when hybridized to a nanoreporter probe comprising the M13 DNA; The M13 nanoreporter probe comprises the same target specific sequence of the nanoreporter probe, and comprises a single-stranded backbone comprising a plurality of M13 DNA regions covalently attached together wherein each region is hybridized to a complementary polynucleotide sequence having attached thereto one or more detectable molecules. In some embodiments, the invention provide methods of determining the presence of a plurality of target molecules by a method comprising forming a plurality molecular complexes, each complex comprising (a) at least one target molecule and (b) at least one nanoreporter probe, where each nanoreporter probe has a higher melting temperature than a comparable nanoreporter comprising M13 DNA.

Examples of specific embodiments of the invention are shown in FIG. 1 and FIG. 2.

In addition to detecting an overall signal generated from a labeled nanoreporter, the invention provides for the determination of the spatial location of signals emanating from the label monomers (e.g., spots) on a nanoreporter, each spot representing the aggregate signal from label monomers attached to a given label attachment region. A spot may contain signals of the same wavelength or of different wavelengths. Thus, the nature of the spots on a nanoreporter and their location constitutes the nanoreporter code.

Figure 4A:
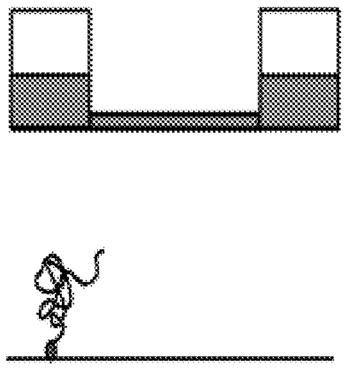
FIG. 4A to FIG. 4C.
Figure 4B:
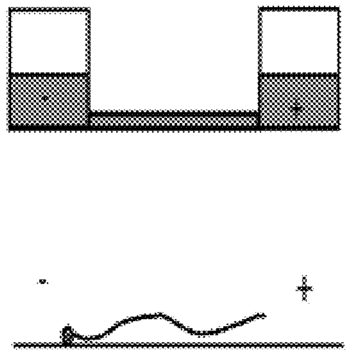
Figure 4C:
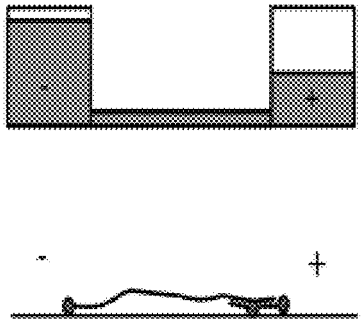

In some embodiments, the label nanoreporter is captured and stretched in a location (See FIG. 4). In some embodiments, prior to stretching a nanoreporter, the nanoreporter is immobilized to a solid surface using an affinity tag, as described above (See FIG. 3). In certain aspects of the invention, one end of a nanoreporter is immobilized, either through specific or non-specific binding to a solid surface, the nanoreporter is stretched, and then the other end of the reporter is immobilized, also either through specific or non-specific binding to a solid surface (See FIG. 3). Methods for capturing, stretching and immobilization of nucleic acids are well known in the art. Examples of methods that can be used in the methods described herein are described in U.S. Pat. No. 7,473,767 entitled "Methods for detection and quantification of analytes in complex mixtures", US patent publication no. 2007/0166708 entitled "Methods for detection and quantification of analytes in complex mixtures", U.S. application Ser. No. 11/645,270 entitled "Compositions comprising oriented, immobilized macromolecules and methods for their preparation", PCT application no U.S. Ser. No. 06/049,274 entitled "Nanoreporters and methods of manufacturing and use thereof", and U.S. provisional application 60/088,988 entitled "Stable nanoreporter", all of which are incorporated by reference herein in its entirety.

Thus, in some embodiments, the nanoreporter is "frozen" in its stretched, or extended, state, to facilitate resolution of the nanoreporters code by detecting and/or imaging the signals provided (e.g., emitted) by the label monomers attached to a nanoreporter and their locations relative to one another. These aspects of the invention are described in U.S. Pat. No. 7,473,767 entitled "Methods for detection and quantification of analytes in complex mixtures", US patent publication no. 2007/0166708 entitled "Methods for detection and quantification of analytes in complex mixtures", U.S. application Ser. No. 11/645,270 entitled "Compositions comprising oriented, immobilized macromolecules and methods for their preparation", PCT application no U.S. Ser. No. 06/049,274 entitled "Nanoreporters and methods of manufacturing and use thereof", and U.S. provisional application 60/088,988 entitled "Stable nanoreporter", all of which are incorporated by reference herein in its entirety.

In some embodiments, the nanoreporter can be immobilized to the substrate. In the methods of the invention, the substrate for immobilization can be any substrate capable of selectively binding the nanoreporter apparent to those of skill in the art. In some embodiments, a first portion of the nanoreporter can be immobilized to the substrate via an avidin-biotin binding pair. In certain embodiments, the nanoreporter can comprise a biotin moiety in its first portion. For instance, a polynucleotide nanoreporter can comprise a biotinylated nucleotide residue. In a dual nanoreporter probe system, one of the nanoreporter probes (e.g. capture nanoreporter probe) can comprise a biotin moiety. This probe might be labeled or unlabeled. In preferred embodiments, when a dual nanoreporter system is used, the nanoreporter probe comprising a biotin moiety is unlabeled. The substrate comprising avidin can be any substrate comprising avidin known to those of skill in the art. Useful substrates comprising avidin are commercially available including TB0200 (Accelr8), SAD6, SAD20, SAD100, SAD500, SAD2000 (Xantec), SuperAvidin (Array-It®), streptavidin slide (catalog #MPC 000, Xenopore) and STREPTAVIDINnslide (catalog #439003, Greiner Bio-one).

In certain embodiments, the first portion of the nanoreporter can comprise a nucleotide sequence that is capable of selectively binding a nucleotide sequence on the substrate (e.g. biotin). In certain aspects, the constant region (e.g., multiple copies of a 15-base repeat sequence) of the nanoreporter is capable of selectively binding a complementary polynucleotide sequence that is immobilized on the substrate. In a specific embodiment, if the nanoreporter comprises four copies of the exemplary 15-base repeat sequence of 5'-GGTCTGTGTGATGTT-3' (SEQ ID NO:25), an oligonucleotide having the sequence 5'-AACATCACACA-GACC AACATCACACAGACC AACATCACACAGACC AACATCACACAGACC AGCCCTTTG-3' (SEQ ID NO:26) may be utilized to immobilize the nanoreporter to a substrate.

In some embodiments where a dual nanoreporter probe system is used, a first unlabeled capture nanoreporter probe comprising biotin and a second labeled nanoreporter probe comprising a constant region are used for the detection and/or quantification of a target molecule (See FIG. 1 and FIG. 2). Both nanoreporter probes bind to the target molecule via their target specific sequence forming a complex comprising the target molecule and the nanoreporter probes. The complex is then captured and immobilized into an avidin containing substrate such as the ones described herein. The complex can then be stretched and extended as described herein. The constant region in the nanoreporter probe can then be bound to a complementary polynucleotide sequence that is immobilized on the substrate. Examples of methods that can be used in the methods described herein with respect to dual nanoreporter systems are described in PCT application no U.S. Ser. No. 06/049,274 entitled "Nanoreporters and methods of manufacturing and use thereof", and U.S. provisional application 60/088,988 entitled "Stable nanoreporter", all of which are incorporated by reference herein in its entirety.

Examples of specific embodiments of the invention are shown in FIG. 2 to FIG. 4.

In certain aspects, the invention provides methods for preparing a suitable population of unique nucleic acid backbones, comprising (a) selecting a set of label attachment regions from a library of unique, designed label attachment regions, and (b) covalently attaching the set of label attachment regions to each other in a linear combination that is different from the other backbones in the population, and repeating steps (a)-(b) until a suitable population of unique nucleic acid backbones has been prepared. In some embodiments the label attachment regions comprise about 800 to 1300 nucleotide bases. In some embodiments the label attachment regions have a G/C content of about 50%. In some embodiments, adenine bases are spaced on average at about every 8 to 16 bases in the label attachment regions. In some embodiments, the label attachment regions are devoid of secondary structures. In some embodiments, each selected label attachment region is different from the other selected label attachment regions in the set. In some embodiments, the selecting step (a) comprises selecting a set of 3, 4, 5, 6, 7, 8 label attachment regions. In some embodiments, the selecting step (a) comprises selecting a set of 6 label attachment regions. In some embodiments, the label attachment regions are hybridized to a complementary RNA polynucleotide having attached thereto a detectable molecule. In some embodiments, the complementary RNA polynucleotide has a G/C ratio of at least 1/1. In some embodiments, the complementary RNA polynucleotide has a G/C ratio of about 3/2.

In certain aspects, the invention provides methods for preparing a suitable population of unique nucleic acid backbones, comprising (a) selecting a set of label attachment regions from a library of unique, designed label attachment regions, wherein each label attachment region comprises about 800 to 1300 nucleotide bases and has a G/C content of about 50%, wherein each label attachment region comprises a regularly-spaced pattern of adenine bases, and (b) covalently attaching the set of label attachment regions to each other in a linear combination that is different from the other backbones in the population, and repeating steps (a)-(b) until a suitable population of unique nucleic acid backbones has been prepared. In some embodiments, adenine bases are spaced at about every 8 to 16 bases in the label attachment regions. In some embodiments, the label attachment regions are devoid of secondary structures. In some embodiments, each selected label attachment region is different from the other selected label attachment regions in the set. In some embodiments, the selecting step (a) comprises selecting a set of 3, 4, 5, 6, 7, 8 label attachment regions. In some embodiments, the selecting step (a) comprises selecting a set of 6 label attachment regions. In some embodiments, the label attachment regions are hybridized to a complementary RNA polynucleotide having attached thereto a detectable molecule. In some embodiments, the complementary RNA polynucleotide has a G/C ratio of about 3/2.

Methods of Using Selectively Immobilized, Extended, or Oriented Nanoreporters

In certain embodiments, the invention provides selectively immobilized, elongated nanoreporters that can be used to create macromolecular barcodes for the purposes of separation and sequential detection of labels. These labels spaced along the molecule provide a unique code that can be read when the nanoreporter is extended and immobilized. Extension and selective immobilization can facilitate the decoding of the macromolecular barcode.

The selectively immobilized, elongated nanoreporters can be used in any context where detection or imaging of a nanoreporter might be useful. They can be used for diagnostic, prognostic therapeutic and screening purposes. For instance, they can be applied to the analysis of biomolecular samples obtained or derived from a patient so as to determine whether a diseased cell type is present in the sample and/or to stage the disease. They can be used to diagnose pathogen infections, for example infections by intracellular bacteria and viruses, by determining the presence and/or quantity of markers of bacterium or virus, respectively, in the sample. The compositions and methods of the invention can be used to quantitate target molecules whose abundance is indicative of a biological state or disease condition, for example, blood markers that are upregulated or downregulated as a result of a disease state. In addition, the compositions and methods of the invention can be used to provide prognostic information that assists in determining a course of treatment for a patient.

Detection of Nanoreporters

Nanoreporters are detected by any means available in the art that is capable of detecting the specific signals on a given nanoreporter. Where the nanoreporter is fluorescently labeled, suitable consideration of appropriate excitation sources may be investigated. Possible sources may include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to determine the sequence of the spots on the nanoreporter. For example in one embodiment an image of a dual nanoreporter hybridized to a target molecule can be obtained. If for example, the nanoreporters are labeled with three different colors, Alexa 488, Cy3 and Alexa 647 (labeled 1, 2 and 3, respectively). Colors 1, 2 and 3 are each acquired in different channels and the first and second registers, which can be seen as rows of spots, are shifted up by several pixels to be able to show each register individually.

Examples of methods for detection of nanoreporters that can be used in the methods of the invention are described in U.S. Pat. No. 7,473,767 entitled "Methods for detection and quantification of analytes in complex mixtures", US patent publication no. 2007/0166708 entitled "Methods for detection and quantification of analytes in complex mixtures", U.S. application Ser. No. 11/645,270 entitled "Compositions comprising oriented, immobilized macromolecules and methods for their preparation", PCT application no U.S. Ser. No. 06/049,274 entitled "Nanoreporters and methods of manufacturing and use thereof", and U.S. provisional application 60/088,988 entitled "Stable nanoreporter", all of which are incorporated by reference herein in its entirety.

Microscope and Objective Lens Selection

The major consideration regarding the microscope objective lens is with the optical resolution, which is determined by its numerical aperture (NA). Generally, the larger the NA, the better the optical resolution. The required NA is preferably at least 1.07 based on the relationship of $\delta=0.61\lambda/NA$ ($\delta$=optical resolution and $\lambda$=wavelength). The amount of light that is collected by an objective is determined by $NA^4/Mag^2$ (Mag=magnification of the objective). Therefore, in order to collect as much light as possible, objectives with high NA and low magnifications should be selected.

CCD Camera Selection and Image Capture Techniques

When selecting a CCD camera, the first consideration is the pixel size, which partially determines the final resolution of the imaging system. Optimally the optical resolution should not be compromised by the CCD camera. For example, if the optical resolution is 210-300 nm, which corresponds to 12.6-18 μm on a CCD chip after a 60× magnification, in order to resolve and maintain the optical resolution there should be at least two pixels to sample each spot. Or the pixel size of the CCD chip should be at most 6.3-9 μm.

The second consideration is detection sensitivity which can be determined by many factors that include but are not limited to pixel size, quantum efficiency, readout noise and dark noise. To achieve high sensitivity, select a qualitative camera with big pixel size (which can give big collection area), high quantum efficiency and low noise. An exemplary camera with these criteria is the Orca-Ag camera from Hamamatsu Inc. The chip size is 1344×1024 pixels; when using the 60× objective, the field of view is $144\times110\ \mu m^2$.

Applications of Nanoreporter Technology

The compositions and methods of the invention can be used for diagnostic, prognostic therapeutic and screening purposes. The present invention provides the advantage that many different target molecules can be analyzed at one time from a single biomolecular sample using the methods of the invention. This allows, for example, for several diagnostic tests to be performed on one sample.

The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. In some embodiments, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science. Examples of genetic analyses that can be performed on nucleic acids include e-g., SNP detection, STR detection, RNA expression analysis, promoter methylation, gene expression, virus detection, viral subtyping and drug resistance.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Diagnostic/Prognostic Methods

The present methods can be applied to the analysis of biomolecular samples obtained or derived from a patient so as to determine whether a diseased cell type is present in the sample and/or to stage the disease.

In some embodiments, the methods described herein are used in the diagnosis of a condition. As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a blood sample can be assayed according to any of the methods described herein to determine the presence and/or quantity of markers of a cancerous cell type in the sample, thereby diagnosing or staging the cancer.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Alternatively, the methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella*, Clostridia, *Bordetella pertussis, Bacteroides, Staphylococcus aureus, Streptococcus pneumonia*, B-Hemolytic strep., Corynebacteria, *Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes.*

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes* (*Rhizopus*), *Sporothrix schenckii, Chromomycosis*, and *Maduromycosis.*

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii*, and *Necator americanis.*

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention Thus, the target molecules detected using the compositions and methods of the invention can be either patient markers (such as a cancer marker) or markers of infection with a foreign agent, such as bacterial or viral markers.

Because of the quantitative nature of nanoreporters, the compositions and methods of the invention can be used to quantitate target molecules whose abundance is indicative of a biological state or disease condition, for example, blood markers that are upregulated or downregulated as a result of a disease state.

In addition, the compositions and methods of the invention can be used to provide prognostic information that assists in determining a course of treatment for a patient. For example, the amount of a particular marker for a tumor can be accurately quantified from even a small sample from a patient. For certain diseases like breast cancer, overexpression of certain genes, such as Her2-neu, indicate a more aggressive course of treatment will be needed.

Analysis of Pathology Samples

RNA extracted from formaldehyde- or paraformaldehyde-fixed paraffin-embedded tissue samples is typically poor in quality (fragmented) and low in yield. This makes gene expression analysis of low-expressing genes in histology samples or archival pathology tissues extremely difficult and often completely infeasible. The nanoreporter technology can fill this unmet need by allowing the analysis of very small quantities of low-quality total RNA.

To use nanoreporter technology in such an application, total RNA can be extracted from formaldehyde- or paraformaldehyde-fixed paraffin-embedded tissue samples (or similar) using commercially available kits such as RecoverAll™ Total Nucleic Acid Isolation Kit (Ambion) following manufacturer's protocols. RNA in such samples is frequently degraded to small fragments (200 to 500 nucleotides in length), and many paraffin-embedded histology samples only yield tens of nanograms of total RNA. Small amounts (5 to 100 ng) of this fragmented total RNA can be used directly as target material in a nanoreporter hybridization following the assay conditions described herein.

Screening Methods

The methods of the present invention can be used, inter alia, for determining the effect of a perturbation, including chemical compounds, mutations, temperature changes, growth hormones, growth factors, disease, or a change in culture conditions, on various target molecules, thereby identifying target molecules whose presence, absence or levels are indicative of particular biological states. In a preferred embodiment, the present invention is used to elucidate and discover components and pathways of disease states. For example, the comparison of quantities of target molecules present in a disease tissue with "normal" tissue allows the elucidation of important target molecules involved in the disease, thereby identifying targets for the discovery/screening of new drug candidates that can be used to treat disease.

Kits Comprising Nanoreporters

The invention further provides kits comprising one or more components of the invention. The kits can comprise, for example, a substrate according to the invention and one or more extended or oriented, or both, nanoreporters selectively immobilized on the substrate. The kits can be used for any purpose apparent to those of skill in the art, including those described above.

In certain embodiments, the invention provides kits for preparing at least one uniquely labeled nanoreporter comprising at least three label attachment regions each comprising about 800 to 1300 nucleotide bases, a G/C content of about 50%; and at least three complementary polynucleotide sequences having attached thereto a detectable molecule, wherein the complementary polynucleotide sequences have a G/C ratio of at least 1/1. In some embodiments, the complementary polynucleotide sequences have a G/C ratio of about 3/2. The kit can further comprise at least three target specific probes.

In certain embodiments, the present invention also provides kits useful for the extension and selective immobilization of nanoreporters. The kits can comprise a substrate for immobilization and one or more binding partners to facilitate extension or immobilization of a nanoreporter. The binding partners could, in certain embodiments, comprise a moiety useful for extension of the nanoreporter in an appropriate force. In certain embodiments, the binding partners could facilitate immobilization or selective immobilization of the nanoreporter to the surface. In further embodiments, the kit could comprise a nanoreporter for extension and immobilization. In further embodiments, the kit could comprise a device capable of extending the nanoreporter.

The kits can contain a population of nanoreporters as described herein.

The kits can contain pre-labeled nanoreporters, or unlabeled nanoreporters with one or more components for labeling the nanoreporters. Moreover, the nanoreporters provided in a kit may or may not have target-specific sequences pre-attached. In one embodiment, the target sequences are provided in the kit unattached to the nanoreporter backbone.

The kit can include other reagents as well, for example, buffers for performing hybridization reactions, linkers, restriction endonucleases, and DNA I ligases.

The kit also will include instructions for using the components of the kit, and/or for making and/or using the labeled nanoreporters.

The present invention may be further understood by the non-limiting examples provided below.

EXAMPLES

Example 1

Design and Manufacturing Protocol for a De Novo 1 (DV1) Nanoreporter Backbone Library To construct a library of diverse Nanoreporter backbones, label attachment regions were selected from a library of unique, rationally designed polynucleotide sequences and cloned in various combinations into a plasmid vector having the polynucleotide sequence set forth in SEQ ID NO:27. This vector sequence does not end up in the final reporter backbone, but is utilized for cloning and propagating the backbone sequences.

Specifically, each unique, code-specific DV1 plasmid was constructed of six approximately 1100 base pair label attachment regions, which were selected from the polynucleotide sequences of SEQ ID NOS: 1-24. The label attachment regions defined by these polynucleotide sequences were cloned in various combinations into the vector of SEQ ID NO:27, each label attachment region corresponding to a fixed position on a given backbone, i.e., position 1, position 2, through position 6. The label attachment regions at each position in a given backbone were different from the other label attachment regions in that same backbone. The 3' end of each position-6 sequence was cloned next to 4 copies of a common 15-base repeat known as the G-4 repeat (SEQ ID NO:26), used in purification and immobilization of the reporters. 972 nanoreporter backbones, each having a unique linear combination of label attachment regions, were designed and cloned according to routine molecular biological techniques.

When each label attachment region is assigned one of four detectable molecules, the use of six-label attachment regions in a four-color reporter system provides a possible 4096 unique nanoreporters. In this Example, SEQ ID NOS: 1, 5, 9, 13, 17, and 21 were assigned a blue fluorophore, SEQ ID NOS: 2, 6, 10, 14, 18, and 22 were assigned a green fluorophore, SEQ ID NOS: 3, 7, 11, 15, 19, and 23 were assigned a yellow fluorophore, and SEQ ID NOS: 4, 8, 12, 16, 20, and 24 were assigned a red fluorophore. Thus, in this Example, even if a given backbone comprises 6 label attachment regions assigned a blue fluorophore (e.g., SEQ ID NOS: 1, 5, 9, 13, 17, and 21 in positions 1-6), each individual label attachment region would have a different polynucleotide sequence than the other label attachment regions in that same backbone.

The individual plasmids were amplified in bacteria, isolated, and converted into linear, single-stranded backbones. Specifically, linear single-stranded DNA backbones were made from a double stranded plasmid DNA using a four step protocol: (i) dsDNA was linearized with a restriction enzyme, (ii) linearized DNA was dephosphorylated with a thermolabile phosphatase, (iii) the DNA was digested with a second restriction enzyme to separate the cloning vector from the backbone sequence, and (iv) the mixture was digested with a strand-specific lambda exonuclease digestion, leaving only one strand of the backbone fragment intact.

The single stranded backbones were ligated to target-specific nucleotide sequences and incubated with dye-colored complementary RNA nucleotide sequences to make labeled nanoreporters.

Example 2

Generating Dye-Colored Complementary RNA Polynucleotides

In vitro transcription (IVT) reactions were utilized to generate amino-allyl modified complementary RNA polynucleotides using MEGAscript T3, T7 or SP6 kits (Ambion®), following the manufacturer's instructions with the following specifics and modifications.

Plasmids containing an RNA polymerase promoter and the polynucleotide sequence of interest were linearized by restriction digestion, ethanol-precipitated and used as templates. In this example, the sequences set forth in SEQ ID NOS:1-24 were used as templates in the IVT reaction, generating 24 unique complementary RNA polynucleotides.

Amino-allyl-UTP (aaUTP) (Fermentas) was substituted for the UTP supplied in the kit, or a mixture of aaUTP and the supplied UTP was used. The level of dye-incorporation in a complementary RNA polynucleotide correlates with the number of possible amino-allyl (aa) attachment sites. To make the brightest possible colored segments, 100% aaUTP should be used. To change the brightness, a mixture of aaUTP and unmodified UTP in any ratio can be used in the IVT reactions to modify the number of aa sites present on a complementary RNA polynucleotide. For example, to incorporate dyes at 50% of the regularly repeated base, a 1:1 mixture of aaUTP and UTP was utilized. The final concentration of aaUTP+UTP together was the same as that of each of the other three nucleotides (i.e., ATP, CTP, GTP).

The IVT reaction was allowed to proceed at 37° C. for 22 hours. Following the reaction, the amino-allyl modified RNA transcripts were purified using an RNeasy® kit (Qiagen™) following the manufacturer's instructions.

The dye coupling reaction described below is for a 1 mg reaction Ethanol-precipitation was performed on 1 mg of an amino-allyl (aa) modified RNA polynucleotide. Solid dyes (Alexa 488 TFP ester, Alexa 546 succinimidyl ester, Alexa 594 succinimidyl ester, and Alexa 647 succinimidyl ester; Invitrogen) were resuspended at 11 μg/μl in anhydrous DMSO. The aa-modified RNA polynucleotides were resuspended in a final volume of 90 ul of 100 mM $Na_2B_4O_7$ pH 8.5, and heated to 37° C. for 20 min. 110 μl of the resuspended dyes were individually mixed with 90 μl of an aa-modified RNA polynucleotide. The mixture was incubated in the dark at room temperature for 30 min-2 hr.

The dye-colored, aa-modified RNA polynucleotides were purified from the mixture using an RNeasy kit (Qiagen®) following the manufacturer's instructions. Equal amounts of each of the 24 dye-colored RNA polynucleotides were mixed for a final concentration of 40 nM of each polynucleotide ("color segment mix"). This mixture may be combined with a population of nanoreporter backbones to generate a population of unique nanoreporters, as described in Example 3 below.

Example 3

Generating a Labeled DV1 Nanoreporter Library

To produce a library of labeled DV1 Nanoreporter molecules, each code-specific DNA backbone from Example 1 was ligated separately to a probe region, i.e., target-specific nucleotide sequence, for a specific gene of interest. The probe was ligated to the backbone via an oligonucleotide, which serves as a bridge between the backbone and the specific probe. Specifically, a master mix containing a universal oligonucleotide that served as a ligation "bridge" plus ligase buffer was added to individual wells of 96-well plates containing normalized (10 μM) target-specific oligonucleotide probes (35-50 bases). After a short incubation at 37° C. to anneal the probe oligonucleotide to the complementary portion of the bridge oligonucleotide, ligation was initialized by addition of 1.2 pmoles of individual single-stranded nanoreporter backbone per well, additional ligation buffer, and T4 ligase. Plates were incubated at 37° C. in a 96-well thermocycler for 2 h. Ligation reactions were desalted via centrifugation through G-50 Sephadex columns in a 96-well format. The individual ligated backbones were pooled, ethanol-precipitate, and resuspended in 10 mM Tris pH 8.0 at 20 nM.

To produce dye-labeled nanoreporters, the following was mixed: 2 ml 20×SSPE pH 6.5, 28.05 ml H2O, 5 ml pooled DV1 nanoreporter backbones from above, 1.2 ml ethanol, and 3.75 ml colored segment mix from Example 2. The mixture was incubated at 75° C. for 2 hours. To remove excess segments, the mixture was purified over an oligonucleotide column coupled to the reverse complement of the G-repeat sequence common to all of the backbone sequences (see SEQ ID NO: 26 for the reverse complement sequence). To produce unlabeled "capture" probes, the nanoreporter backbones were biotinylated near or at the 3' region.

Example 4

Comparison of DV1 and M13 Nanoreporter Systems

A 40-gene DV1 reporter library was made as described in Examples 1 to 3, and a comparable M13 library was also made, as described in U.S. application Ser. No. 12/100,990, herein incorporated by reference. The DV1 and M13 libraries contained identical probe (i.e., target-specific nucleotide) sequences and were used to assay the same samples—36 cell lysates, assayed in triplicate. Standard hybridization, purification and imaging protocols were followed, as described in Geiss et al., *Nature Biotechnology* 26:317-324, 2008, herein incorporated by reference in its entirety. Generally, nanoreporter libraries were hybridized to RNA-containing cell lysates, excess reporters were removed by washing, reporters were bound to a surface upon which the reporters were immobilized and stretched, the surface was imaged, and the images were analyzed.

Hybridization Reactions

Detection of cellular transcripts was carried out in multiplexed hybridization reactions, which utilized a dual nanoreporter system having both labeled nanoreporter probes and unlabeled nanoreporter probes, i.e., "capture" probes. Each sample was hybridized in triplicate with final concentrations of the hybridization reagents as follows: 200 ρM each unlabeled, biotinylated capture probe (capture probe), 40 pM each labeled reporter probe, 5×SSPE (pH 7.5), 5×Denhardt's reagent (Sigma), 100 ng/μl sheared salmon sperm DNA (Sigma), and 0.1% Tween-20. Each 30 μl hybridization reaction also contained 100 ng total RNA at a final concentration of 3.3 ng/μl. Reagents were mixed and incubated at 65° C. in a thermocycler block with a heated lid for 20 hours.

Post-hybridization Purification

To remove unhybridized reporters, reactions were purified over magnetic beads (Invitrogen™) coupled to oligonucleotides complementary to the 3'-repeat sequence contained on every capture probe. Reactions were first diluted to 1×SSPE in 0.1% Tween-20/TE and allowed to bind to beads at 22.5° C. for 30 minutes with continuous rotation. The beads were washed three times in 150 μl of 0.1×SSPE/0.1% Tween-20 and the hybridized complexes eluted in 100 μl of 0.1×SSPE/0.1% Tween-20 for 15 minutes at 45° C. After elution, samples were purified a second time to remove excess capture probes by binding to magnetic beads coupled to oligonucleotides complementary to the 5'-repeat sequence contained on every reporter probe. The elutions from the anti-3'-repeat beads were brought to a final concentration of 1×SSPE by addition of 50 μl of 3×SSPE/0.1% Tween-20 and bound for 15 minutes at 22.5° C. with rotation. Beads were washed as above and eluted in 30 μl of 0.1×SSPE/0.1% Tween-20 at 45° C. The doubly-purified samples were then prepared for capture as described below.

NanoString Reporter Capture, Stretching, and Imaging

One microliter of 1/5000 dilution of a 0.1% solids solution of a custom-formulation of Tetraspeck fluorescent microspheres (Invitrogen™) was added to each sample. Samples were loaded into a NanoString fluidic device made by lamination of laser-machined cast acrylic with a coverslip coated with streptavidin (Optichem®, Accelr8 Technology Corporation) using a laser-cut double-sided adhesive layer (Fralock) to generate 30i.tm deep microfluidic channels. The samples were driven through the channel by hydrostatic pressure and bound specifically by the biotinylated 3' end of the capture probe. After capture, the surface was washed once with 90 μl of 1×TAE and prepared for stretching by the addition of 40 μl of TAE to each well. Reporter probes were stretched and aligned by applying 160V/cm for 1 minute along the fluidic channel. Stretched reporters were then immobilized to the surface by addition of 60 μl of a 500 nM solution of a biotinylated oligonucleotide complementary to the 5'-repeats present on the 5' end of all reporter probes. The current remained on for 5 minutes, throughout the immobilization process. After immobilization, the TAE solution was removed and replaced with a custom formulation of the anti-photobleaching reagent SlowFade (Invitrogen) for imaging.

Slides were imaged on a Nikon Eclipse TE2000E equipped with Perfect Focus, a 1.4 NA Plan Apo VC 60X oil-immersion lens (Nikon), an X-cite 120 metal halide light source (Exfo Corporation), an automated H117 stage (Prior Scientific), and a SmartShutter (Sutter Instrument). For each field of view, 4 images at different excitation wavelengths (480, 545, 580 and 622) were acquired with an Orca Ag CCD camera (Hamamatsu) under control of either Metamorph (Universal Imaging Corporation) or custom software.

Image Processing

Image processing was performed on 4 images (one for each wavelength) on a FOV-by-FOV basis.

The custom algorithm treats each FOV as a fundamental block in which the following basic steps are performed: 1) spot identification, 2) image registration, 3) spatial clustering to produce strings, and 4) string classification.

In the first step of the algorithm, spots were identified. The background intensity level of each channel was computed and used to threshold the image into signal and background, where signal regions are the result of a specific wavelength of light observed as a point spread function (PSF). The signal mask was segmented using a custom Watershed algorithm. The segmented regions were then labeled, parameterized, and filtered to remove non-PSF spots. The remaining spots were centrally archived for use in registration and reporter calling.

Image registration was performed on each FOV based on archived spots that correspond to fluorescent beads (fiducials) that were bound to the imaging surface (see NanoString reporter capture, stretching, and imaging). The archived spots were cross-referenced to identify inter-channel clusters of spots that meet fiducial requirements (inter-channel intensity thresholds and ratios). Clusters that met requirements were archived as fiducials. The final list of fiducials represented the spatial transforms that occurred between channels during image acquisition. Spatial offsets were as large as 5-6 pixels. The spatial transform was solved for using the observed fiducial centroids and their pre transform (assumed) coincident centroids ($X_2=X_1*T$). The inverse transform was then applied to all identified spots to restore their original centroids.

After spot identification and image registration, spots were assembled into "strings" via clustering. At this point, each string was filtered to remove any spots attributed to bleed-though signal. The filtered strings were then classified as reporters or non-reporters. To be classified as a reporter the string must contain the correct number of spots, meet specific spot-to-spot spacing thresholds (1.2-2.9 pixels), and meet acceptable linearity and orientation requirements. Clusters that were classified as reporters were then counted and summed for each gene over all FOVs.

NanoString Data Normalization and Analysis

To account for slight differences in hybridization and purification efficiency, data was normalized to the average counts for all control spikes in each sample. To determine if a gene was "detected" by the NanoString system, the triplicate measurements obtained for each experimental gene were compared to triplicate measurements for the negative controls. For a gene to be categorized as detected, the average counts for the experimental gene had to be greater than the average counts for the 2 negative controls, and the Student's T-test P-value had to be less than 0.05.

Figure 5:
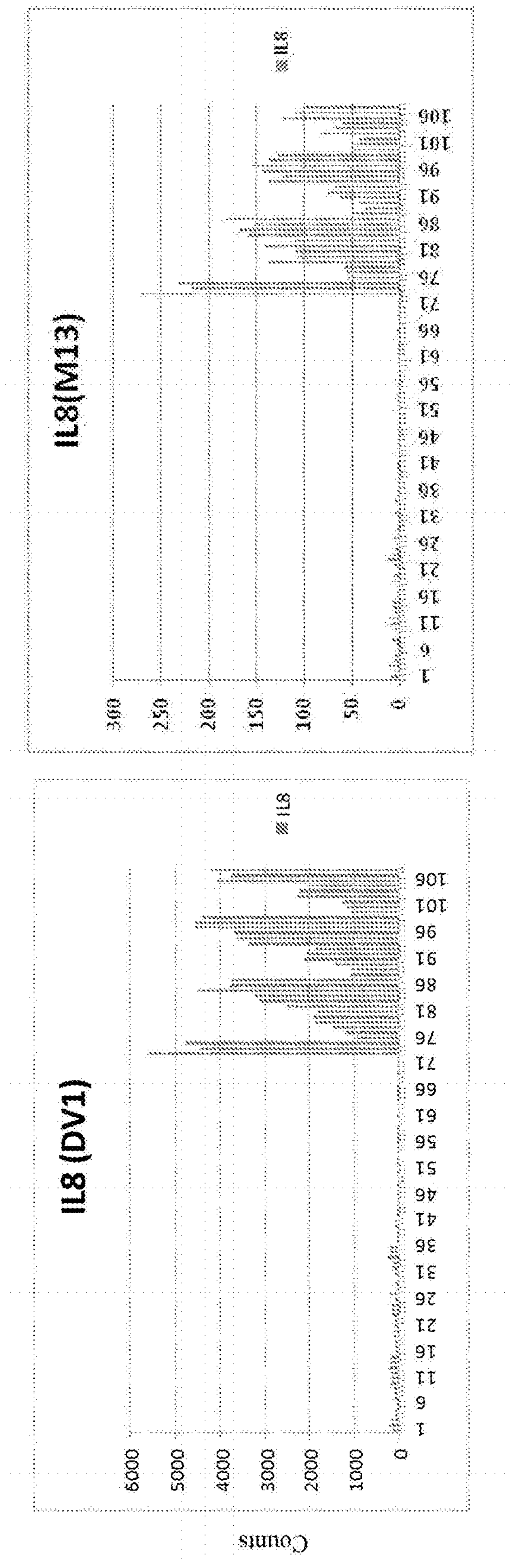
FIG. 5 shows the detection of IL-8 in the same sample using both the DV1 and M13 nanoreporter systems. The data was collected from experiments performed according to Example 4.

Results are shown for a representative three of the 40 genes probed, comparing the DV1 system to the M13 system. FIG. 5 shows the results for IL-8 (results for GAPDH, and TSC22D3 are not shown). The overall profile of the expression of each gene is the same for both systems (i.e., greater or lesser relative expression between samples), but the number of counts for each assay is >100-fold higher using DV1 (note the difference in scale for the M13 and DV1 graphs).

Figure 6:
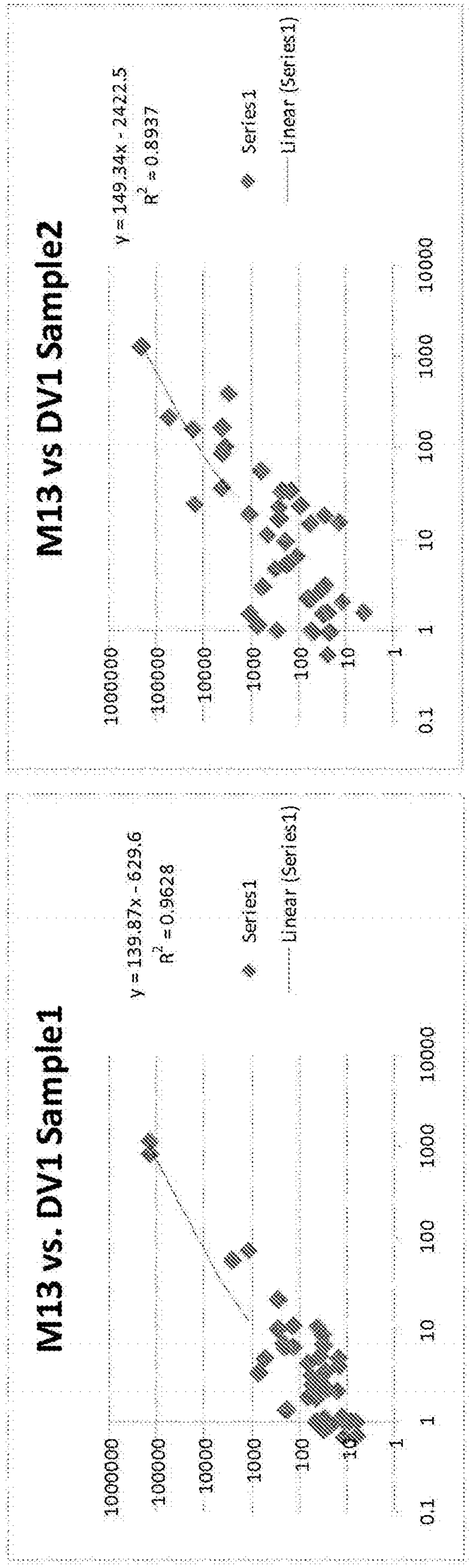
FIG. 6 shows a comparison of the DV1 and M13 systems in measuring the expression of 40 genes in two samples. The data was collected from two representative experiments performed according to Example 4.

Results of a comparison of the expression of all 40 genes between the systems are also shown in two representative samples (see FIG. 6). In FIG. 6, the $R^2$ value shows an approximately 90% correlation between the relative expression of all the genes in the two systems, while the slope of the line indicates a greater than 100-fold increase in the actual number of counts using the DV1 reporters as compared to the M13 reporters.

Example 5

Comparison of DV1 and M13 Nanoreporter Systems

A 148-probe DV1 reporter library was made as described in Examples 1 to 3, and a comparable M13 library was also made, as described in U.S. application Ser. No. 12/100,990, herein incorporated by reference. The DV1 and M13 libraries contained identical probe (i.e., target-specific nucleotide) sequences and were used to assay the same samples—26 mouse RNA samples. Standard hybridization, purification and imaging protocols were followed, as described in Example 4.

Figure 7:
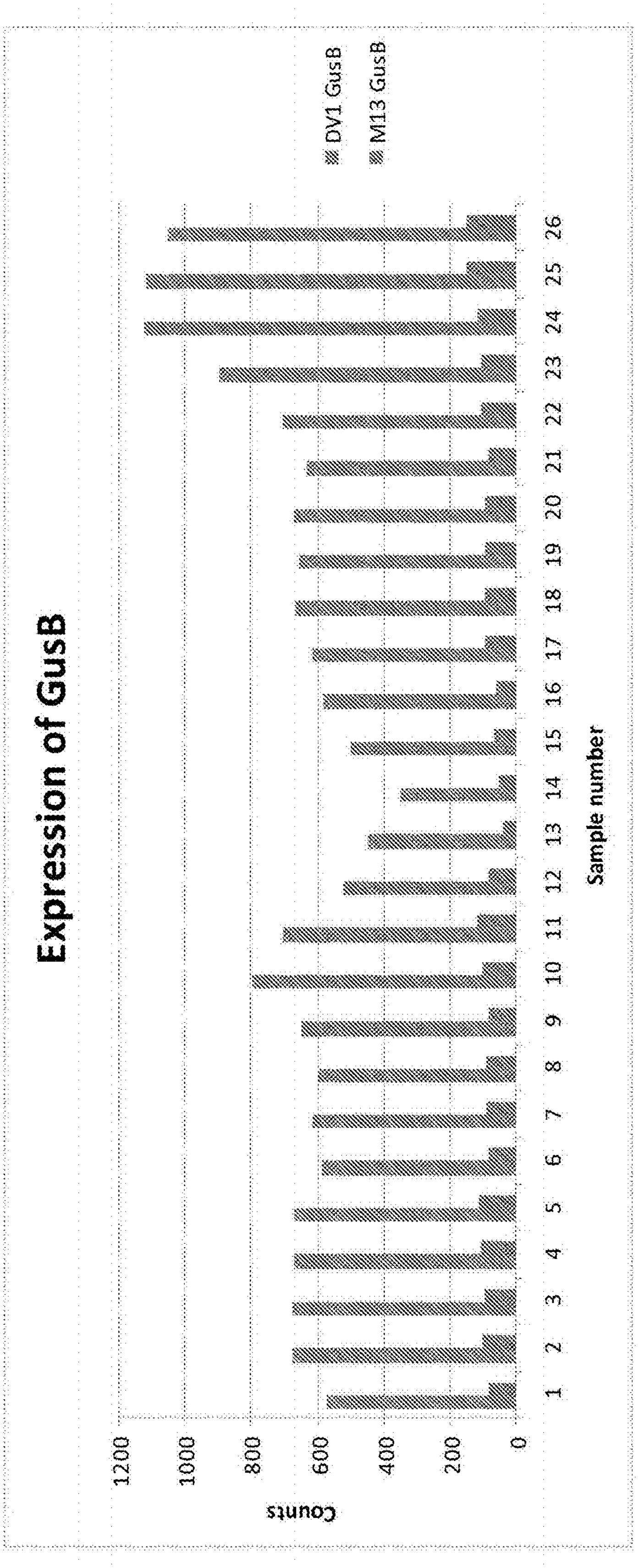
FIG. 7 shows the detection of GusB expression. In this experiment, M13 and DV1 libraries containing 148 identical probes were used to measure gene expression levels in 26 mouse RNA samples. An average 6-fold increase was seen for the absolute number of counts measured by the DV1 reporters compared to the M13 reporters. The data was collected from representative experiments performed according to Example 5.
Figure 8:
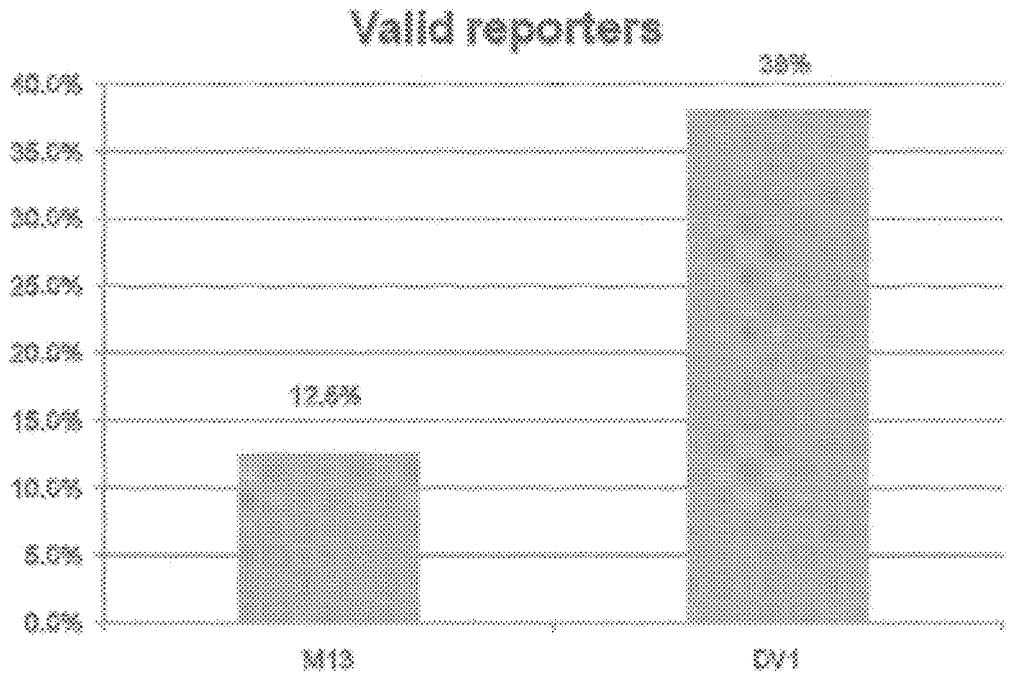
FIG. 8 shows a graph of "valid reporters," which refers to strings of spots that can be interpreted by the image analysis software as a "countable" reporter. The results are described as a percentage of the total number of binding events in a field-of-view. A significantly higher percentage of DV1 reporters are countable, in this experiment leading to a 3-fold gain in data (from 12.5% to 38%).

The results for the detection of GusB expression are shown in FIG. 7, respectively. Results for the detection of Mod 1, Acot4, and Atg7 expression are not shown. The measurement of relative expression levels of a given gene across the various samples was comparable between the two reporter types. However, an average 6-fold increase was seen for the absolute number of counts measured by the DV1 reporters compared to the M13 reporters. FIG. 8 provides a graph showing the "valid reporters," which refers to strings of spots that can be interpreted by the image analysis software as a "countable" reporter, described as a percentage of the total number of binding events in a field-of-view. A significantly higher percentage of DV1 reporters are countable, in this experiment leading to a 3-fold gain in data (from 12.5% to 38%).

A correlation of the expression of each gene in one sample as measured by M13 and DV1 was determined. The results show a 77% correlation between the two systems and an average 6-fold increase with DV1 (data not shown).

Example 6

Optimization of Dye Incorporation into Complementary RNA Polynucleotides

To determine the optimum fluorescent dye concentration in a given nanoreporter molecule, fluorescent dyes were incorporated into the complementary RNA polynucleotide sequences in various amounts. Nanoreporter molecules having various amounts of dye incorporation were then tested for signal intensity in a standard nanoreporter detection assay.

Specifically, to determine the optimum degree of nucleotide spacing between each incorporated dye molecule, fluorescent dye molecules were incorporated into complementary RNA polynucleotides at every into every 8, 10, 12, 16, or 24 nucleotide bases. This was accomplished by generating novel sequences which contained a regular pattern of T's spaced every 8, 10, 12, 14, 16 and 24 bases, as shown in FIG. 9 to FIG. 12. These sequences were approximately 1100 bases long and were assembled into a single 6600 base reporter backbone plasmid, which was converted into a single-stranded backbone. Each template was transcribed to produce the reverse complementary RNA, and aliquots of each RNA were coupled separately to four colors: blue (Alexa 488), green (Cy3(Amersham)), yellow (Alexa 594), and red (Alexa 647). A series of labeled reporters using the various colors were generated by annealing labeled RNA segments to the backbone. These reporters were imaged as described herein and the brightness of the spot resulting from the dye-coupling at each spacing in each color was determined (data not shown). Spot intensity measurements are in arbitrary units.

These experiments show that the brightness of the spots can be manipulated by designing the underlying sequence to contain greater or fewer regularly repeated bases. Here, a spacing of 8 nucleotides gives the brightest spots. Spacings of fewer than 8 were not tested due to predictions of stearic interference of neighboring dye molecules at closer spacings; however, it is likely that some spots could be made even brighter by closer spacings. The closest possible spacing will vary from dye to dye, but 8 bases provide a spacing that should accommodate all of the commercially suitable dyes. The bases do not need to be regularly spaced.

Example 7

Considerations Regarding Nanoreporter Hybridization Kinetics

Background

Solution hybridizations with a large excess of probe over target follow pseudo-first order kinetics. In this regime the speed of the reaction depends only on the probe concentration and not on the target concentration. For a two-probe, one-target strategy to provide accurate information on the concentration of a target in solution, the probes should both be present in excess of the target. The possible concentration range is preferably therefore bounded on the lower end by the concentration of the target. However, the useful concentration range for the nanoreporter technology described herein is practically bounded on the lower end by the amount of time needed to perform the hybridization.

Hybridization Kinetics

In preferred embodiments, target detection and quantification assays are performed in which the target (T) must hybridize to both a reporter probe (R) and a capture probe (G) to be detected (for example by affinity selection and detection of complexes comprising only (R) and (G), which in turn only form complexes in the presence of (T)). Assuming that these reactions are irreversible, there are four possible elementary reactions that occur.

$$R + T \xrightarrow{k_1} RT$$

$$T + G \xrightarrow{k_2} TG$$

$$RT + G \xrightarrow{k_3} RTG$$

$$R + TG \xrightarrow{k_4} RTG.$$

Because RT and TG are intermediate complexes of two out of the three species, these four reactions can be simplified to R+T+G→RTG.

However, to quantitatively calculate the rate of production of RTG (the reporter-target-capture probe complex), all four reactions must be considered. The differential equations describing the system are:

$$\frac{dC_G}{dt} = -k_2 C_G C_T - k_3 C_G C_{RT} \qquad \frac{dC_G}{dt} = -k_1 C_R C_T - k_4 C_R C_{TG}$$

$$\frac{dC_T}{dt} = -k_2 C_G C_T - k_3 C_R C_T \qquad \frac{dC_{RT}}{dt} = k_1 C_R C_T - k_3 C_G C_{RT}$$

-continued $$\frac{dC_{TG}}{dt} = k_2 C_G C_T - k_4 C_R C_{TG}$$

$$\frac{dC_{RTG}}{dt} = k_4 C_R C_{TG} + k_3 C_G C_{RT}$$

where $C_R$, $C_T$, $C_G$, $C_{RT}$, $C_{TG}$, and $C_{RTG}$ are the concentrations of the various species, and 1(1-1(4 are the kinetic constants for the four elementary reactions. Values for these kinetic constants when the probes and targets are complementary single-stranded molecules (i.e., when there is no purification tag on the capture probe and no reporter) can be calculated from data available in the literature (Wetmur, *J. Annu. Rev. Biophys. Bioeng.* 1976.5:337-361).

$$k = k_N \frac{\sqrt{L}}{N} \frac{\alpha_{salt}}{\alpha_{ref}}$$

In the above equation, $k_N$ is the nucleation rate constant, L is the nucleic acid length (in base pairs), N is the nucleic acid complexity (equal to L for non-repetitive sequences) and $a_{salt}$ and $a_{ref}$ are corrections for salt concentration (Britten et al., 1974, *Methods in Enzymology* 29E:363-406). In the nanoreporter systems described herein, the kinetic constants will depend on the sizes of the attached capture probe tags and reporter probe. Without being bound by any theory, it is the inventors' belief that the kinetic constants will have the same dependence on length that an elementary reaction has on the diffusion constants of the reactants.

$$k = k_N \frac{\sqrt{L}}{N} \frac{\alpha_{salt}}{\alpha_{ref}} \frac{D_1 + D_2}{2D_{50}}$$

In the above equation D1 and D2 are the diffusion constants of the two reacting species (see the reactions above) and $D_{50}$ is the diffusion constant of a 50-mer single-stranded DNA molecule. Assuming a 100-base single-stranded target, 100-base single-stranded capture probe, and 7200-base double stranded reporter, the relevant kinetic constants are $k_1=2.64\times10^5$ L/mol/s $k_2=6.55\times10^5$ L/mol/s $k_3=3.99\times10^5$ L/mol/s $k_4=1.91\times10^5$ L/mol/s Numerically solving the system of differential equations with these kinetic constants (assuming at least a 10-fold excess of probes over target) yields the prediction that 5 pM reporter and 5 pM capture probe will drive hybridization to 10% of completion in an overnight reaction (16-18 hours). At concentrations lower than 5 pM, the amount of completely hybridized molecules is likely impractical to measure. Thus, in a preferred embodiment, the lower concentration of a nanoreporter component (capture probe and/or reporter probe) is 5 pM.

Entanglement of Reporters

As probe concentrations increase, theory predicts that hybridization kinetics speed up without bound—the only limit being the solubility of the probes. However, the reporter probe can be very large compared to the target-specific sequence in the nanoreporter systems of the invention. Without being bound by any theory, the inventors believe that by its attachment to the reporter probe the kinetics of the target-specific sequence are altered from classical solution hybridization kinetics. Because the reporter probe is a large, polymeric molecule, it can have long-lived interactions (entanglements) with other nanoreporters when they come into contact. At low concentration the probability of two polymers becoming entangled is small, but as the concentration and/or size of a polymer in solution increases, these interactions become more and more common. In the extreme case of very long molecules at very high concentration the polymers form a permanent network, or gel, in solution. For solution hybridization to occur, a probe (e.g., a nanoreporter probe)/target pair must diffuse through solution until they contact one another and a hybridization nucleus forms. Classically, hybridization reactions are not diffusion limited because the translational diffusion of the molecules is faster than the nucleation of the hybridization (i.e., the probe and target diffuse together and interact many times before a nucleation occurs). In dilute solution its large size will slow the translational diffusion of the reporter probe, but may not significantly affect the kinetics. At some intermediate concentration, the reporter probes take up almost all of the space in the solution, effectively forming a permanently entangled gel, and can no longer diffuse in solution. However, the capture probe and the targets are smaller molecules that are believed to still diffuse through the entangled reporter probes, allowing hybridization to take place (although possibly at a slower rate). The inventors also believe that at some higher concentration the reporter probe in solution will also hinder the movement of the capture probe and the targets to the point that the reaction becomes diffusion limited. This concentration (which is not quantitatively known and depends upon the reporter probe structure, the capture probe structure, and the target size) is the upper limit of the useful concentration range in the nanoreporter system, and can be empirically determined by one of skill in the art guided by the principles described herein.

Length Dependence of Kinetics

Since the limiting upper concentration for hybridization depends upon both the reporter structure and capture probe structure (of which there are many possible variations), a theoretical framework to predict the permutations of useful concentration ranges is useful in the practice of the invention. Classical theory predicts that hybridization kinetics depend only on the size of the smaller probe. Theory would therefore predict that the size of the reporter will not play a role in the hybridization kinetics as long as both the target molecule and the capture probe are significantly smaller. Theory then predicts that the rate of hybridization (for a constant target length) depends on $1/L^{1/2}$, where L is the length of the capture probe, due to steric inhibition of hybridization. Consequently, the kinetics of hybridization will be faster with smaller capture probes. As the capture probe length increases, the hybridization rate should decrease as $1/L^{1/2}$. If a constant capture probe length is assumed, then the range of reporter lengths and concentrations that will result in a measurable mount of hybridization events can be defined. Once a reporter size has been defined, then the approximate range of capture probe sizes can be determined. This is an iterative process, but may give good starting points from which to gather data to generate detailed empirical guidelines, given that the theories that the inventors' rationale is based upon were generated from hybridization data in systems that do not employ a reporter probe.

Entanglement Threshold

A reporter probe is essentially a polymer in free solution, which behaves as a random coil. The volume occupied by a single reporter, $V_p$, can be calculated from polymer physics theories according to the Freely-Jointed Chain model (FJC, for a flexible polymer, such as single-stranded DNA or RNA) or the Worm-Like Chain model (WLC, for a stiff polymer such as double-stranded DNA or a reporter). For either model $$V_p = \frac{4}{3}\pi R_g^3$$

where $R_g$ is the radius of gyration. For the FJC $$R_g = b\left(\frac{N}{6}\right)^{0.6}$$

where b is the segment length and N is the number of segments in the chain. For the WLC $$R_g = \sqrt{\frac{1}{6}Nb^2 - \frac{b^2}{4} + \frac{b^2}{4N}\left(1 + \frac{1}{2N}(e^{-2N} - 1)\right)}$$

The entanglement threshold concentration is defined as concentration is defined as the concentration where the entire volume of the solution is occupied by the reporters.

$$C^* = \frac{3}{4\pi R_g^3 N_A}$$

where $N_A$ is Avogadro's number. Above this concentration it is assumed that the translational diffusion of the reporters is severely restricted. The entanglement threshold concentration varies with the reporter structure. As the reporter length increases, the entanglement threshold decreases (as $1/L^{1.5}$). From the equations above, the theoretical entanglement threshold for reporter probes with different spot sizes and different lengths can be calculated. The result of such calculations shows that for a 7200 by RNA/DNA hybrid reporter probe with 8 label attachment regions of about 900 by each, the entanglement threshold is about 70 nM.

If both the target and the capture probe are much smaller than the reporters, then they will most likely be free to diffuse through the solution even at these high concentrations of reporters. Initial data indicates that hybridization kinetics do not slow appreciably up to a concentration of 80 nM with a 7200-bp reporter probe, a 100-base target, and a 100-base capture probe.

Effect of Entanglement Threshold on Multiplexing

Assuming that the maximum concentration for reporters in a hybridization reaction is C*, then the concentration of each reporter (specific to a particular target) is equal to C*/M, where M is the multiplex of the reaction (number of different targets being addressed simultaneously). Conversely, the possible multiplex level for a particular reporter structure can be calculated from the lower limit of probe concentration ($C_p$ from kinetics ~10 nM) and the entanglement threshold $$M = \frac{C^*}{C_p}$$

If the number of nanoreporter codes available does not depend on reporter probe size, then the multiplexing of the nanoreporter depends primarily on the reporter probe size and concentration (since it is much larger than the capture probe). Because the capture probe makes an insignificant contribution to entanglement during hybridization, it is the inventors' belief that the concentration of the capture probe can be increased far above the concentration of the reporter probe. In Table 4 below, the maximum total capture probe concentration ([G]) is set to 1000 nM for all reporter concentrations. This difference in concentration of capture probe and reporter probe is an adjustable parameter. Preliminary experiments show that in a multiplex hybridization reaction with a 7200 by reporter and 100b capture, 40 pM of each reporter probe and 200 pM of each capture probe results in near complete hybridization in an overnight reaction.

Optimal Size and Concentration Ranges

Below in Table 4 is a summary of the optimal useful size and concentration ranges of the capture probe and reporter probe at different multiplexing as approximated by the above theories. It is the inventors' belief that capture probes up to about 200 bases will be practical for most applications

TABLE 4

Optimal size and concentration ranges of reporter probe, capture probe and target, as well as multiplicity of probes, in the nanoreporter systems of the invention.

| Reporter Length (bp) | Capture Length (b) | Minimum [R] (pM) | Minimum [G] (pM) | Maximum [R] (nM) | Maximum [G] (nM) | Max Multiplex |
|---|---|---|---|---|---|---|
| 2000 | 100 | 5 | 5 | 603 | 1000 | 114417 |
| 2000 | 50 | 4 | 4 | 603 | 1000 | 161811 |
| 2000 | 200 | 7 | 7 | 603 | 1000 | 80905 |
| 3000 | 100 | 6 | 6 | 292 | 1000 | 45182 |
| 3000 | 50 | 5 | 5 | 292 | 1000 | 63897 |
| 3000 | 200 | 9 | 9 | 292 | 1000 | 31948 |
| 4000 | 100 | 7 | 7 | 178 | 1000 | 23912 |
| 4000 | 50 | 5 | 5 | 178 | 1000 | 33817 |
| 4000 | 200 | 11 | 11 | 178 | 1000 | 16908 |
| 5000 | 100 | 8 | 8 | 123 | 1000 | 14746 |
| 5000 | 50 | 6 | 6 | 123 | 1000 | 20854 |
| 5000 | 200 | 12 | 12 | 123 | 1000 | 10427 |
| 6000 | 100 | 9 | 9 | 91 | 1000 | 9988 |
| 6000 | 50 | 6 | 6 | 91 | 1000 | 14125 |
| 6000 | 200 | 13 | 13 | 91 | 1000 | 7062 |
| 7200 | 100 | 10 | 10 | 68 | 1000 | 6792 |
| 7200 | 50 | 7 | 10 | 68 | 1000 | 6792 |

TABLE 4-continued

Optimal size and concentration ranges of reporter probe, capture probe and target, as well as multiplicity of probes, in the nanoreporter systems of the invention.

| Reporter Length (bp) | Capture Length (b) | Minimum [R] (pM) | Minimum [G] (pM) | Maximum [R] (nM) | Maximum [G] (nM) | Max Multiplex |
|---|---|---|---|---|---|---|
| 7200 | 200 | 14 | 10 | 68 | 1000 | 6792 |
| 8000 | 100 | 11 | 11 | 57 | 1000 | 5444 |
| 8000 | 50 | 7 | 7 | 57 | 1000 | 7699 |
| 8000 | 200 | 15 | 15 | 57 | 1000 | 3850 |
| 10000 | 100 | 12 | 12 | 40 | 1000 | 3419 |
| 10000 | 50 | 8 | 8 | 40 | 1000 | 4835 |
| 10000 | 200 | 17 | 17 | 40 | 1000 | 2417 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A probe pair comprising:

(a) a first probe comprising (i) a first region that selectively binds to a first sequence of a target nucleic acid; and (ii) a second region comprising a plurality of designed label attachment regions covalently attached together in a synthetic linear combination, wherein each label attachment region is hybridized to a complementary polynucleotide sequence having attached thereto one or more detectable molecules, wherein the second region comprises less than 85% homology to any sequence described in the REF SEQ public database;

(b) a second probe comprising a region that selectively binds to a second sequence of the target nucleic acid; wherein the second probe further comprises an affinity tag; and wherein the first sequence and the second sequence of the target nucleic acid are different;

wherein each label attachment region is different from the other label attachment regions in the plurality of designed label attachment region.

2. The probe pair of claim 1, wherein the target nucleic acid is DNA or RNA.

3. The probe pair of claim 1, wherein the first probe further comprises a constant region wherein the constant region comprises a plurality of repeat nucleotide sequences.

4. The probe pair of claim 1, wherein at least one of the plurality of designed label attachment regions comprises a regularly repeated pattern of adenine bases.

5. The probe pair of claim 4, wherein the adenine bases are spaced about an average of every 8 to 16 nucleotide bases.

6. The probe pair of claim 1, wherein the complementary polynucleotide sequence comprises an RNA polynucleotide sequence.

7. The probe pair of claim 6, wherein the RNA polynucleotide sequence comprises at least one amino-allyl modified uracil base.

8. The probe pair of claim 7, wherein a detectable molecule is attached to the amino-allyl modified uracil base.

9. The probe pair of claim 1, wherein the one or more detectable molecules are fluorescent dyes.

10. The probe pair of claim 1, wherein each label attachment region comprises about 800to 1300 nucleotide bases.

11. The probe pair of claim 1, wherein each label attachment region has a G/C content of about 50%.

12. The probe pair of claim 1, wherein each label attachment region has a thymine content of about 35-45%.

13. The probe pair of claim 1, wherein the second region of the first probe comprises less than about 1% of inverted repeats or direct repeats.

14. The probe pair of claim 13, wherein the inverted repeats or direct repeats are 9nucleotides or greater.

15. The probe pair of claim 1, wherein each label attachment region lacks a direct or inverted repeat that is greater than 12 nucleotides in length.

16. The probe pair of claim 15, wherein each label attachment region lacks a direct or inverted repeat that is greater than about 7 nucleotides in length.

17. The probe pair of claim 1, wherein the complementary polynucleotide sequence has a G/C ratio of at least 1/1.

18. The probe pair of claim 17, wherein the complementary polynucleotide sequence has a G/C ratio of about 3/2.

19. The probe pair of claim 1, wherein the affinity tag is a digoxigenin tag.

20. The probe pair of claim 1, wherein the affinity tag is a biotin tag.

21. The probe pair of claim 1, wherein the first probe further comprises an affinity tag.

22. The probe pair of claim 21, wherein the affinity tag of the first probe is a biotin tag.

23. The probe pair of claim 21, wherein the affinity tag of the first probe is a digoxigenin tag.

24. The probe pair of claim of claim 1, wherein at least one complementary polynucleotide sequence has a melting temperature (Tm) about 80° C. or higher when hybridized to its label attachment region.

25. A population of probe pairs, wherein each probe pair in the population comprises:

(a) a first probe comprising (i) a first region that selectively binds to a first sequence of a target nucleic acid; and (ii) a second region comprising a plurality of designed label attachment regions covalently attached together in a synthetic linear combination, wherein each label attachment region is hybridized to a complementary polynucleotide sequence having attached thereto one or more detectable molecules, wherein the second region comprises less than 85% homology to any sequence described in the REF SEQ public database;

(b) a second probe comprising a region that selectively binds to a second sequence of the target nucleic acid;

wherein the first sequence and the second sequence of the target nucleic acid are different; and wherein the first probe or the second probe of each probe pair in the population further comprises an affinity tag; and wherein each label attachment region is different from the other label attachment regions in the plurality of designed label attachment region.

26. The population of probe pairs of claim 25, wherein the first probe further comprises an affinity tag.

* * * * *

SEQUENCE LISTING

<160> NUMBER OF SEQ ID NOS: 33

<210> SEQ ID NO 1
<211> LENGTH: 1140
<212> TYPE: DNA
<213> ORGANISM: Artificial Sequence
<220> FEATURE:
<223> OTHER INFORMATION: Synthetic polynucleotide

<400> SEQUENCE: 1
gaattcaaag ggctgggtga agcggtgaaa cggtcgagcg ctgaaggaat gagaaagtga 60
ggcggtagac aaaagtaagc cagtggcaca gtgaggaaga tgagcgagct gaggacaatg 120
acggagtcgg aggaatcaga gcggtgagac aagtggagga tatcaaagat aagagcatag 180
ggaaatgcaa caatggaaac gtcccaaggt ggaagcgtgg gagaatgaag aggtaagcaa 240
atagaagacg tagggaacat gaaaccatgc agaagataag aaaatgccag aatacgacgg 300
tgagagaaat caaccagtac aagcgctgaa cagctaccga ggtagcgaga tgaacaagat 360
gcgaacctca ggaactcaag aagtagcgaa atcgaccggg tcgggaaagt cgagaaataa 420
gaacgtacca gggatacaga actagggacg taggagggtg ggacgatacg gcgctgaaac 480
gggtgggagg gtaacagggt ggaaaagtaa gagactaagg aactgaaaca gctaacaggc 540
taagggaaca tggagaaata aagacactgg agcgcagctg gaagatagag aaaatgagag 600
cgtgaaacca tgaaagggat caagaggtga cggagcatag aaagctgaaa caaataggga 660
agctgaagac cataagcggg ctgccaaaga taagagagtg acaagatacg cgccgtggag 720
aagtgcagga cataaaacaa tggccgcatc aggccgggtg agggcaatac aagagctaga 780
agagtaccgc gataggaagg tggcaccagt aaggaaataa gcccatgagg acatacacga 840
gtcgaaaaat aagcgagtca aacgctaggc caactggcgg catgggacgg tgcgcgggtc 900
gacagaggtg tacaagtgac aggatgaaag cataagaagg tgacgcaact agggccatac 960
aaagagtgga ccaatccaaa cctgcgaaga taggaggata acaccggtag ggcaactaca 1020
aggatcaaag gatgaaagaa taaaacacta agggcgtcca acagtaccga agtcagggcg 1080
tcacaggctg aacagaactc aaccgaagtc tagaaggatc cactcgagtt tagatctttt 1140

<210> SEQ ID NO 2
<211> LENGTH: 1141
<212> TYPE: DNA
<213> ORGANISM: Artificial Sequence
<220> FEATURE:
<223> OTHER INFORMATION: Synthetic polynucleotide

<400> SEQUENCE: 2
gaattcaaag ggctgaacgc aggtacgaga gtaccgggaa tagcggagtg aagccctaaa 60
gaaataacag gaatagcaca agtaggaaca taaacagatg cacaccaata aagagatacg 120
gaaataaaga catagagaca tccgcaaata aagggatgaa acaataaccg ggtcgcgaag 180
ctaacaccca tcgccagctc gggcaaactg atatcctcga aggactagca agatggaaac 240
atggacaagt aaaagggtga agaagtacca caaactcaac agctaagaca agtcgggaag 300
taaaaaaatc caagggtaac agaatggcga agtgagcgaa agtagagcaa tgacggcatg 360
gagaaatggg aaaaaatcac gagatagacg agtgggcagg taggcgggtg accggaatac 420
gacaatgaga gactgccgca gtgcgaaagt ggcgggataa aaaagctgaa gggagtcaaa 480
ccatcagcgg gatacagaag tagaacaatg cacagatgcg caggtaagcg ggtgcaagac 540
tagaaaagct cggcaaatcg ccgaatagac aaatcagctg gtgagcgggt acgaagactg 600
gcggccataa cgccatgagg gcatagcaaa agtacccaaa taaggcagtc agagagtgac 660
gggctacagc ggctaggccg actacagcag tgcgggaagt gaaaaaagct cgaaggatgc 720
aaccatgagc caataaaggc gtcgagagct gccaagatgc gaaagtgagg acatagacga 780
atagaaaaat gagacgatag cgaggtgaca ccataccagg gtccggcagg tagccagata 840
gggaaataga acgatcaaag gatagcgaaa cgtcagaaac tcgggagcta aaaggataac 900
ggaatcagat gtacaacgca gatcagaacc tgggagcaag tggagccaat caacaagata 960
agaaaaatga aggcatggaa acggtccggg cagtggaacg atccaagagt aggaaaatca 1020
gaagcgtacg aaactacaag cgtcagggag tagaaaagta acacaatgaa gaaactaagc 1080
acgtgaaaga gtagaggaac taggaaacat ctagaaggat ccactcgagt ttagatcttt 1140
t 1141

<210> SEQ ID NO 3
<211> LENGTH: 1142
<212> TYPE: DNA
<213> ORGANISM: Artificial Sequence
<220> FEATURE:
<223> OTHER INFORMATION: Synthetic polynucleotide

<400> SEQUENCE: 3
gaattcaaag ggctgacaac cactgaaggc ataaacaagt accaaagtaa cagcatggag 60
agctgagggc gtaacaaagg tcgaaaactc aaacactaca aaaatgggac aaatagcgcc 120
catcggaagc ctgagcggat agcggactac ggcagtaaag agatagcgga gctgaaagcc 180
tcaggacgtg aacaaatggg aaggataacc gggtaggagg gtgaaacaga tgagacggta 240
agaaaagtaa gagaaggtgc gatatcgcgg gcgtcacgca acgtgcaaaa atgacggaat 300
aaaagaatcg aggaggtcaa ggcgataagc gcgtgagagg atagaaagat cgagccatag 360
cgggccatca gcggcgtgcg aggagtcgca ccactcaaga gctaacccga tcagcgagta 420
cagcgggtag aagcgtcgcg ggatagagga agtccaaaga tcccgaactg ccagcgtagg 480
aacactgacc acatagcacc atcaaaagct gaacgagatg agacactacg caggatgaga 540

-continued

```
acgtcgcaag catgaaccgg gtgcagagct aggacagctg cgccgatcag gccacgtagg    600

aagatccaag cctggcacag agtcaagacg ctagaaaaat gaagaagtca gcaaagtagg    660

gagggtggga gcatgaacga gtgaggacat aggacgatcc caaagtgacg gaatgaccag    720

gtgagaaagt agggcaaatc aagcagtcaa agcgtgaaga aaactagaag gcgtaaaaga    780

gtggagaagc tccgacagat acaaaagtag aggcctgaga gggtcgggca aaatcccaga    840

ctcggagaat cgcgacaatg caaacgtggc gcggtgggcg aggtgccgaa atcacgcgaa    900

tggacggata tgtacactga aaaagctcac aaaataagcg gatcgggaca tcggaacctg    960

agacgaatac agacgataaa gcaataaccg actagacgag tgccagggta ggaacgtacc   1020

aaaagtccag aagtccacgg gtggacagac tagagaacag tacagaaaat gccaccctaa   1080

acgggtaagg gaatgcggga gtggacaaac tctagaagga tccactcgag tttagatctt   1140

tt                                                                  1142
```

<210> SEQ ID NO 4
<211> LENGTH: 1140
<212> TYPE: DNA
<213> ORGANISM: Artificial Sequence
<220> FEATURE:
<223> OTHER INFORMATION: Synthetic polynucleotide

<400> SEQUENCE: 4

```
gaattcaaag ggctgaaaga atagacgggt aaacaagata gaggcatggg aggcctgcga     60

aagtggacaa atgacgggat gccagggatg cacgactggc aggatggcaa cgtaagaggc    120

taccacgctc cgggaggtaa ggcgatcgaa agagtagaga agcatacccg cataggacaa    180

taaaagggta agggaagtgg gagcatccga aaatagaacc ctacaggcaa gtagacaggt    240

aaacgcatga gaagacctgg gcgcgggtcg gaacactgcg ccagtaaggc ccatgaaaaa    300

cggtgagaga tatcacagaa ctggaacaac tccggacata cagaaataca cgaatagggc    360

aatagacgag taacaacgat aacgcgagta gcgcgagata cgaagagtag caagactcgg    420

aggagtccaa gaaaataagc agatggcaaa gatagggaag aataaacgac tggagccagt    480

gaggagctaa aagggtcagc agactggacg ggtaaggaga tacaaaactc agcgaatcaa    540

aaaatacagg caagtaccag ccatccacgg gtaacagctg gccaccgtcc ggcaaataaa    600

agaatccagc agctagagcc ggtaacccaa tcccgagagt cgaagagatg gcagaatgag    660

aacaatacaa gggataagca gggtacggga atgaaacggt agaggacata cgaggataac    720

aacactaaag gactagagag aataaacagc gtgacacgac taaaaaaagg tacgggcgat    780

caaacaagtg gaagactcca aaagataacg cggtgagcga atacggaggt cgaaaaaaat    840

agacgggatg gcgggatgcc agagtagaag ccctaagaga atagaaagca taaaacacta    900

ggcaaacttg tacaatagac gggtgaaaag aatgaggcga tcaaagcata gcaaaatcag    960

gaactaagca gggtcgccgg catggaaaca tagccaaata gggaggacta gcagggtgga   1020

aggatgacga actagaagcg atcaacggat aaggaggtgc acagatagca cgaataacgc   1080

gggtaagaaa gtacaagaat gagcaacgtc tagaaggatc cactcgagtt tagatctttt   1140
```

<210> SEQ ID NO 5
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 5

```
tctagagaag gatacaggaa tcaagacatg cagggaacta aagacatacc ggaataagag     60
aggctaaagg gataaggaga gtacgaggag taaagacaga tcgacgggaa taacaagagt    120
caagacgtga ccgacctgag cgcatcgaga ccgcgggaga ctcggcgggt gaacaaatgg    180
aaggataaga acgggtagaa gaactacgcg aatgaaggga tgtacaaggt agggcagata    240
agagggtggc gagatgaaaa ggctcggaaa actcaaccaa ctggagaact aggccggtcg    300
aaggaataga aacgtaagcg agataagagg atggcgcaga ctgggacaat cgggaggtcg    360
agagatcacg ggaatagaca cgtccaagaa atgaacaagg taaggacatg cgggaataag    420
aaactcaaac cctaggccag tcacagaagt aacccagtac gcaagtcacc gagtcggaac    480
gatgacaaag taaaaaaggt gaaagaatga gagcactaaa aaagtaaaag agatcaggcg    540
cgtgggcgag atgcagaggt aacgaaataa aaagatcgca gaatccaaag actacggagg    600
atcaggcaaa taagaagata aaaaagatcc gaagataacg aggtaggcca atgagagaat    660
accgagcgta gagccatacg agagtaaaga gagtagggca gtaaaaagat ccagcggtag    720
gagcatcggc gcctcaagaa gatccagaga tggaacgcta ggagaataaa gcggtgaaag    780
cgtacaaacg tagggaagtc gggagagtag agagatacag agagtaagag ccatagacac    840
ctgagacgat cggcaactgg gcaacatcca gagatgggca cctaggcaca tcaccgggtg    900
caaaggatca cagagtagaa cgctcaaaga agtcaccaag tgcacgggta agggacatgc    960
gaaggtgaga gcgggtggaa aactcgacag ctcaacacat gagggaatgc cagagatgga   1020
gcaaataaga gacatgccgg gcgatgagga actacaacag tagcccaatg caaggctaag   1080
gaagtacaaa agtcgggaaa ggatcc                                        1106
```

```
<210> SEQ ID NO 6
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 6

tctagagaat gaaacagtgg aaaggtcgga aactgaggcg gagtagaaac aagtcgcgag     60
atacgagaga tgaaagagcg tcaaagaatg gaggactcag aagatagaaa catcgggaca    120
ggtgagaaca ctgggaaaga atcgaaaaaa ctaccaaaac tacaaaaact gcaaaaatga    180
aaggagtgga ccactggaca gccgcggaag ctcaagaact gtgtacaggt gcagcggtca    240
gaaacatcaa aaggtaacag catcgcggga tcggaaaatc cgggagtcaa aaagtgcaga    300
aatgacacgg gtacgaaacc tcagaaacat aaacagctac gggcatgaga gcataaagag    360
ataaaaaaat gcagagcgat accacacgta aggagatcgc aaggtgccac gatcagaaaa    420
tagagacatc gacgggtggc gaactgagca acatccggga ataagaacct caagggcgtg    480
caaccggtac acgaatgaga ggatgcggga gtcagcggag tgggaaggtg aggaaagtag    540
aaaaaataca gccaggtaca aaagtaaagc gggtcaaccg gtagccaagg tgcgaaagta    600
ggcccgtgag aaaatccggc aatagaacag taaaaaggtg agacgcataa cacgggtgca    660
aagctaagag agatccacca gtaggaagat gggaaagcat aacaaagata gaagaataag    720
gcagtaggag aatgaaaaca atacagaaaa gtagggcaga taaagcacta acgagctgac    780
aggctggcag gatgaagaca tgacacggat caaggcatgg acgagtgcac aggtcaagcg    840
ctccggcgat gagcgaatag cccgcgtaac acagtccgac aaggtgggag catagcccga    900
```

-continued

```
tcacgagggt gcaggcgtga gaaaagatcc agggctaaaa cactagaaac atggcacagt    960

acagggactg aggagctgac aagatgcaca cggtcaaagg ataagaaacg tcacgaggat   1020

accaccatca cgaaataagc gggtcggaaa catgccagac tgggcaagtc accaggatga   1080

agaaatgaag aagtagcaag aggatcc                                       1107
```

<210> SEQ ID NO 7
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 7

```
tctagagaaa aacataagca gcatggagcg ctacgggagg atggcacggt cgcgggaatc     60

gaacgctgaa gcaatcaaag ggtagggagg tcgggcaata cagcgatcgg aggatgagac    120

gggtcacaag aaatgggacc atccgcaaat caagagataa ggaaatacaa ggaataagaa    180

ggatgaaaac gtgcggagat gaagacgatg acgacaataa tgtacaatga gcagatacac    240

acggtgaacc ccgcggaacg ctaacaaaat accgaaataa aaaaatagcg agatacaggg    300

ctaaagaagt gcaagggagt aaggccctgg cagggtaaca agctcgcgga cgtcaccgcc    360

gtgcgggcaa tacgaccgct aaagaagcta gagagaatca gcagggtaaa gaagtaggac    420

cgactcgcaa gatcgagaaa taaaaaagtg gaccgggtga gcacggatga acaagtgaag    480

aaatacagag gtacaagaat cagaaacctc gggacataga aacatccaag aagatgggca    540

gaatcgaaca ggtagacgag tgagaagact aaaacaatga agaactaggc ccgcatacga    600

gactgaaagc atcaagagga taaggaactc agaaaactag agaaactaag gcgatcagga    660

ggatgagaaa atcgacgagt aagggaagtc cgggagtaca cggatgaacc gatacaagga    720

tggcgacgtc cagcaatgga aaggctcagc cgataacacg gtaggagcaa tagaagaaat    780

aaagacgtgc gcggaataag aaaggataac gagatcaaga caatggaacg agtacaaaag    840

tcaaaacgtc gaaagggtaa agcactgacg aacatagagc gataaacacc tgggaagatc    900

cggaactagc aaaatcacga caaatgcaaa gatcagccga tcgaggcata ccagggtgaa    960

aaaatcaaaa aagtaaccgg acctaaacca acgtgagaaa atgcgagcgt acagacctga   1020

cgaaatcaac aaatgaagaa gtaacagaga tccaaaactg aaaaggtaaa agcatggaca   1080

cgtaagcaag atagacaagg ggatcc                                        1106
```

<210> SEQ ID NO 8
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 8

```
tctagagagg tagcacacgg tgaaaagcta agaacctcaa acgatcgcac catgacgcga     60

atgagacaaa tgccgaaata cacacatacg aaacctcaag accctaacgg gctaaaagag    120

tcggagccat agaaaggtaa cagcgatacc gaaatggaac gggtgcagca ataaagaagc    180

taaacgaagt aggaaaatag ggaaatggaa ccagtgggac atgtacagac gaatcggaaa    240

catgacgacc tggacgggta cggcaagtaa aaaaataaaa gagtagagac atgaaaacat    300

accgcggtga gagcgtagaa gcgtgaaaca gtaagcggct aagggagtcg gaggataaac    360

ggctgacgga gactgacaac cataaagcag gtgcaaaggg atggcaacgt caaggcgtcg    420
```

```
cagaagtaag ggaatggcaa aactaagcaa agtagagcac taacaaaggt aggacgaagt    480

acgaaggtga ggaggtggaa agctggcgca catgagagaa tacaagaact agcgaaggta    540

cagcactgga cggatcaaaa cggtcgcaac gtaagacggt agggcggtag aaaagctcaa    600

cgactgagag gcatgaggac gctaaaggga gtagcaagct gagaaaatgc cggaagtgaa    660

aaactggaaa gataagcaag tccgccaagt cgagaacgta gaagagtacg ggagtacaga    720

acctgggcga agatcaggcg agtagcagag tcaaaaactg gcaagatcag gagctaacca    780

aggctcaggc aatgcaagac tgaacgggtc acaagcgtca ggacatagaa gaatgaaaga    840

gtaccagaat acacgggata gcagacgtaa ggacgatagg agcgtgagcc aatccgagga    900

tagaggaata aagcacataa gcgggtgaga ccatgagagg atcgaagaat acgggaataa    960

ggcgggtaag aacgtgacgc aagtgaggcg ataagaacaa tagcgcgaat gacggagtac   1020

ccaaatcaag ggatcgccgg gtgaaaaagt aagagaatcg ccagcgtcca aggaagtaga   1080

ggaatacaac aagtcacgga aggatcc                                       1107
```

<210> SEQ ID NO 9
<211> LENGTH: 1108
<212> TYPE: DNA
<213> ORGANISM: Artificial Sequence
<220> FEATURE:
<223> OTHER INFORMATION: Synthetic polynucleotide

<400> SEQUENCE: 9

```
ggatccgatc gggagataaa gggagtaaac gcatcaaacg atggcgagat gaacaggatg     60

acagggtccc gaacataccg ggatggagcg ctgggaacct ggaggaacta gaaacctccg    120

aagctccacg ggtgaacagg tggacaggta aaagaataca acaagtacaa ccgtgaaaaa    180

ccctcaggcg gtagggaact cgaagaaatg agcgggtaag gaaggtaaag ggatgaacgg    240

gtggaaagat gggaaggtaa agagaatggg acaccataac cgcatacgcg gaatggcaag    300

agtgcacaac taggagaagt cacaaagtgg aaaactcgca ccgtaaggac ctggacggga    360

atagacggga tcgaacggat atcgagtacg gaaagtccaa gagctgcgac actagaacac    420

atgcacgact acgccaggtg gaaagcgtaa acgccgtgca aagctcgccc ggaatcagac    480

agtgggcgga taacgaaagt aacccagggt gacgcgctgc cagactaaag gagtaaggga    540

gatacaggca ctaaaaggga taagcggatg acacggatag caaacgtaag gagatgacag    600

gcatagcaga actacgaaaa tgaacgaata gagaggctaa gagggtggag acgatgcaaa    660

gaataagaga ataaaagacg tgcaggcatc gaaaactgca agagtagggc catcggcaac    720

tcgaccgggt acaacgctaa cgaacgtaca gggctcggcg aatcgacaaa ctcgaaggat    780

cagaccacat ggaaacgtcg ggacaataac ggaataagca actacgacgg tgaaggcgtc    840

aacaagtgga cgagtaaagg cgtgaagacg tccagagctg gaaccctgcg ggcataaaga    900

gagagctcaa tgcgcagact gaaacaataa ccaggtagag gagatccacc ggtcaggcga    960

taaagaaagt cgacaggtga cgaggtgacg aggtacgcga ataaaccaat accggaatga   1020

gaaggtacag gcgtagaaaa gatgaggaga tcagagcgat gaagagatag cgaagtaaag   1080

aaaatacgaa agtccgggag aactcgag                                      1108
```

<210> SEQ ID NO 10
<211> LENGTH: 1107
<212> TYPE: DNA
<213> ORGANISM: Artificial Sequence
<220> FEATURE:

-continued

<223> OTHER INFORMATION: Synthetic polynucleotide

<400> SEQUENCE: 10
ggatccgagc tacaagacta caagagtcgc gcgccgtaaa aaaagtggcg caggatggaa 60
acgtgaggag gtagcgaagg tacagacctg gagagatcag gaactggcag aatgaggaca 120
tcagccgatg aacgcctggg caaataacgc aatagaagag taggcagggt agagcgctaa 180
cggaatccgc acgataagag cgtgggaggc taacagaatg gcccaatgac gggacgtaag 240
cagatgaaaa cagtggcgga gctggaagaa tcagagcagt ccgagggtgc agaggtaagg 300
agatgggaga aatgcaaaga atgcggaagt aaacaaataa gaggatcgga gggctaaaac 360
gggtcggcga gtgaaaaaat cgggaagtca gcgcataaag gcctgaaaaa gataagccga 420
tgaagaaact gggcggatga cgcgggtgaa agatatccgg gaatggcacg gtggcgggat 480
ggaaaagtgc gggaatcggg ccgtgaacga atagaacggg tacacgcgat aggcaagata 540
accggatcga gagcactcaa gcgataccaa gctcgcaaga gtaggagcgt accgggagtg 600
acaagataag agagtaggga gatccagaag tcacgacatc gggagctgcc gggatcagag 660
ggtcagggaa tagcgaaaaa tgcaagaata gaaacatgca gacatgaacc gggtaagcca 720
atgaaccact gacagaggtg agagcatagc gagctaggac ggtaaaagag gtccaacgcg 780
gtccagagat ccgaaaatcg aaagagtaaa aagataggaa ggtgacccac tgcgagggat 840
gacaacgtga aaaaaatggc gcgataacaa cagtacgaaa gctacgggaa ctgacagggt 900
cgagctctag caaaactgcg ggagtggaac ggtagaggag tagggcaata gaaacatgaa 960
gcaatgaaag ccgtagggaa actccaccag tcggagaata cgacaggtca cgcaaataaa 1020
gccgtcaacg ggtgaccggc tacaagcgtg caacaaaata agaacagtgg gacagagtag 1080
gccactagaa ccataaccaa actcgag 1107

<210> SEQ ID NO 11
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 11
ggatccgact acaaaaatgc acagatggcg aggtaaaaag gtagccaagc tgcgcgggtg 60
agcggatggc gaagtgcaca ggtaagagag tacacagctc aagcagtagg gcaagtaaag 120
aactcacaag ataagccgat caaggcgtcc aagcgtggcg aggtgggaga ctacaacacg 180
atagagcagg taaaaaagta aaaagataac aaaaatccgg gaagtgaagg aatcaaacaa 240
tggagaagtg aggcaactgg agaactcaga gcatacggca gatggaacgg tccgggaaat 300
caagcgagtg agagggatcg ggaaataggc agaatcaaac aagtgggaag atcaaccggt 360
gaggagacta aacgcataac cggatagagc cgctacggca ctaagaccgg tagggagctg 420
cgggagtgcg agacatggac gagtggacac atcgagaggt caaggagata gagaggactg 480
agggactccc aggataaaaa ggagtaagag agtccggcag gtcccagata tcggacgtca 540
aacgataaaa aaatgggcgg atacagacgg gtcaagaaat cgcacggctc ggacgatgac 600
ggaataggaa aatgaggcgc taaaaaacta gagaaatgag gaagtacgag cgtcgcggaa 660
tgaggaaata caaggatagg caaatgagac gatggaggcg catcgacaag tcagaaaaat 720
gccgcgatcg aggacgtcga cagagtagga cactgcggga aataaaggaa tcagaaggta 780
gagagcgtca cgcggtggaa agctcagcgc aatcacggac tagaaggaat ccggacatcg 840
agaaactacg agaagtgaaa aagtaagccg atccagacat gcccacaatg gcaccataac 900
agagctcaaa actggcgagg agtgagccac agtaagacag tcccgaaata aacacataca 960
aggctagaaa aatgcgaaga gtgcgagaag gtcgggaagg tagagagaat acaaggctga 1020
cggagtgagg aaataagaga gtggacagag tacgagagag tgcgaccaat aaacgggtag 1080
gcgaatcaac ggataggaga actcgag 1107

<210> SEQ ID NO 12
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 12
ggatccgagc cagtcaagca atcgggagaa tggcaccgtg ggcggctaag caaagtacga 60
aaaataacaa catgcgggaa tcggagcgtc cagaagtcaa ggaatggcaa gggtgcgcaa 120
atggaaaggt aagagggatg aacccataga gaaggtgacg ggatgagaac gctaagaaaa 180
tcccaaaata ggagagatag gagggtggac gaaatgccaa gatgacgcaa tgacagaagt 240
aacgggaagt gacagactgg cccacaatgc agaggtaagg ccctcaaccg aatcgggcga 300
tgaaacactg aaaacgtaga aaagtgcagc gactagcagg agtaaaacga tgcccgaata 360
aaaacctaaa ggagtgggag aatccacgag taagaaaatc aaggagtaac cgactcagaa 420
agatgaccaa ggtcaaggac tcaaaagctc ggagagtaac ccagcgtcac aaaatgagag 480
cctgcaaaaa tagaaacatg cggcaacctg aaacgctgcc agacagtggg aacgtccaca 540
ggtggaggga tgggaaagta caacactgac cagatcggaa aatggcaaca ctacgaaggt 600
ggatatctag cagaatgaaa agggtaaaga gactaaagca atccagaagt acaacgatag 660
gagcgtacga gaatgcaaag atgaacgggt acgacaagtg aaaaactcaa gagatacaac 720
catgcacgcg atagacacgt acaaaactac aaaaatgaac acacgtagga gagctgaaca 780
aagtaggccg catggagaag tacggcggct ggcagaatga aggcgtaaga gcactaagcg 840
gagatggaga cataagcaca tgggaacgtc aaaaaatcag agagtgcaaa cataaacaca 900
tgagctcatg cgagagtagc acaaatcgag aggtagaggc gtcgagggag tagcggagta 960
cccaacatgg accactggaa aactcagggc ggtggacgga tgaggaaggt acacgggtag 1020
aaacatagcg cgatgagagc aataagaaag gtgaaagcat gagagactac agaagatgga 1080
cacgataaaa acgtaggcaa gctcgag 1107

<210> SEQ ID NO 13
<211> LENGTH: 1125
<212> TYPE: DNA
<213> ORGANISM: Artificial Sequence
<220> FEATURE:
<223> OTHER INFORMATION: Synthetic polynucleotide

<400> SEQUENCE: 13
ctcgaggacc cactaaggca atgaaagcct agaggcatga cgggataaac gggctcggga 60
agctgccggg ctgacgagaa tggaggccta aagaaactgg agcgatcaga cagggtacga 120
cgctcacgca ggatgacagc aatacgacgc tacaggaatg gaaagaatgc gagagctaaa 180
acagtccaag ggtagagcgg tagagctcta gggaactaag aagagatgga gaaatagaga 240
cgatagaaac ctagcaaaat ccgaagctcg ggagatccag cgagtgagga gatacacgaa 300

-continued

```
tgcgagcgat ggcgaactgc caacggctga acacaatgag caaatggaga aataagcgaa    360

catagggcga taagagaccg cggcaacgtc gggaggtcaa caagtagagg aataaaccag    420

tgggaaaatc agaaaataaa gaggataaag gcgtcaggaa atgggaggaa tcgggaaatg    480

aacgcgtaag aagatagaaa ggatgccgag gagtcaaccg aatgacagac gtagggaaag    540

atacaacaat caccaaatca aaaagtgcga gcagtcgagg aatcgggagg tagaaggaat    600

gacaacgatg aagaacatca aaacgtgaca ccctaaggcc ctagagcgat aaaagagtga    660

ggcaatcgag ggatgcgcgc gtagacaagt gcgaacgtag accactaaga aagtcagcag    720

aataaacaga gtaaaccact agcaagatca aagactaaaa aactacgcac cgtagccaga    780

ctcgggcaat gaacggatca aaagataagg gaaatgacag gatgcagaag aataacggga    840

ctacaaggct aaggcagtca gaaagtaacg cactggcagg gtgaagacct gcaacagtga    900

aagggtcggg caatagcaga agtgaccaca tacgccaatc gacaagtaaa gaggtaaagc    960

aactaacgaa cgtacaagaa ataaccggct gaaaggaact agcgaaatga gggagtgaag   1020

aaataagcag aactagggag ctgcgacggg tggcagagag tcgagagata caaaggtaaa   1080

caaactcgca agggtgaaga gaccatggaa gcatgcaaaa gatct                   1125


<210> SEQ ID NO 14
<211> LENGTH: 1125
<212> TYPE: DNA
<213> ORGANISM: Artificial Sequence
<220> FEATURE:
<223> OTHER INFORMATION: Synthetic polynucleotide

<400> SEQUENCE: 14

ctcgaggacg ataagcaaaa tagggccgtg agacaaatgg cgacatgaag caatacccaa     60

gtgacaagct agagaggtaa cagcatagac aaccctaacg ggactagccc aaatagaaga    120

gtaaacgggt agggaactga ggacctgaaa acctgcaaag actgggcagg gataggaaca    180

ataagaagat gaacagatga gcgagctcgg gaaatgagaa aataaaaggc gtacgggagt    240

gggacagtca cgagaataaa ggcgtcggca gatcaacgga tgcagggcat gggacagtac    300

gggagagtac gcggctgaag agctgacacc ctgagggaag taggcaaata aaagggtagc    360

ccactagcga gcgtcaccgg gtggaaagct aggaacgtcg gaaactagga gagtcagcag    420

ctccgaagct gagaaactcg gcagatcacg gaccgcggga agatgaaaag ctgaggaggg    480

tggacgggtc agaacgtggg aaactagacg acgtgggcga atacgcacgt aaaggagtac    540

gacacatcag ggcctgggaa gataccaaga tgccggaaga tcgaaaacta aagcagtgga    600

acagtcaaca aatcaagggc gataagcgaa taaggaggtc agcaggtgga aaccgctaag    660

accgtgggaa actcaggaaa tacgggcagt aaggcggctg gcagactagc gacatgagcg    720

ggtcacagaa ggtaacgcaa taacaaaatc gcgcagtggc acagtaaagg cctcgggaag    780

tgcggagatg caagagtacc aaaggctaag gcactgggca cgatacggga actagggcga    840

ctgacagcat ccacgcagta agagaatggc gggatggagc gctaagacgg tgaaccaata    900

agggcctaac aggatgacaa ggatgcggga atgagccact aaaggaagta gaggagtaag    960

ccgggtgcga agctggaggg aataggaaaa tacgaggatg ggcaggtgag gagaaatcgg   1020

acggatgaac ggctggcaag gtaaaagggt agcggaatag agagcagtcc gcaggtcaaa   1080

cgggtgcacg ggctcagacg ggccatggaa gcatgcaaaa gatct                   1125


<210> SEQ ID NO 15
<211> LENGTH: 1123
```

<212> TYPE: DNA
<213> ORGANISM: Artificial Sequence
<220> FEATURE:
<223> OTHER INFORMATION: Synthetic polynucleotide

<400> SEQUENCE: 15
ctcgaggaaa aatggcaagc taagaggaat caagaactgc ccacctaaga ccaatgaggc 60
gataaccgaa atcgggcaat agccgaataa agggaatgag acgggtgcgc gactacacaa 120
gtgcgcaact aaaaaaataa cgaagtggga agcgctacaa agatgggcag atcggcaggt 180
aaggacgtag ggaagtacag gagctccgcg actaggacca tccaacactg gcaggataga 240
gcggtgaaaa gctggagaaa cgtcgggacg tgggcaggtc agagggtgca gaagtgacgg 300
gcataagcac atacaacggt agcagagtcg aaaacataaa gagactggac gaatcagaga 360
ctagcggact agccacctgg gagagtaccc gggatacaag ggataagagg aataggcgag 420
tggacagatg gaagcatggg aggatcacag aactagggag atagcgagat accagcgtgg 480
agaagtaaaa aaatgaggga ctaagggaat gaaaaagtaa gaaacccgcg gggtacacca 540
gtgcagcagt aggagaatac acgaatgcag ccagtcaaga gaaatgaaga actaagagag 600
tgcgagagta cagagctacg caagtgccca agtgagagaa tagcgggcct caagcgatca 660
acgacataac aggagtcagg agaatcgcaa agtcacggga tgcgagcagt ggacaaatca 720
gcaaaatcaa agactcacaa gatccgacaa tagagggata aacaagatac aaacatccag 780
agactggcag gataaagaaa gtacaaagcg tgccaagcta aggaagtaga gaaatccaag 840
aatacagagg tgacgccgtg aagacatgcg caggtgagca ggataggaga ctaaaggcgt 900
acgggaatgc gaaactagaa ggctgaaagg atcgacccac tcgcagcgta gagggctacg 960
acaactaaag acataagcag atgaagccca tcaaggacat ggcgcgatgg gaagatccaa 1020
gagatccaag ccctaggaaa gatgaacgcc tgaacagcta agagcgggtc caaggataag 1080
aacatgcaga aatggacgag ccatggaagc atgcaaaaga tct 1123

<210> SEQ ID NO 16
<211> LENGTH: 1125
<212> TYPE: DNA
<213> ORGANISM: Artificial Sequence
<220> FEATURE:
<223> OTHER INFORMATION: Synthetic polynucleotide

<400> SEQUENCE: 16
ctcgaggacc aaaagtcaag aaagtaccgg gctagaagag ctgaagccat aagcgagtag 60
cagaatagaa agatcccaaa agtcccaggg atagacgagt aggaaggtga aaaaatggcg 120
aggtagcgac atgcaaaggt aaaacgatga aaaactacga gggtggaaga ataagcaggt 180
gacgaagtaa acgggtcaaa ccgagctcag atcgaacgat aggaaacatg accgggtcac 240
acgatcgaga ggtcccaaag gatagaagaa gtgaaaaggt gagcaaggtg gcgaaaataa 300
aaagataaaa gaataagaca gtagcgggaa tacgacacta gaaggatcgg gacatgcagc 360
agtaaaccaa taggaggata acagggcatg gaagagtggg acggtaagac cctacacgaa 420
tacaagcagt gccaggatgg cgcgagtgac aaaaagtaga agggtgaccg agtcgagaga 480
tagagacgta aggaagtagg gaaggtggga cgatcgaaag atcgaagagt aggaggcgtc 540
gaaaaatccg gaaaataggg aagatggacg gatcgggacg gtgaggagga atagcaaaag 600
tcccgcgggt acgaaaggtc gggaaggtca agcaatcagg cgctcaacgg gactgaacaa 660
ataaggacat acacaagtcg gcacgtcacg aactcaaaag gtggagaagg tagcgaaatc 720

-continued gaggagtgga gaaggtaaag aaatgggaag gctaaagaaa tggcagggta gagaactggg 780
acggtaaacg catgaaagaa tcagggagta gaagaacgtg aagggatagg agaactcaac 840
agggtagcag aagtggaaag catggcaaga atggcagcat gaaaagatcc aggagtaagc 900
gagctgaaga aatggagacg taacaacata gcgggagtag gcgcgtgaca agataacgcg 960
aatgcggagg tcgaggaatc cgcaagtgaa cacgtcaacg caatgaacgg atgaacacat 1020
gcacgaagtc gacaagtaaa aaacgtggaa gccatgacaa cataacggga tggcaggata 1080
agagagtaga acgatgcacg agccatggaa gcatgcaaaa gatct 1125

<210> SEQ ID NO 17
<211> LENGTH: 1108
<212> TYPE: DNA
<213> ORGANISM: Artificial Sequence
<220> FEATURE:
<223> OTHER INFORMATION: Synthetic polynucleotide

<400> SEQUENCE: 17
ccatgggaca gcgatcagag ggtaaaacgg gatgaagcag tgaaaggacc tcagcgaatg 60
aaaaacgatg gccagatcca aagataaaaa actgaaagac tacggaaata caagaataga 120
agggtaaacg actgagaaag tacgaagcct agacgggtaa aaaaggtcgg gaagggtaac 180
gccatagaca aatgagaagg taaaggcatg gaaaaaatgg aggcatcgac gaatgcccgg 240
ctcaaaggat aacggactag cgcggtaaaa gggaatgcgg acgatcgaag aagctccgga 300
ccgatccacg gaatagagac atacgacagt gcgccaaatg gaccgataaa agggtagacg 360
aaataacagg atgaacagga ctcggagaaa taacaaagtg gagaaagtac aaaagtcaac 420
gaataggcca gtggcaaaag tgagcgagtg aacaggtaga ggagtggaaa agtacaaagg 480
atgcaaaaat gaaaaggtag aaaactaagg cagtacaggc ataaacgact cacaaactag 540
aaaactacag cagatcgaag cataaaggaa ataggagaga ataaaaacgc ctaacaaact 600
acaagaacta cgcggagtgc gagacgtcag gcaagtgagg acctgaaaca atgcaagaat 660
ggcgaagtgg acgcggtagc gggataagca aatacaccgg tagatatcat aggaaggtca 720
cgcaaatgga ggagtcaaga aactggccaa gtgaagccct cggcagatac gcaaagtacg 780
acaaataaga ggctcagaag atccagacga gtgcaggaat aagacaatca agagaatgaa 840
cgcatcggaa cactaggcag cagtgggacc ggtaaaagca tagctagctc gggcgatgga 900
ggcacgtaca aaggtgacaa aagtaacggg aatacccacc gtaccaggat gaccagggat 960
cgcgaagata gcggaatcga gccctcagga gctaggccag catagagacg tcacgagatg 1020
aagggataaa ggaagtcaaa gaatgggaga actccggacg tacgaggcta cagaggtgaa 1080
aagataaagc agggtgagga aggcatgc 1108

<210> SEQ ID NO 18
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 18
ccatgggaca agagatagaa agcagtgaaa gaataggacg gtcagaggat ggagggcctc 60
cgggcgtggc acgactagga cgatgcggaa ataacgacaa gtggaaacct agccagctaa 120
ggaagctaag ggcaatggca aagtaaggaa gtacggaaat aggaccatag aagactggac 180
cgatacagcg ctagggcggg taaacgagtg aaagggtgga acaataagga cagtgcagca 240
ggtaagacca ctaaaagact ccacgacgta cagagactcc gcgcctggaa cgatcgaagc 300
gtaacgggca taaggaaaat agagaaggtc gaggaaataa agggaaatgg agaaactaag 360
cggataggga aataaacgaa cctcagggaa tcccaaagtc cgaccaatga cagactgcac 420
gcatccgagc gtaaaaacat gagaccaata acgagatcgg caagtcgaga agtcgcagaa 480
tcaaacaacc tgagaacctg cgggagtgaa cggataagac ggtaagagaa ataagagcat 540
gagaaactgg gacgatagaa cgatagccaa gtaaaagggt aagagaatgg aacgaagtgc 600
aaaaagtggc agaatgaaca gataggcaga tcagaagaat gaggaagtcg cagaaataag 660
agggtgggag cgatgccggg atgcgcgaat gcgaaggtaa gagaatgcag gagtaaagag 720
gactgaaaag atcgggacat gaaacgatag gaaggtacgg cgatgagaca gtacaaaagt 780
gaaagggtga cagcctgcgc ggatatcagg gatgccacga tgggcacatg cccaaaatga 840
aaaaatcacc aaataccaaa atgaagccga tgcgggaatg cgctagctaa cgagcataaa 900
acggtaggaa aatggaaagc taaccgcagt ggaagaataa ggagctacgc aaatacgccg 960
aataaggaag tagcggacta aggaggtaga cgaataggcg aataacgcga gtcgagaaat 1020
ccaagactac aggactcagc agatgaaaaa actagaaacg tgaaggccta agaaacataa 1080
gacactgaaa gagtagcgga ggcatgc 1107

<210> SEQ ID NO 19
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 19
ccatgggaga gtaaggaaat gagaacagtg aagacatccc aagaaatgaa aaaagtggag 60
aggtcgaacg gtagagcagt ggagaaggat acgccgatcg ccgggataac cgggctaaac 120
acaatgaaac acgtggccga atacggagga atcagaggag gtggcaggac tgaacgagtg 180
ggcgggatag aaaaactaca gcgatacgcg cgataggaac ctacgagaac taagaggata 240
aagacataag ggcctacgca cgagtaaaag agtaccgacg tcagacaata gaagggtaaa 300
aagatgaacc gatgagcaaa atccaggcgt cgcaaggtca cgcagtcaag acataagaga 360
atgccagaag tacaagcctg ggacggctga gagagatcgg gcagtcaaaa gggtcaggac 420
atagcgggat agccgaatgc aaagatacga cggtgcaaga atcacggcat aggcaagtgc 480
aaaacgtaac aacactggcc aaaatggaag actgaacgca tgacacgggt cacgcagtgc 540
agacctgcaa cagtacagaa atggaaaact agaagagtaa gcaaatcgaa acctccaagg 600
gtggaaggat ggacaggtga acaggtaaag agatcgcgga catgagaagg tacaaagcta 660
aacaagtcgg gaggtgaacg aataaggacg ggtaagggac ctggaccgga atggcaacat 720
gcaaacataa gagggtcaac caatggaagg ctgaaaagat cgaaaaatgg gcgaatacaa 780
aaggtaaagg gatagcggga tcagaaggtg ggacgatgaa agaatgaaga aataccaagc 840
gataacacga tccggaactg cgggagctga acaagtcacc gctagccaga gggtgcaggg 900
gatatcaaat gggcagatac ggagcgataa aaacatgaaa ggagtgggcc actggaagga 960
tcagcacgta acggcctaaa ggactaagag cacatgagcg aagtgaagag agtgaagaaa 1020
ctaagaaaga gtagagagat gcgagagata gcgaaaatcg acaacatcgc gggagtggaa 1080
aactgacggg atgacgagaa gcatgc 1106

<210> SEQ ID NO 20
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 20
ccatgggaac agactaaaag aatcaacaga tagaggaatg aggaagtgca ggaagtaagg 60
aaaactggaa gagtaacaca atgggagaat acaaaagtca accagatgga cagatagaga 120
aatgacgaga tggaaacagt cacacgctaa gggaatggac gcgtgaccag atcgggaaga 180
tccgggcaat aggacagtag aaaggtgcag gaatgacaag atggccaaat cacagcatag 240
agccaataag acggtaaaag gcgtagcacg ataggacggg tcacgagagt gagagaggtg 300
ccaacaacta ggacaataag ccgataaaag cgtcgaacaa tagagacgtc cagagaatgg 360
acccaatcca ccggatagca agagtagcgg agataagaac gtcaggagat agcgaagtca 420
cgaaatgaga gagtcacgcg gtagcacaat aaagacgtac aaaagtacaa caaagtgaga 480
acatcaaaac gataagcagg ataaaaaggt aaaacgggat cgggacgctc gaaaactgac 540
gaactagaaa agtaagaacc tagaaaaata gcggcataga aaactaaggg aatggcgaac 600
ataagaggaa taggaaggtg gcgaagtgga gcaataaagg aggtgggacg gtcaagagct 660
agagaaatcg caacgatacc ggaatcggga agtagaacaa atcagcggcg taggacaagt 720
ccgggaatcc acgagtcgaa aaaataagac actcagagag tgcggaggct aaacgggtgg 780
aaagaactgg aaagatccag agcatcgcag aataagacga gtgcgcggat caacggataa 840
ccacctaagg gcgtcgggcg ataacggcag taccgaaatg ggctagccac gggatgggag 900
aatggaaccg taggaccggt agagaaagtg gaacactacg gagaatgcaa cagtaggaaa 960
gctgacgggc taaggccggt aggacaagct ccgcgcgtga agatatcgcg gagtagagga 1020
ataccgggcc atgacgggca ctcaacggct gaaagagctg aagcaggtgc aggactggga 1080
ggagtaggga cgatcacagg agcatgc 1107

<210> SEQ ID NO 21
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 21
gcatgcgaag aaaagtggaa cactaggcgg gtgaacggga tgaaaaggat agagcggtgc 60
gaaagtcaag aaataggaga actaacgaag tgggagagac taaagacgtc agaagatcaa 120
aaggtcggag gcaatggaga agtgcagcaa tcagaccgtc cggcgctgaa aaccaatgaa 180
gacagatcca agagctgagc agctagcgaa gagtggcgag cgtaaagcag tagggaggta 240
aaagaactac aggcctcaga caatccagac gtaagaggga tacagccgtc agggaggtaa 300
gagaatgaaa ggatgcgccc atgagccaac tgggagggct aaaaaactag aagagtgaaa 360
aactggcacc gtgagaaaat agcacaatac gaaaggtcga gaaatcggga aagtgcggaa 420
gtggaccact agcgagatca acagagtagg gacatcgaag aataaggcag aatgcgacag 480
tacgggagat cgaaagactg cgagcgtgac gagatgaaga ggtaaaaaac tgaaaacatg 540
aggcggtgaa agggaataac caggtgggac acagtgacgg gcatggcggg cctcaagaga 600
tgcacgactg agcaggtgag aaggtacaca gatacgagaa tggaacggct caaaacaata 660
agaaggtcgg cccgtgagac caggtaagag agctggagga cccgcggagg tgagcgggtc 720
aaaaaatcga gagataagga gagtgaacgg gtgaagacag tagaaaaatg agagaaatcc 780
ggcaaatagc aggactggac gcgtacgaaa gagtggcaaa ataagcggat ggcgagatgg 840
cgggctcggc gagatagcaa gatgaagacg taagaacggt aaaaggctca agagatgaac 900
aaataaagag atacgcggct aaaagaccta aaaggataag aaactcaagg cagtgacgaa 960
acgtgcaagc agtaacagaa tgagaaagga tgaacaccgt ggcgggatag gagagtggag 1020
aaatggaaga atacaagaat aagaacggtc ggacgcataa acaggtaagc caataagaga 1080
ggtcagcaca cgtacgaagg aagatct 1107

<210> SEQ ID NO 22
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 22
gcatgcgacg gatagaagca tggcagagga tcagggaagt caaacgaata caaagatagc 60
caactaggac caatcagaga ctgagaagcg taagcgaagt acgacaatcg gaaagtcgag 120
ggatgcgaga gatacaaaag taagagggta gaaggcagtc gggagccatc cgggagctaa 180
caaaataaag aactggcaga ggctagcgct ccgggagata ggaaggatga caggccgtcc 240
gaaagtacgg aaatcaaaaa gtgaggcact cagagagtga aagcgtaaga acgggtaggg 300
agctaggcgg gtaggccaca tcacgggata aagagatgac aagcgtgaag gaatccacgg 360
agtgcgcaga cgtccaaagg tccacaactc cgccgggtac aacggtgaag caaatcacgg 420
gctcgaaaag gtggcgagat gggaccatga aagaatcgaa gggtaagacg atccagagat 480
gagcccataa caaggtaaca acctaacaga agtaccagaa tagagcaact gaaaaagtac 540
agcactggca acgtccaagg ctcgcggcct gcgcgcgtgc gccgaaataa ggacaataac 600
gacctaggac cgaatacaaa agctaacaga ctcagagcat ccaacgctga gccagtcaga 660
aggtagagaa gtaagcgaaa taaagaaaat aaagaaatgc cgcgatcgga aggtgaagaa 720
ctaccaggct acggagaatg aaagggtaag agggtaagga catacaagaa taaagaagct 780
aggacaataa acgccctaaa accgcggaga gaatagcccg atacaagcgt ccgggcatag 840
aaacctggag aaataggaca ggtgaaaggc tgggcacatg accgactgga gagcatggaa 900
acatacaccc agtcaaaaag tcgaggaata gccgggtggc acggtaacaa aatcaagaaa 960
ataccggagg gtgcagaagg gtacgaccgg tacaggacct aagaacgatg gcgagagtcg 1020
ggccgtgagg acagtaagga cgtggaggaa gtagcagaat agcgggatag ccagctacga 1080
agaaatgggc aagtgcggag aagatct 1107

<210> SEQ ID NO 23
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 23
gcatgcgatc gaaaaatagg gaggtggccg gctgcgaaag tcgggcgggt gaaagcaact 60
aaaaggatcg aagcatgaaa gagtaggaaa gtggaagaat gagaagataa cgaaataagg 120

```
aaggtaaaac ggtggagaga tagaggacat aacaaagtgg aaacactcaa gagctaaggg    180

aactagaagc ataacggaat ggctagcatc gggagagtag cggcatgaag cgatagggaa    240

cgctgacaag aaataaccga atcgggaaat caaaccatag aagactagac gggtaacaga    300

atggaggcaa taggaaacgt aagacactaa cgggatacca cgagtgacaa gatcggagga    360

tggcaccatg aaaagataga gagctagaag ggtacgggaa tagaaaaatg caaagctagg    420

gccgtcgacc ggtgagaagg gtaaaaaggg tgacaaaatg agagaataac cagataggga    480

cgtgaaaggc taggcacctg gagacaatga ggcagtacac gcgtaccaag atccagagaa    540

tcagacggtg agacactgga caccataaga agatgaggag gtgagggaca tgaaacaata    600

acaacaataa ccacataagg gcctcgaaac gtggagagca tacagccggt gcaaaagtga    660

gacggatgcg aaaaatgaac aggctgggac gatacccaga atgccaagat ggcggcctgc    720

cgggatcacc gagtagccaa cctgacaaaa agtgcggaaa tacgggcatg agaaggtgga    780

gcactcagac gatgaagacg atacggacgt accaaaatgg aaaacaatgg gagcgtaagc    840

aaaatcagac ggtagaacgg taaagagatg cacaagatga agagcatcaa cacatgacag    900

cccgcgggag taggcggagt aagcgggtaa cgaggtgagc acataaaaag gtcgcaaagt    960

acgaaggtaa gggagtggag agagtgaagg gcctggaggg agtcggaaca atgccgacgt   1020

aagcaagtca aacgctaagg caagataacg gaatgcgaaa ctggcgccct aagaacgtag   1080

gaccataaca aggtagaaaa aagatct                                       1107


<210> SEQ ID NO 24
<211> LENGTH: 1107
<212> TYPE: DNA
<213> ORGANISM: Artificial Sequence
<220> FEATURE:
<223> OTHER INFORMATION: Synthetic polynucleotide

<400> SEQUENCE: 24

gcatgcgatg gaaagctgag agaaagtcag aagatcacag actcaggagg atcgggcagt     60

agacacgtaa gaaggtagag gccaatgaca ggctgaagag gtgaaggcct aaaagaatac    120

gcgggtcagg aacaatgcga agcctgggac gatcgggaga taaaagggat agagaaatgg    180

ccgaatagac cggtacggcg cgctagcgat aaggaactag acgggtaaaa ccgtaggaag    240

ctcagaaaca taacgaaagc tacagcaggt aagcaagcta agaacctgag caggataacg    300

cagtaaggac actacgggaa ctaagccaga tgaccgggta cgaacgtcaa acgaatagca    360

aaggtgcggg acgtggccga agatagaaaa catacccaaa tgccggaatg ggagaatgcg    420

caagtaaaaa cataggaaca gtaaggcaat cgggaggtga aagggaatga gacaactaac    480

aaggtgggaa aaatccagca gtaaacagca tagggcaatg agaaggtaga acaataaaga    540

cgatgaggaa gtaaaaacgg gtgggcaaat gacacgatga aaaagtaacg gagtaaaccc    600

actcagaaac tggaaaaagt cgaaacatgg gaagaataca ccacatccag cgaataacgc    660

gactcccaac caatagacga gtgaagagat ggaagccctg gcgaacatgg agacaatagg    720

agggtcaagg acgtggacac gtacagcggt aacggcctca gcaggtggga ggctacgacg    780

aatggaggag tgcagcaata ggcgggatag cagcctgcaa ggatcggcaa ctgagaaagt    840

gaagagaatg ccaaccctgc aagcgtaaaa agcgtgaagg cgtccagaag tacgcacact    900

ggacaaatag acgaataagg gcctcaaaag catcgcgagg ataagaaagt gcgggagtaa    960

caacctcggg aagtcggaaa gtagaaaggt ggaccgataa cccgcgggca caataaacga   1020

actgcgagca tcagagaggt gcagaagata ccacgagtag aggcatggga acgtgaaaac   1080
```

aataacgcaa gtcaggacga gagatct 1107

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 25
ggtctgtgtg atgtt 15

<210> SEQ ID NO 26
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 26
aacatcacac agaccaacat cacacagacc aacatcacac agaccaacat cacacagacc 60
agccctttg 69

<210> SEQ ID NO 27
<211> LENGTH: 3194
<212> TYPE: DNA
<213> ORGANISM: Artificial Sequence
<220> FEATURE:
<223> OTHER INFORMATION: Synthetic polynucleotide

<400> SEQUENCE: 27
aagcttggcc acacagcttg agtattctat agtgtcacct aaatagcttg gcgtaatcat 60
ggtcatagct gtttcctgtg tgaaattgtt atccgctcac aattccacac aacatacgag 120
ccggaagcat aaagtgtaaa gcctggggtg cctaatgagt gagctaactc acattaattg 180
cgttgcgctc actgcccgct ttccagtcgg gaaacctgtc gtgccagctg cattaatgaa 240
tcggccaacg cgcggggaga ggcggtttgc gtattgggcg ctcttccgct tcctcgctca 300
ctgactcgct gcgctcggtc gttcggctgc ggcgagcggt atcagctcac tcaaaggcgg 360
taatacggtt atccacagaa tcaggggata acgcaggaaa gaacatgtga gcaaaaggcc 420
agcaaaaggc caggaaccgt aaaaaggccg cgttgctggc gtttttccat aggctccgcc 480
cccctgacga gcatcacaaa aatcgacgct caagtcagag gtggcgaaac ccgacaggac 540
tataaagata ccaggcgttt ccccctggaa gctccctcgt gcgctctcct gttccgaccc 600
tgccgcttac cggatacctg tccgcctttc tcccttcggg aagcgtggcg ctttctcata 660
gctcacgctg taggtatctc agttcggtgt aggtcgttcg ctccaagctg ggctgtgtgc 720
acgaaccccc cgttcagccc gaccgctgcg ccttatccgg taactatcgt cttgagtcca 780
acccggtaag acacgactta tcgccactgg cagcagccac tggtaacagg attagcagag 840
cgaggtatgt aggcggtgct acagagttct tgaagtggtg gcctaactac ggctacacta 900
gaagaacagt atttggtatc tgcgctctgc tgaagccagt taccttcgga aaaagagttg 960
gtagctcttg atccggcaaa caaaccaccg ctggtagcgg tggttttttt gtttgcaagc 1020
agcagattac gcgcagaaaa aaaggatctc aagaagatcc tttgatcttt tctacggggt 1080
ctgacgctca gtggaacgaa aactcacgtt aagggatttt ggtcatgaga ttatcaaaaa 1140
ggatcttcac ctagatcctt ttaaattaaa aatgaagttt taaatcaatc taaagtatat 1200

```
atgagtaaac ttggtctgac agttaccaat gcttaatcag tgaggcacct atctcagcga   1260

tctgtctatt tcgttcatcc atagttgcct gactccccgt cgtgtagata actacgatac   1320

gggagggctt accatctggc cccagtgctg caatgatacc gcgagaccca cgctcaccgg   1380

ctccagattt atcagcaata aaccagccag ccggaagggc cgagcgcaga agtggtcctg   1440

caactttatc cgcctccatc cagtctatta attgttgccg ggaagctaga gtaagtagtt   1500

cgccagttaa tagtttgcgc aacgttgttg ccattgctac aggcatcgtg gtgtcacgct   1560

cgtcgtttgg tatggcttca ttcagctccg gttcccaacg atcaaggcga gttacatgat   1620

cccccatgtt gtgcaaaaaa gcggttagct ccttcggtcc tccgatcgtt gtcagaagta   1680

agttggccgc agtgttatca ctcatggtta tggcagcact gcataattct cttactgtca   1740

tgccatccgt aagatgcttt tctgtgactg gtgagtactc aaccaagtca ttctgagaat   1800

agtgtatgcg gcgaccgagt tgctcttgcc cggcgtcaat acgggataat accgcgccac   1860

atagcagaac tttaaaagtg ctcatcattg gaaaacgttc ttcggggcga aaactctcaa   1920

ggatcttacc gctgttgaga tccagttcga tgtaacccac tcgtgcaccc aactgatctt   1980

cagcatcttt tactttcacc agcgtttctg ggtgagcaaa aacaggaagg caaaatgccg   2040

caaaaaaggg aataagggcg acacggaaat gttgaatact catactcttc ctttttcaat   2100

attattgaag catttatcag ggttattgtc tcatgagcgg atacatattt gaatgtattt   2160

agaaaaataa acaaataggg gttccgcgca catttccccg aaaagtgcca cctgacgtct   2220

aagaaaccat tattatcatg acattaacct ataaaaatag gcgtatcacg aggccctttc   2280

gtctcgcgcg tttcggtgat gacggtgaaa acctctgaca catgcagctc ccggagacgg   2340

tcacagcttg tctgtaagcg gatgccggga gcagacaagc ccgtcagggc gcgtcagcgg   2400

gtgttggcgg gtgtcggggc tggcttaact atgcggcatc agagcagatt gtactgagag   2460

tgcaccatat gcggtgtgaa ataccgcaca gatgcgtaag gagaaaatac cgcatcagga   2520

aattgtaagc gttaatattt tgttaaaatt cgcgttaaat ttttgttaaa tcagctcatt   2580

ttttaaccaa taggccgaaa tcggcaaaat cccttataaa tcaaaagaat agaccgagat   2640

agggttgagt gttgttccag tttggaacaa gagtccacta ttaaagaacg tggactccaa   2700

cgtcaaaggg cgaaaaaccg tctatcaggg cgatggccca ctacgtgaac catcacccta   2760

atcaagtttt ttggggtcga ggtgccgtaa agcactaaat cggaacccta aagggagccc   2820

ccgatttaga gcttgacggg gaaagccggc gaacgtggcg agaaaggaag ggaagaaagc   2880

gaaaggagcg ggcgctaggg cgctggcaag tgtagcggtc acgctgcgcg taaccaccac   2940

acccgccgcg cttaatgcgc cgctacaggg cgcgtccatt cgccattcag gctgcgcaac   3000

tgttgggaag ggcgatcggt gcgggcctct tcgctattac gccagctggc gaaaggggga   3060

tgtgctgcaa ggcgattaag ttgggtaacg ccagggtttt cccagtcacg acgttgtaaa   3120

acgacggcca gtgaattgta atacgactca ctatagggcg aattagtgga tgagaagacc   3180

tgcagaaaga attc                                                    3194
```

<210> SEQ ID NO 28
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 28

```
tctagagaga aaggctacga agatccggac atcaaaagat caaaacatgc ggagatcgac     60
```

acatccaaaa atgaacagat aacaggatca gagggtcaag aagtgaaacc atcgaggagt 120
cgcagactac gaagatggac aagtgagcaa cagctgcgat ggagaactaa aggagtcggg 180
aggtacggca gtgaagaaat gtgcacatga aaagctgccc gggtgcgcaa ctggaggact 240
agaagaatgg cacagtgacc cggtgagagc ctgaggaggt gcgagaatag ggcgataggg 300
aggtaacccg atggcggact aaagagatac ggacatggac ggataggaga gtcgcaagat 360
ggaaggatca caaagtgagc cggtccaagc atacgcgggt aaacggatca gaacgtaaag 420
cggtggaaaa atacccgagt aggaagatag caaaataccc aggtcgagcg atagcccact 480
cggcgagtcc aaaactgaaa aaatggagag atgagacact agcggcatcg gacagtagag 540
cagtgaacgc atcagagagt agaaaagtga agaactgcga cggtgaaacc ataacagagt 600
cagagggtac acccatacga ccctaccgca atacaaggct aagacggtca gaggatggac 660
ggctcgcgaa ctcacgccgt gccaaagtga agaagtacca aaataggagc gtaacggcgt 720
agagaggtag acgagtgaga cggtgggcag ctcccaaggt ccgagcatgg acaggtggca 780
aaatccagcg gtcagaaact acgagactgg ccggatgaag aaataaggcg ctagagagat 840
acgggagtga caagatggac cactagcgaa gtcggagggt gaagacgtga acaactagac 900
cagtacggca ctagcagaat agaccgatga aaacctgaaa agataacaga gtgaaggcat 960
cggagggtcg agaagtaaga acgtggagcc atacacgaat aaagcagtac aagggtggac 1020
aaatgaggaa atcgggaggt cccacggtga aaacgtaggg aggtgaacca gtgggagagt 1080
caaccaatac gaagatgcga ggatcc 1106

<210> SEQ ID NO 29
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 29
ccatgggaaa atgagagccg ctcgacaagg ataaagaaaa gtcgcccaac atccgccacg 60
ctaagcggcc ctaggagccg gtaaacaagc atgaagaaac atgcgaggca atgacacaaa 120
ctccaggcgg gtggaaaaga ctcgacggag atgccacgca atagcgaaac ctggaagaga 180
gtggaagcaa ataggaaaca gtagagcaaa atgccgcagg atagaaaaca gtggcgcgca 240
ataagcagga ataaagcaca ataaaaagaa gtaaaccgca ctaaaacagc atccagaccg 300
ctgaaaagaa atggcggcga atgaaaaaaa gtcacaaccg gtgcaacaac ctgaaaaagg 360
gtagagagcc ctcccgggca ataaaagacg gtaagaggaa atcccgaaaa gtgcaaaaag 420
gtcaaaacgg gtgcaacaaa atgccaaggc gtgcaagaaa ctgaggacgg ataaaagaca 480
atgcggacgg gtacgacacg ataaggaaag ataaggcgaa gtaaaagccg gtgcggcaaa 540
atacaacagg ctgcccagaa gtaccgagcg ctaggcggga atgagcgagg gtaaaagaga 600
atacacaacc ctgcaagaaa gtccgggaag ctaggaccgg atacagagga ataaggaagg 660
gtacacagca atacgagcag atgaacgagc ataccagaga gatatcaggc ctaaaaaacg 720
gtaacaagaa ctaggaggag gtgcgaaggc ctggaccaaa atgggacgaa gtaggaggga 780
atacacaacg atgggacgag atagagccgg gtaggccaaa gtagcacggg ataccacaga 840
atacagcgac gtaccggaaa gtaggagaga ctggaaaccc gtaaggcaag ataagcgagg 900
gctagcagaa ctaaaacaga ctgaacacgg atcaaggcga gtaggcacga gtacacgccg 960
atacggacaa gtaggccgca gtacggagaa gtaaacaggg atgagagaca gtgaacaagg 1020
ctgagacgaa atcacagcaa atacaacaaa gtagcggcaa ataaacggga gtggaacgcg 1080
atagcaggaa gtgacggaca gcatgc 1106

<210> SEQ ID NO 30
<211> LENGTH: 1169
<212> TYPE: DNA
<213> ORGANISM: Artificial Sequence
<220> FEATURE:
<223> OTHER INFORMATION: Synthetic polynucleotide

<400> SEQUENCE: 30
gaattcgagt accacctgat gagcagcaag gtaacggcga agatgaaaag aaaaatggag 60
cggcacgtac aaaaaaggat ggcaccagac atagaagagg agctcagcaa acggctggac 120
agcgaagtcc caggaagcct accaaggaca gatatcaaag aaataagaaa caaactgaga 180
aagcgcgtcg gaagcgacgt acaagcggca atggcagaga gagtaaaaca aacagtgaaa 240
ccaacaataa acgcccaggt agggcgaaag gtaaacaaaa ggatcgaaag acgagtaagg 300
cgggagatgg aaacaacggt gcgaaaacca gtgaaaaagg gagtccaaag caccatgaag 360
accacaatac gacacaccct gggaggacac gtggaggagc cggtacgaag cagggtacaa 420
gacaacatgc aaacagaggt aaaggaaccg ataaagaacg acatggaagg aaacgtagga 480
acccgagtag aggaacggat agcgaacgac gtgcaacgcc acctagaacg agaagtcgca 540
agggaaataa acggagaggt cccacggccg atgagcagaa aagtggaaaa ggacctgaag 600
agaaaaatga ggaccacaat aaaggacgga ataaaaaaca cactcccaga ggaaatacaa 660
cgagaaatag ggaacaggat gcaaagaagc atcagaaagg cagtgccaaa gggaatcgga 720
cgcaagctaa gacaggccct agaccgcgaa gtaaacgaac aactcggagg gcgaatcagg 780
cccaccatgc agagcaaaat aagagaccag atgcgcggca acctgagacc gaacctaaag 840
gaaaggatag agggagaggt ccaagaaacg atggcgggca ccatgagaaa ggaagtcaaa 900
gtgcacctag caacacagat accacgagac atcgaagcga agatacggaa aaagctggag 960
agggcaatga acagaaagct acggaaagaa gtcaaggaca caatgaggga gcaagtcgag 1020
agcgaggtgg cccgccaaat aggagcaaca atgcgaggcc aagtgggcac aacgatgaaa 1080
gaccaactaa cacagccact tctagagtgc acggatccct cgagggtacc aaccatggaa 1140
gctagcaagc atgcaaactg cagaagctt 1169

<210> SEQ ID NO 31
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 31
ctcgaggaaa gacagagggt agcaggccac agatcaaggc ggcgaaatgg cccggagcac 60
gtaagcacca cacggtcacc aagagagaat cagaagaggc aagtaaaaaa aagcgcgtac 120
ggcacccaag gtggacgcac aacagtcacg ggaaagaagt cgaaggcggg cgctcagaag 180
agcgaagtac acaaccagac ggtaccggaa cacgatgcgc caacaagaat cagcggaaag 240
acataccggc ggacgggtcg aaacacgaaa atgaaaccgc agaagtaaag agaaaaggat 300
cgcaggaaga ggatcaagac agaaaaatcg acaaagcaaa gtggaccgaa gaagatcgaa 360
aagaagcact caggacagct gaatcgcaca gacacggtga caagacgaaa atggacgaca 420
accgataagc gaaaaaagat accggcgagc gagtcgagaa cacgaagtca aggcgcaaga 480
atagagcaaa cgaagtaaac aggacagaat aggaagggca aagtgggaga gaaaggctcg 540
gaaccgacga ctgcaccgaa caacgtggga gcccacggct acaaaacgcc agatcgaagc 600
ccaggagtcg aagaacaaaa gtaacggcgc agaaatagag agaggaggct aaagcggaac 660
cagtgaagga aaagaaataa cgggcccaag gtgaagaaaa agaagtggca ggaacggagt 720
acagcccagc aactgggcaa aagcggctga cgagaacaag atagagaacg aggaatgacg 780
agacacagat agaagacaaa gactgcggac aggcaagtaa gagaaggaaa ataaagcgag 840
agaagtaggc cgcccgaaat gcaaaagaaa aagtgacaca gagaaaatga ccggcgggag 900
gtaacacgcc caggatgacg gagcaccaat agaaaaaaac acgtaggaga gggaacatgc 960
ggacaagaca atcccaaccc gaagataaac accgagaggt agacagcgca gactggagga 1020
acagccgtgg aaagggaaag gtacgcaaac ggacctaaaa aaaacaaagt cagggaaaaa 1080
ggctaacgga acaaagctgg ccatgg 1106

<210> SEQ ID NO 32
<211> LENGTH: 1241
<212> TYPE: DNA
<213> ORGANISM: Artificial Sequence
<220> FEATURE:
<223> OTHER INFORMATION: Synthetic polynucleotide

<400> SEQUENCE: 32
gaattctcta gagtgcacgg atccctcgag ggtaccaacc atggaagcta gcaagcatgc 60
gaggaaagca aggaaaatga agaacgaagc gggtcgaaca gggaagacat aaaaaacagg 120
caccatgaca ccaacgcgga atgacacaac acaaaggtag cgaggcacgc acgtaagagg 180
cacaagaaat gaaagaaaaa gagaatacgc agagagggca gtaaggcagg gaaacgatga 240
gcagacgacg ggatgctagc agcgaaagct gagaagaaga gaccctcaaa aagcaaaaga 300
ataagaaagc caaagcataa aagaaaagcg caatcaagga aacgggcgct agaagaccga 360
gacagtgaga cgagcacacg ctaaaaaaga gagacaatcc agaaagaaga cagtggacaa 420
gagaccgggt agcaccagag gacaatgaag gcgggacggc ataaacgccc aaacgggtaa 480
gacgggccaa cgataaagga agacgaaggt caacgcagaa gggaatccag aaacacagac 540
ataaagaaaa aaagaaatgg cagccggaga agctgagacg ggaccgcagt gcgagagaag 600
agacgtgcgg aaaagagaag gtcgcgcaag acgggcgtgg accggacaaa ggatgggaaa 660
acgaccggat ggagagcgcc cagagtcaga aacggaagag atgaaaccca gaaagactcg 720
ccacaagaag gagtcgggaa acacaagaat aaagcagctg gggaatagcg gacgaacgga 780
atagaggccc aaagaactgg gagaggacag ccgtacagga ggaacgggat agcgaagaac 840
caacgtgcga aaagaccggc ataaaacaga aaggcaatag cagacagcaa aaatagagag 900
acaacgacgt agaaagaggg aaacgtcgca aaaaaccggg ctagaggagg accaacatag 960
cgagacacca agatgaagca acggagaagt cacacaaaga gacagtcgaa aagcaaagaa 1020
atagcccagc aagcgaatac ccaacaagaa gagtcaacag gagaaagagt ccaaggagaa 1080
gcaagtacac aagacaaaag gtagcagaca caagcaatgc acgggcaggg aaatgcgaaa 1140
cagagaggat aagaagatct aaaatgcatg gtctgtgtga tgttggtctg tgtgatgttg 1200
gtctgtgtga tgttggtctg tgtgatgttc tgcagaagct t 1241

<210> SEQ ID NO 33

-continued

```
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 33

ggatccgacg ggaacaaaga gaaagcacaa gtaaaaggca acgacgcgca cgaggtcaga      60

acgcaaacag gaagaagaat gcaacaaagg agcgccgaac ggatacgcgg gccaacacga     120

agaggaatga aagggaaacg aaacaaaaaa gtgaagaggc caaaagagca cagcatggag     180

gaagccacgg ccgaaaaact acaccgggaa ggaccaaacg cgatggcaga cagagcgcag     240

acagggatag agccacccag gaagcacgca gtcagggaga aaagggcaca gacactacga     300

aaaagggcga caagagggct gggagaggga acgggcagaa acataaaacc caagagccga     360

ccagaagtaa aaggcgatat caacacagac gtaaagcaag cagaacaaga gcacataagc     420

aagaaggaga ggagacacct accagagaga aaaacccgaa ccgtgcggaa aggcgggcga     480

gaagggataa aagagcacga acccaagagg atgaaaggac aagagagaac gaaagtccaa     540

cacagaaagg ccaaaggaat aaaaagcaac agccaaaaaa aagtaagaaa gcaagacaaa     600

gcgagaatga aaagcgaagg cacaaaagaa atagacagag ggaacagcgg aaagatccca     660

cgggcgacag caaccggact ccacgggaac acgaggagaa acgtgaaaac cgagcggcaa     720

cccagactca gcggaacaga agacaaaaaa atacgggcag ggcgaggaaa gaaaataggg     780

ccaacaaaaa ggaagcagat gaaaaacaca aaaacccacc acatcacgcg ggccgagagc     840

agcaacgtgg cagcacgagg aggaggagcc ctagaacgca aaggcgaaaa gacgctgcga     900

ggtaccgggc caaagaaaat aaaggaacgc aaacaaagga gcatcaaagg gaagaaacaa     960

aagaaaataa aaaaggagaa gaaagggaag ataaaaggaa acggaaaaaa gaaactcgcg    1020

acaaagacgg cagcaaaggt agaggaaaag gaagaggaca cactgaaaga gcaccaggag    1080

aaagacctag cagaagcacg ctcgag                                         1106
```